United States Patent [19]

Bodor

[11] Patent Number: 5,079,366

[45] Date of Patent: Jan. 7, 1992

US005079366A

[54] QUARTERNARY PYRIDINIUM SALTS

[75] Inventor: Nicholas S. Bodor, Gainesville, Fla.

[73] Assignee: University of Florida, Gainesville, Fla.

[21] Appl. No.: 417,037

[22] Filed: Oct. 4, 1989

Related U.S. Application Data

[62] Division of Ser. No. 35,648, Apr. 7, 1987, Pat. No. 4,888,427.

[51] Int. Cl.$^5$ .................. C07D 215/38; C07D 213/62; C07D 213/70; C07D 213/56
[52] U.S. Cl. .................... 546/175; 546/147; 546/169; 546/174; 546/286; 546/287; 546/288; 546/291; 546/294; 546/295; 546/296; 546/298; 546/299; 546/300; 546/315; 546/316; 546/318; 546/321; 546/322; 546/323; 546/326; 546/328; 546/335
[58] Field of Search ............... 546/286, 287, 288, 291, 546/294, 295, 296, 298, 299, 300, 315, 316, 318, 321, 322, 323, 326, 328, 335, 169, 174, 147, 175

[56] References Cited

U.S. PATENT DOCUMENTS

| | | | |
|---|---|---|---|
| 3,929,813 | 12/1975 | Higuchi et al. | 546/287 |
| 3,962,447 | 6/1976 | Higuchi et al. | 546/287 |
| 4,530,920 | 7/1985 | Nestor et al. | 546/286 |
| 4,540,564 | 9/1985 | Bodor | 546/287 |
| 4,565,804 | 1/1986 | Rivier et al. | 546/286 |
| 4,567,162 | 1/1986 | de Castiglione et al. | 546/286 |
| 4,568,754 | 2/1986 | Laruelle et al. | 546/286 |
| 4,569,927 | 2/1986 | Rivier et al. | 546/286 |
| 4,619,915 | 10/1986 | Ives | 546/286 |
| 4,638,046 | 1/1987 | Verdini et al. | 546/286 |

FOREIGN PATENT DOCUMENTS

8303968 11/1983 PCT Int'l Appl. .
8503937 9/1985 PCT Int'l Appl. .

OTHER PUBLICATIONS

Bodor et al., *J. Pharm. Sci.*, 67, No. 5, 685–687 (1978).
Bodor, "Novel Approaches for the Design of Membrane Transport Properties of Drugs", in *Design of Biopharmaceutical Properties Through Prodrugs and Analogs*, Roche, E. B. (ed.), APhA Academy of Pharmaceutical Sciences, Washington, D.C., 98–135 (1976).
Bodor et al., *Science*, vol. 214, Dec. 18, 1981, pp. 1370–1372.
Bodor et al., *Pharmacology and Therapeutics*, vol. 19, No. 3, pp. 337–386 (1983).
*The Friday Evening Post*, Aug. 14, 1981, Health Center Communications, University of Florida, Gainesville, Florida.
*Chemical & Engineering News*, Dec. 21, 1981, pp. 24–25.
*Science News*, Jan. 2, 1982, vol. 121, No. 1, p. 7.
J. S. Morley, *Annu. Rev. Pharmacol.* 20: 81–110 (1980).

*Primary Examiner*—Johann Richter
*Attorney, Agent, or Firm*—Mary K. Baumeister

[57] ABSTRACT

The invention provides novel amino acids and peptides containing them which comprise a dihydropyridine⇌pyridinium salt-type redox system and which provide site-specific and sustained delivery of pharmacologically active peptides to the brain. These new amino acids contain a redox system appended directly or via an alkylene bridge to the carbon atom adjacent to the carboxyl carbon and may be incorporated into a peptide chain at a variety of positions, including non-terminal positions.

30 Claims, No Drawings

QUARTERNARY PYRIDINIUM SALTS

This application is a division of application Ser. No. 07/035,648, filed Apr. 7, 1987, now U.S. Pat. No. 4,888,427.

FIELD OF THE INVENTION

The invention provides novel amino acids and peptides containing them which comprise a dihydropyridine⇌pyridinium salt-type redox system and which provide site-specific and sustained delivery of pharmacologically active peptides to the brain.

BACKGROUND OF THE INVENTION

The delivery of drug species to the brain is ofttimes seriously limited by transport and metabolism factors and, more specifically, by the functional barrier of the endothelial brain capillary wall, i.e. the blood-brain barrier or BBB. Site-specific delivery and sustained delivery of drugs to the brain are even more difficult.

Indeed, the barriers separating plasma from the brain and cerebrospinal fluid (CSF) are complex systems involving passive and active transport and serve a number of important functions. The boundary between plasma and the central nervous system (CNS) is much less permeable than that between plasma and other tissue cells to a variety of water soluble substances, such as organic electrolytes, organic acids and bases, as well as to large molecules such as proteins. Such a barrier also provides a path for clearance from the brain of the breakdown products of cellular metabolism. The CNS and its fluids can be considered basically a three-compartment system: the blood or the plasma, CSF and brain tissue. There is a diffusion-controlled exchange between CSF and the extracellular fluid (CF) of the brain. It has also been suggested that the permeabilities of blood-CSF and blood-brain barriers are practically identical with respect to drugs and other foreign substances. Mayer et al, J. Pharmacol. and Exp. Therap., 125, 185 (1959).

The BBB is, moreover, basically the result of the fact that the endothelial cells in the brain capillaries are joined by continuous, tight intercellular junctions, such that material has to pass through the cells rather than between them in order to move from blood to brain. It is interesting that there are areas within the brain, such as the subfornical body and the postremia, in which the capillary cells are not closely linked so that they lack the characteristics of the BBB. They provide the entry of small amounts of compounds which would not ordinarily enter the barriers. Hoffman and Olszewzki, Neurology (Minneap.), 11, 1081 (1961).

Foreign compounds which enter organs other than the central nervous system with ease, may penetrate the CNS slowly or hardly at all. A number of theories concerning the nature of the barrier have been proposed. The widely accepted concept describes the boundary as a fat-like layer interspersed with small pores, although the BBB is not a simple, anatomically well-defined unitary physical entity. Shuttleworth, Prog. Exp. Tumor Res., 17, 279 (1972). Penetration of such a barrier may occur by several processes: lipid soluble substances may passively penetrate into the cells, while small molecules such as water and urea may pass through the pores. In addition to these simple physical processes, carrier-mediated and active transport processes govern the movement of many molecules through the BBB. Thus, it is generally accepted that lipid solubility, degree of ionic dissociation or protonation and the ability of temporary combination with membrane constituents affect delivery through the BBB. It has been shown, for example, that in the class of barbiturates, a quantitative correlation could be established between their ease to pass into the brain (as reflected by the different times of onset of anesthetic action) and their lipid/water partition coefficient. Mark et al, J. Pharmacol. and Exp. Therap., 123, 79 (1957). The role of lipid solubility in drug penetration through the BBB is also exemplified by the better absorption of the sparingly water-soluble thiamine propyl disulfide (TPD) as compared to the water-soluble thiamine hydrochloride (THCl). Thomson et al, Ann. Int. Med., 74, 529 (1971). Some materials such as glucose and amino acids are transported by active mechanism, characterized by saturation, bidirectional molecular specificity, bidirectional competitive inhibition and bidirectional countertransport. Fishman, Am. J. Physiol., 206, 836 (1964).

Changes in permeability of the BBB can be caused by several pathological and toxicological processes. Pardridge, Connor and Crawford, CRC Crit. Rev. Toxicol., 179 (1975). A general increase in the barrier permeability, such as a nonspecific breakdown of the barrier has, however, several consequences, including cerebral edema.

It too is well documented that the BBB is relatively impermeable to the ionized forms of drugs and other molecules. Drugs which are weak organic electrolytes appear to pass from blood to CSF to reach a steady state ratio characteristic of each molecule according to its pKa and the existence of a normal pH gradient between blood and CSF. It is clear that it is the most difficult for quaternary pyridinium or ammonium salts to penetrate the BBB.

And removal of substances from the brain and CSF is obviously a significant factor in regulating drug concentrations in the CNS. There are several efflux processes: bulk flow via the arachnoid villi, diffusion of lipid soluble substances into brain and blood, active transport and metabolism by adjacent meninges. Once a drug or metabolite enters the CSF from blood or brain by simple diffusion, it may rapidly be removed, either by nonselective bulk flow or by active transport mechanism associated with the choroid plexus or other nondefined structures in the CSF compartment. It is generally accepted that highly lipid-soluble drugs leave the CSF more rapidly than poorly lipid-soluble ones, but the barrier to passage of compounds from CSF has only superficial similarity to the blood-CSF barrier.

Drug elimination processes from the brain are significantly directly related to drug accumulation in the brain. It is generally assumed that efflux in the opposite direction involves almost the same processes as for entry, except that the role of the bulk flow and the metabolic processes in the brain are not to be overlooked.

The two elimination processes studied in the earlier literature and which can be said to have a certain bearing on the present invention involve elimination from the brain of ionic species. Thus, it is found that non-metabolized ionic species, such as the acetate ion, have a three times slower elimination rate from the CSF than from the blood. Freundt, Arz. Forsch., 23, 949 (1973). An even more dramatic change in the elimination rate was found in the case of a quaternary piperidinium salt. The quaternary salt, formed in situ after delivery of a haloalkylamine, which undergoes cyclization to the quaternary salt in the brain as well, was found to have an at least ten times slower elimination rate from the brain than from the rest of the body. It was concluded by the authors [Ross and Froden, Eur. J. Pharmacol., 13, 46 (1970)] that the outflow rate of the quaternary salt corresponded to the inflow rate. Similar results were obtained for the erythrocytes: the efflux of the quaternary salt was very slow. Ross, J. Pharm. Pharmacol., 27, 322 (1975).

A dihydropyridine⇌pyridinium redox system has recently been successfully applied to delivery to the brain of a number of drugs. Generally speaking, according to this system, a dihydropyridine derivative of a biologically active compound is synthesized, which derivative can enter the CNS through the blood-brain barrier following its systemic administration. Subsequent oxidation of the dihydropyridine species to the corresponding pyridinium salt leads to delivery of the drug to the brain.

Three main approaches have been used thus far for delivering drugs to the brain using this redox system. The first approach involves derivation of selected drugs which contain a pyridinium nucleus as an integral structural component. This approach was first applied to delivering to the brain N-methylpyridinium-2-carbaldoxime chloride (2-PAM), the active nucleus of which constitutes a quaternary pyridinium salt, by way of the dihydropyridine latentiated prodrug form thereof. rapid elimination from the general circulation, enhanced drug efficacy and decreased toxicity. No "trapping" in the brain of the 2-PAM formed in situ resulted, and obviously no brain-specific, sustained delivery occurred as any consequence thereof: the 2-PAM was eliminated as fast from the brain as it was from the general circulation and other organs. Compare U.S. Pat. Nos. 3,929,813 and 3,962,447; Bodor et al, J. Pharm. Sci., 67, No. 5, 685 (1978). See also Bodor, "Novel Approaches for the Design of Membrane Transport Properties of Drugs", in Design of Biopharmaceutical Properties Through Prodrugs and Analogs, Roche, E. B. (ed.), APhA Academy of Pharmaceutical Sciences, Washington, D.C., 98-135 (1976). Subsequent extension of this first approach to delivering a much larger quaternary salt, berberine, to the brain via its dihydropyridine prodrug form was, however, found to provide site-specific sustained delivery to the brain of that anticancer agent. See Bodor et al, Science, Vol. 214, Dec. 18, 1981, pp. 1370-1372.

The second approach for delivering drugs to the brain using the redox system involves the use of a dihydropyridine/pyridinium carrier chemically linked to a biologically active compound. Bodor et al, Science, Vol. 214, Dec. 18, 1981, pp. 1370-1372, outlines a scheme for this specific and sustained delivery of drug species to the brain, as depicted in the following Scheme 1

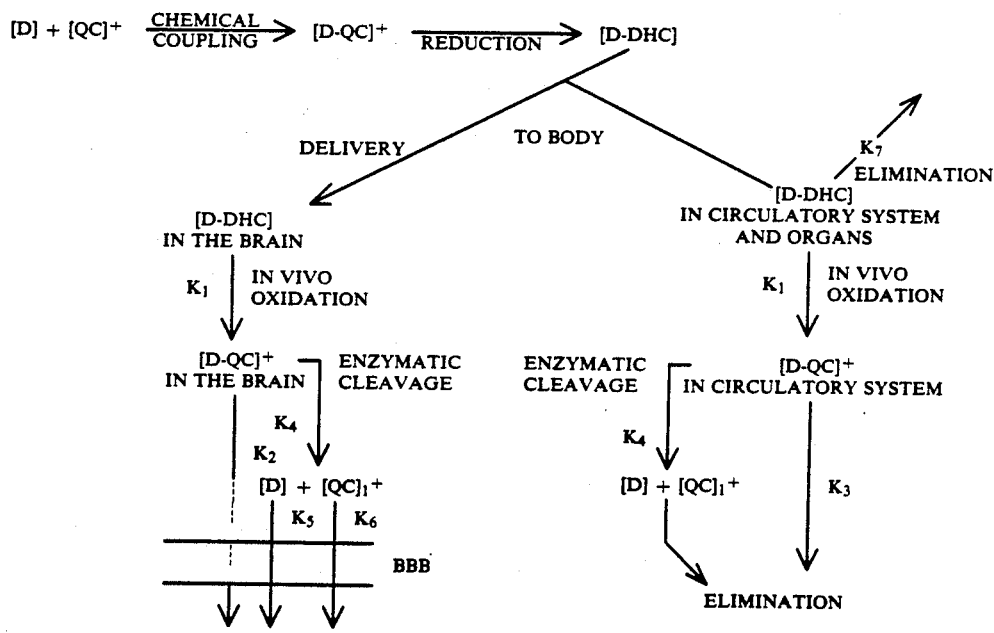

Thus, a hydrophilic compound (2-PAM) was made lipoidal (i.e. lipophilic) by making its dihydropyridine form (Pro-2-PAM) to enable its penetration through lipoidal barriers. This simple prodrug approach allowed the compound to get into the brain as well as other organs, but this manipulation did not and could not result in any brain specificity. On the contrary, such approach was delimited to relatively small molecule quaternary pyridinium ring-containing drug species and did not provide the overall ideal result of brain-specific, sustained release of the desired drug, with concomitant According to the scheme in Science, a drug [D] is coupled to a quaternary carrier [QC]$^+$ and the [D-QC]$^+$ which results is then reduced chemically to the lipoidal dihydro form [D-DHC]. After administration of [D-DHC] in vivo, it is rapidly distributed throughout the body, including the brain. The dihydro form [D-DHC] is then in situ oxidized (rate constant, $k_1$) (by the NAD⇌NADH system) to the ideally inactive original [D-QC]$^+$ quaternary salt which, because of its ionic, hydrophilic character, should be rapidly eliminated from the general circulation of the body, while the blood-brain barrier should prevent its elimination from the brain ($k_3 \gg k_2$; $k_3 \gg k_7$). Enzymatic cleavage of the [D-QC]+ that is "locked" in the brain effects a sustained delivery of the drug species [D], followed by its normal elimination ($k_5$), metabolism. A properly selected carrier [QC]+ will also be rapidly eliminated from the brain ($k_6 \gg k_2$). Because of the facile elimination of [D-QC]+ from the general circulation, only minor amounts of drug are released in the body ($k_3 \gg k_4$); [D] will be released primarily in the brain ($k_4 > k_2$). The overall result ideally will be a brain-specific sustained release of the target drug species. Specifically, Bodor et al worked with phenylethylamine as the drug model. That compound was coupled to nicotinic acid, then quaternized to give compounds of the formula

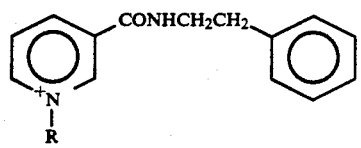

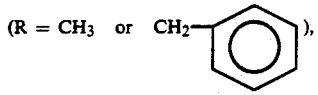

which were subsequently reduced by sodium dithionite to the corresponding compounds of the formula

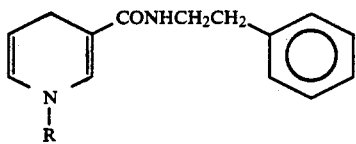

(R = CH₃ or CH₂—⌬).

Testing of the N-methyl derivative in vivo supported the criteria set forth in Scheme 1. Bodor et al speculated that various types of drugs might possibly be delivered using the depicted or analogous carrier systems and indicated that use of N-methylnicotinic acid esters and amides and their pyridine ring-substituted derivatives was being studied for delivery of amino- or hydroxyl-containing drugs, including small peptides, to the brain. No other possible specific carriers were disclosed. Other reports of this work with the redox carrier system have appeared in The Friday Evening Post, Aug. 14, 1981, Health Center Communications, University of Florida, Gainesville, Fla; Chemical & Engineering News, Dec. 21, 1981, pp. 24-25; and Science News, Jan. 2, 1982, Vol. 121, No. 1, page 7. More recently, the redox carrier system has been substantially extended in terms of possible carriers and drugs to be delivered. See International Patent Application No. PCT/US83/00725, filed May 12, 1983 and published Nov. 24, 1983 under International Publication No. WO83/03968. Also see Bodor et al, Pharmacology and Therapeutics, Vol. 19, No. 3, pp. 337-386 (1983); and Bodor U.S. Pat. No. 4,540,564, issued Sept. 10, 1985.

The aforementioned Bodor U.S. Pat. No. 4,540,564 specifically contemplates application of the dihydropyridine⇌pyridinium salt carrier system to amino acids and peptides, particularly small peptides having 2 to 20 amino acid units. Among the amino acids and peptides mentioned in the patent are GABA, tyrosine, tryptophan, met[5]-enkephalin, leu[5]-enkephalin, LHRH and its analogs and others. Representative carrier-linked amino acids and peptides illustrated in the Bodor patent are the following:

| AMINO ACID/PEPTIDE | CARRIER-DRUG (QUATERNARY) | CARRIER-DRUG (DIHYDRO) |
|---|---|---|
| Tyr—Gly—Gly—Phe—Leu<br>(leu⁵-enkephalin) | H₃C—N⁺(pyridinium)—CNH—CH₂CH₂CH₂COOC₂H₅ ‖ O | (not depicted) |
|  | H₃C—N⁺(pyridinium)—C—Tyr—Gly—Gly—Phe—Leu—OC₂H₅ ‖ O |  |

Thus, in the depicted carrier system as applied to amino acids and peptides, the free carboxyl function is suitably protected to prevent premature metabolism while the trigonelline-type carrier is linked to the amino acid or peptide through its free amino function. Oxidation of the dihydropyridine carrier moiety in vivo to the ionic pyridinium salt carrier/drug entity prevents elimination thereof from the brain, while elimination from the general circulation is accelerated, and subsequent cleavage of the quaternary carrier/drug species results in sustained delivery of the amino acid or peptide (e.g. tryptophan, GABA, leu⁵-enkephalin, etc.) in the brain and facile elimination of the carrier moiety.

The third approach for delivering drugs to the brain using the redox system provides derivatives of centrally acting amines in which a primary, secondary or tertiary amine function has been replaced with a dihydropyridine/pyridinium salt redox system. These brain-specific analogs of centrally acting amines have been recently described in International Patent Application No. PCT/US85/00236, filed Feb. 15, 1985 and published Sept. 12, 1985 under International Publication No. WO85/03937. The dihydropyridine analogs are characterized by the structural formula

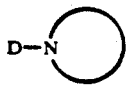

wherein D is the residue of a centrally acting primary, secondary or tertiary amine, and

is a radical of the formula

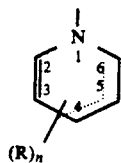

(a)

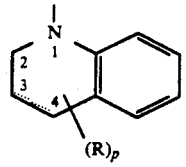

(b)

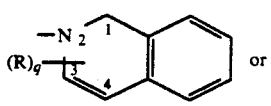

or (c)

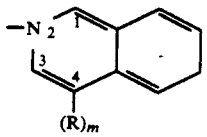

(d)

wherein the dotted line in formula (a) indicates the presence of a double bond in either the 4 or 5 position of the dihydropyridine ring; the dotted line in formula (b) indicates the presence of a double bond in either the 2 or 3 position of the dihydroquinoline ring system; m is zero or one; n is zero, one or two; p is zero, one or two, provided that when p is one or two, each R in formula (b) can be located on either of the two fused rings; q is zero, one, or two, provided that when q is one or two, each R in formula (c) can be located on either of the two fused rings; and each R is independently selected from the group consisting of halo, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is H or $C_1$-$C_7$ alkyl, and —CONR'R'' wherein R' and R'', which can be the same or different, are each H or $C_1$-$C_7$ alkyl. These dihydropyridine analogs act as a delivery system for the corresponding biologically active quaternary compounds in vivo. Due to its lipophilic nature, the dihydropyridine analog will distribute throughout the body and has easy access to the brain through the blood-brain barrier. Oxidation in vivo will then provide the quaternary form, which will be "locked" preferentially in the brain. In contradistinction to the drug-carrier entities described in Bodor U.S. Pat. No. 4,540,564 and related publications, however, there is no readily metabolically cleavable bond between drug and quaternary portions, and the active species delivered is not the original drug from which the dihydro analog was derived, but rather is the quaternary analog itself.

The aforementioned International Publication No. WO85/03937 contemplates application of its analog system to amino acids and small peptides, e.g. the enkephalins, tryptophan, GABA, LHRH analogs and others. Illustrated redox analogs include the following:

acids which could be used to synthesize peptides having the redox system inserted at a variety of locations in the peptide chain.

SUMMARY AND OBJECTS OF THE INVENTION

Accordingly, a major object of the present invention

| AMINO ACID/PEPTIDE | QUATERNARY ANALOG | DIHYDROPYRIDINE ANALOG |
|---|---|---|
| 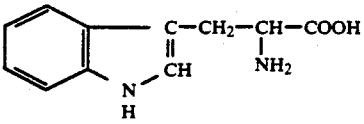 (tryptophan) | 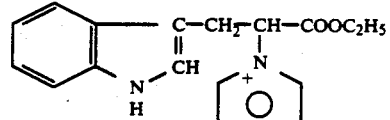 | 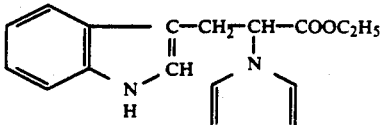 |
| NH₂—CH₂CH₂CH₂COOH (GABA) |  | 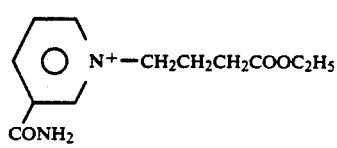 |
| 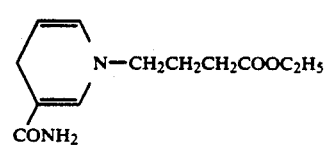 (tyrosine) | 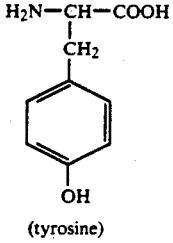 | 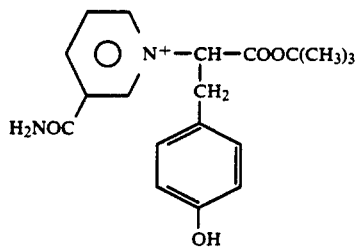 |
| 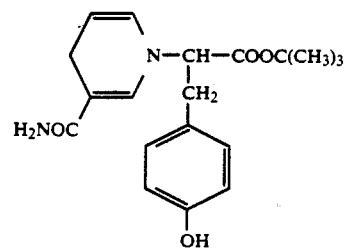 (tyrosine) | 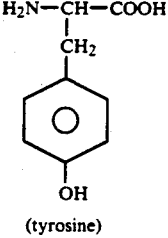 | 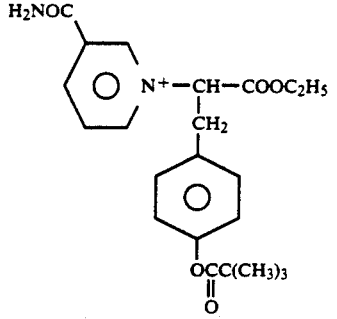 |

In the depicted analog system as applied to amino acids and peptides, the free carboxyl function is thus suitably protected to prevent premature metabolism while the dihydropyridine⇌pyridinium salt type redox system replaces the free amino function in the amino acid or peptide.

As described in International Publication No. WO85/03937, the chemical processes for preparing the redox analog derivatives replace any free amino function in the selected drug with the redox analog system. When these processes are applied to amino acids, they provide a redox amino acid which no longer contains a free amino function for linkage to another amino acid or peptide via a peptide bond (—CONH—). Such an analog amino acid can thus only be used to prepare a peptide having the analog amino acid located at the peptide's N-terminus. This severely limits use of the redox analog amino acids in peptide synthesis. It therefore would be desirable to provide a new approach for delivering peptides to the brain using the redox system, which approach would provide novel redox amino is the provision of a new approach for delivering peptides to the brain using the redox system. This approach provides novel amino acids and peptides containing them which comprise a dihydropyridine⇌pyridinium salt redox system. These new amino acids contain the redox system appended directly or via an alkylene bridge to the carbon atom adjacent to the carboxyl carbon. The redox amino acids of this invention are useful in the preparation of novel, biologically active peptides which are brain-specific and which provide sustained in-brain activity, including many peptides in which the redox amino acid is located in a non-terminal position of the peptide chain.

Consistent with the foregoing, the present invention provides novel amino acids which, in the reduced form, have the structural formula

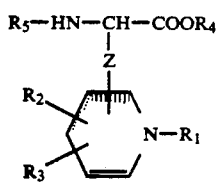

(I)

wherein Z is either a direct bond or $C_1$-$C_6$ alkylene and can be attached to the heterocyclic ring via a ring carbon atom or via the ring nitrogen atom; $R_1$ is $C_1$-$C_7$ alkyl, $C_1$-$C_7$ haloalkyl or $C_7$-$C_{12}$ aralkyl when Z is attached to a ring carbon atom; $R_1$ is a direct bond when Z is attached to the ring nitrogen atom; $R_2$ and $R_3$, which can be the same or different, are selected from the group consisting of hydrogen, halo, cyano, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is hydrogen or $C_1$-$C_7$ alkyl, and —CONR'R'' wherein R' and R'', which can be the same or different, are each hydrogen or $C_1$-$C_7$ alkyl; or one of $R_2$ and $R_3$ together with the adjacent ring carbon atom forms a benzene ring fused to the heterocyclic ring, which benzene ring may optionally bear one or two substituents, which can be the same or different, selected from the group consisting of hydroxy, protected hydroxy, halo, cyano, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is hydrogen or $C_1$-$C_7$ alkyl, and —CONR'R'' wherein R' and R'', which can be the same or different, are each hydrogen or $C_1$-$C_7$ alkyl; $R_4$ is hydrogen or a carboxyl protective group; $R_5$ is hydrogen or an amino protective group; and the dotted lines indicate that the compound of formula (I) contains a 1,4- or 1,6-dihydropyridine, a 1,4- or 1,2-dihydroquinoline, or a 1,2-dihydroisoquinoline ring system.

The non-toxic pharmaceutically acceptable salts of the compounds of formula (I) are also within the ambit of this invention.

The corresponding oxidized or quaternary form of the redox amino acids of the present invention can be represented by the formula

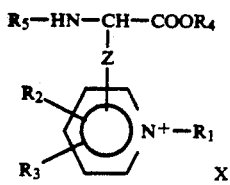

(II)

wherein $X^-$ is the anion of a non-toxic pharmaceutically acceptable acid and Z, $R_1$, $R_2$, $R_3$, $R_4$ and $R_5$ are as defined with formula (I).

The new dihydropyridine and pyridinium salt-type amino acids of formulas (I) and (II) are useful in the preparation of novel redox peptides of the partial formulas:

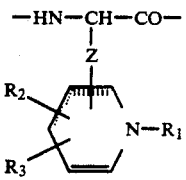

(A)

(reduced form)

and

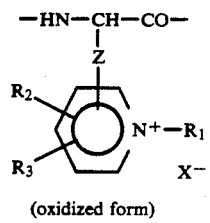

(B)

(oxidized form)

wherein Z, $R_1$, $R_2$, $R_3$, $X^-$ and the dotted lines are as defined with formulas (I) and (II), the remainder of the peptide structure being defined hereinbelow.

The new peptide analogs of partial structure (A) act as a delivery system for the corresponding quaternary salts of partial structure (B) in vivo; the quaternary derivatives, which also are chemical intermediates to the dihydro compounds, are pharmacologically active or convertible in vivo to pharmacologically active peptides, and are characterized by site-specific and sustained delivery to the brain when administered via the corresponding dihydropyridine form.

DETAILED DESCRIPTION OF THE INVENTION

More particularly in accord with the present invention, the following definitions are applicable:

The term "lipoidal" as used herein is intended to mean lipid-soluble or lipophilic.

The term "$C_1$-$C_6$ alkylene" as used herein encompasses bivalent radicals of the type —$(CH_2)_n$— wherein n is 1 to 6, as well as the corresponding branched chain groups, e.g. methylene, ethylene, propylene, trimethylene, 1,2-butylene, 2,3-butylene, tetramethylene and the like. Preferably, $C_1$-$C_6$ alkylene is —$(CH_2)_n$— wherein n is 1 or 4.

The term "halo" encompasses fluoro, chloro, bromo and iodo.

The term "$C_1$-$C_7$ alkyl" includes straight and branched lower alkyl radicals having up to seven carbon atoms. When $R_2$ and/or $R_3$ are $C_1$-$C_7$ alkyl, they are preferably methyl or ethyl. When $R_1$ is $C_1$-$C_7$ alkyl, it is preferably methyl.

The term "$C_1$-$C_7$ alkoxy" includes straight and branched chain lower alkoxy radicals having up to seven carbon atoms. When $R_2$ and/or $R_3$ are $C_1$-$C_7$ alkoxy, they are preferably methoxy or ethoxy.

The term "$C_2$-$C_8$ alkoxycarbonyl" designates straight and branched chain radicals of the formula

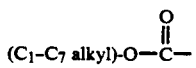

wherein the $C_1$-$C_7$ alkyl group is defined as above. When $R_2$ and/or $R_3$ are alkoxycarbonyl, they are preferably ethoxycarbonyl or isopropoxycarbonyl.

The term "$C_2$-$C_8$ alkanoyloxy" designates straight and branched chain radicals of the formula

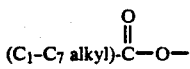

wherein the $C_1$-$C_7$ alkyl group is defined as above. When $R_2$ and/or $R_3$ are alkanoyloxy, they are preferably acetoxy, pivalyloxy or isobutyryloxy.

The term "$C_1$-$C_7$ haloalkyl" designates straight and branched chain lower alkyl radicals having up to seven carbon atoms and bearing one to three halo substituents (F, Cl, Br or I), which can be the same or different. Specific examples of the contemplated monohaloalkyl and polyhaloalkyl groups include chloromethyl, dichloromethyl, trichloromethyl, bromomethyl, fluoromethyl, difluoromethyl, trifluoromethyl, 1-fluoroethyl, 1-chloroethyl, 2-chloroethyl, 2,2,2-trichloroethyl, 2,2,2-trifluoroethyl, 1,2-dichloroethyl, 1-chloropropyl, 3-chloropropyl, 1-chlorobutyl, 1-chloropentyl, 1-chlorohexyl, 4-chlorobutyl and the like. Preferably, the haloalkyl group contains 1 or 2 carbon atoms and bears 1 to 3 halogen substituents, e.g. chloromethyl or trifluoromethyl.

The term "$C_1$-$C_7$ alkylthio" includes straight and branched chain radicals of the type

wherein $C_1$-$C_7$ alkyl is defined as before. When $R_2$ and/or $R_3$ are alkylthio, they are preferably methylthio.

The terms "$C_1$-$C_7$ alkylsulfinyl" and "$C_1$-$C_7$- alkylsulfonyl" designate radicals of the formulas

and

respectively, wherein $C_1$-$C_7$ alkyl is defined as before. When $R_2$ and/or $R_3$ are alkylsulfinyl or alkylsulfonyl, methylsulfinyl and methylsulfonyl are preferred.

When $R_2$ and/or $R_3$ are —CH=NOR''', they are preferably —CH=NOH or —CH=NOCH$_3$.

When $R_2$ and/or $R_3$ are —CONR'R'', they are preferably —CONH$_2$ or —CON(CH$_3$)$_2$.

The term "$C_7$-$C_{12}$ aralkyl" as used herein designates radicals of the type

wherein the aryl portion is phenyl or naphthyl and the alkylene portion, which can be straight or branched, can contain up to 6 carbon atoms, e.g. methylene, ethylene, propylene, trimethylene, 1,2-butylene, 2,3-butylene, tetramethylene and the like. When $R_1$ is aralkyl, it is preferably benzyl.

The expression "non-toxic pharmaceutically acceptable salts" as used herein generally includes the non-toxic salts of compounds of formulas (I) and (A) formed with non-toxic, pharmaceutically acceptable inorganic or organic acids HX. For example, the salts include those derived from inorganic acids such as hydrochloric, hydrobromic, sulfuric, sulfamic, phosphoric, nitric and the like; and the salts prepared from organic acids such as acetic, propionic, succinic, glucolic, stearic, lactic, malic, tartaric, citric, ascorbic, pamoic, maleic, hydroxymaleic, phenylacetic, glutamic, benzoic, salicylic, sulfanilic, fumaric, methanesulfonic, toluenesulfonic and the like. The expression "anion of a non-toxic pharmaceutically acceptable acid" as used herein, e.g. in connection with structures (II) and (B), is intended to include anions of such organic or inorganic acids HX.

The expression "hydroxyl protective group" as used herein is intended to designate a group (Y) which is inserted in place of a hydrogen atom of an OH group or groups in order to protect the OH group(s) during synthesis and/or to improve lipoidal characteristics and prevent premature metabolism of the OH group(s) prior to the compound's reaching the desired site in the body. The expression "protected hydroxy substituent" designates an OY group wherein Y is a "hydroxyl protective group" as defined above.

Typical hydroxyl protective groups contemplated by the present invention are acyl groups and carbonates. When the hydroxyl protective group is acyl (i.e., when it is an organic radical derived from a carboxylic acid by removal of the hydroxyl group), it preferably represents an acyl radical selected from the group consisting of alkanoyl having 2 to 8 carbon atoms; alkenoyl having one or two double bonds and 3 to 8 carbon atoms;

wherein the cycloalkyl portion contains 3 to 7 ring atoms and r is zero, one, two or three; phenoxyacetyl; pyridinecarbonyl; and

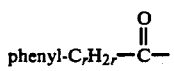

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

When the acyl group is alkanoyl, there are included both unbranched and branched alkanoyl, for example, acetyl, propionyl, butyryl, isobutyryl, valeryl, isovaleryl, 2-methylbutanoyl, pivalyl (pivaloyl), 3-methylpentanoyl, 3,3-dimethylbutanoyl, 2,2-dimethylpentanoyl and the like. Pivalyl, isobutyryl and isovaleryl are especially preferred.

When the acyl group is alkenoyl, there are included, for example, crotonyl, 2,5-hexadienoyl and 3,6-octadienoyl.

When the acyl group is

there are included cycloalkanecarbonyl and cycloalkanealkanoyl groups wherein the cycloalkane portion can optionally bear 1 or 2 alkyl groups as substituents, e.g. cyclopropanecarbonyl, 1-methylcyclopropanecarbonyl, cyclopropaneacetyl, α-methylcyclopropaneacetyl, 1-methylcyclopropaneacetyl, cyclopropanepropionyl, α-methylcyclopropanepropionyl, 2-isobutylcyclopropanepropionyl, cyclobutanecarbonyl, 3,3-dimethylcyclobutanecarbonyl, cyclobutaneacetyl, 2,2-dimethyl-3-ethylcyclobutaneacetyl, cyclopentanecarbonyl, cyclohexaneacetyl, cyclohexanecarbonyl, cycloheptanecarbonyl and cycloheptanepropionyl. Cyclohexanecarbonyl is especially preferred.

When the acyl group is pyridinecarbonyl, there are included picolinoyl (2-pyridinecarbonyl), nicotinoyl (3-pyridinecarbonyl) and isonicotinoyl (4-pyridinecarbonyl).

When the acyl group is

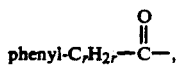

there are included, for example, benzoyl, phenylacetyl, α-phenylpropionyl, β-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, β-(p-ethylphenyl)propionyl, p-anisoyl, m-anisoyl, o-anisoyl, m-isopropoxybenzoyl, p-methoxyphenylacetyl, m-isobutoxyphenylacetyl, m-diethylaminobenzoyl, 3-methoxy-4-ethoxybenzoyl, 3,4,5-trimethoxybenzoyl, p-dibutylaminobenzoyl, 3,4-diethoxyphenylacetyl, β-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, α-(m-bromophenyl)propionyl, p-trifluoromethylbenzoyl, 2,4-di(trifluoromethyl)benzoyl, m-trifluoromethylphenylacetyl, β-(3-methyl-4-chlorophenyl)propionyl, p-dimethylaminobenzoyl, p-(N-methyl-N-ethylamino)benzoyl, o-acetamidobenzoyl, m-propionamidobenzoyl, 3-chloro-4-acetamidophenylacetyl, p-n-butoxybenzoyl, 2,4,6-triethoxybenzoyl, β-(p-trifluoromethylphenyl)propionyl, 2-methyl-4-methoxybenzoyl, p-acetamidophenylpropionyl, and 3-chloro-4-ethoxybenzoyl.

When the hydroxyl protective group is a carbonate grouping, it has the structural formula

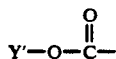

i.e., it is an organic radical which can be considered to be derived from a carbonic acid by removal of the hydroxyl group from the COOH portion. Y' preferably represents alkyl having 1 to 7 carbon atoms; alkenyl having one or two double bonds and 2 to 7 carbon atoms;

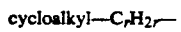

wherein the cycloalkyl portion contains 3 to 7 ring atoms and r is zero, one, two or three; phenoxy; 2-, 3-, or 4-pyridyl; or

wherein r is zero, one or two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. Most preferably, Y' is $C_1$-$C_7$ alkyl, particularly ethyl or isopropyl.

Similarly, the expression "carboxyl protective group" as used herein is intended to designate a group (W) which is inserted in place of a hydrogen atom of a COOH group or groups in order to protect the COOH group(s) during synthesis and/or to improve lipoidal characteristics and prevent premature metabolism of said COOH group or groups prior to the compound's reaching the desired site in the body. Typical of such carboxyl protective groups W are the groups encompassed by Y' above, especially $C_1$-$C_7$ alkyl, particularly ethyl, isopropyl and t-butyl. While such simple alkyl esters and the like are often useful, other carboxyl protecting groups may be selected, e.g. in order to eve greater control over the rate of in vivo is of the ester back to the acid and thus enhance drug delivery. To that end, carboxyl protecting groups W such as the following may be used to replace the hydrogen of the —COOH group:

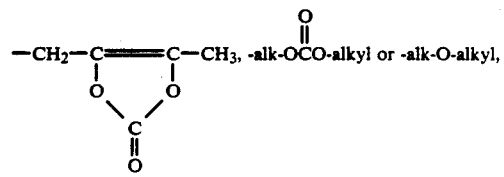

wherein alk is $C_1$-$C_6$ straight or branched alkylene and the alkyl radical is straight or branched and contains 1 to 7 carbon atoms

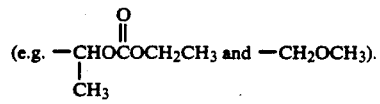

Other carboxyl protective groups W which can be used to replace the hydrogen of the —COOH group and which are especially useful herein are the following:

wherein p is 0, 1, 2 or 3;

$C_6$-$C_{28}$ polycycloalkyl—$C_pH_{2p}$— wherein p is defined as above;

wherein p is defined as above;

wherein p is defined as above:

—$CH_2$—$X_a$—$R_a$ wherein $X_a$ is S, SO or $SO_2$ and $R_a$ is $C_1$-$C_7$ alkyl or $C_3$-$C_{12}$ cycloalkyl;

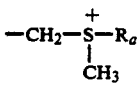

wherein $R_a$ is defined as above;

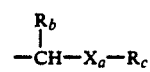

wherein $X_a$ is defined as above, $R_b$ is $C_1$-$C_7$ alkyl and $R_c$ is $C_1$-$C_7$ alkyl or wherein $R_b$ and $R_c$ taken together represent —$(CH_2)_{m'}$— wherein m' is 3 or 4 and —$(CH_2)_{m'}$— is optionally substituted by one to three $C_1$-$C_7$ alkyl;

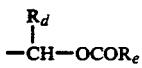

wherein $R_d$ is hydrogen or $C_1$-$C_7$ alkyl and $R_e$ is unsubstituted or substituted $C_1$-$C_{12}$ alkyl [e.g.

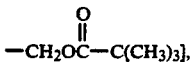

$C_3$-$C_{12}$ cycloalkyl-$C_pH_{2p}$— wherein p is defined as above, $C_3$-$C_{12}$ cycloalkenyl—$C_pH_{2p}$— wherein p is defined as above or $C_2$-$C_8$ alkenyl, the substituents being selected from the group consisting of halo, $C_1$-$C_7$ alkoxy, $C_1$-$C_7$ alkylthio, $C_1$-$C_7$ alkylsulfinyl, $C_1$-$C_7$ alkylsulfonyl,

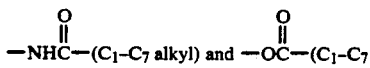

alkyl), or $R_e$ is unsubstituted or substituted phenyl or benzyl, the substituents being selected from the group consisting of $C_1$-$C_7$ alkyl, $C_1$-$C_7$ alkoxy, halo, carbamoyl, $C_2$-$C_8$ alkoxycarbonyl, $C_2$-$C_8$ alkanoyloxy, $C_1$-$C_7$ haloalkyl, mono($C_1$-$C_7$ alkyl)amino, di($C_1$-$C_7$ alkyl)amino, mono($C_1$-$C_7$ alkyl)carbamoyl, di($C_1$-$C_7$ alkyl)carbamoyl, $C_1$-$C_7$ alkylthio, $C_1$-$C_7$ alkylsulfinyl and $C_1$-$C_7$ alkylsulfonyl, or $R_e$ is $C_6$-$C_{28}$ polycycloalkyl—$C_pH_{2p}$— or $C_6$-$C_{28}$ polycycloalkenyl—$C_pH_{2p}$— wherein p is defined as above;

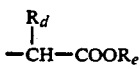

wherein $R_d$ and $R_e$ are defined as above; and

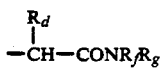

wherein $R_d$ is defined as above and $R_f$ and $R_g$, which can be the same or different, are each hydrogen, $C_1$-$C_7$ alkyl, $C_3$-$C_{12}$ cycloalkyl—$C_pH_{2p}$—, $C_3$-$C_{12}$ cycloalkenyl-$C_pH_{2p}$—, phenyl or benzyl, or one of $R_f$ and $R_g$ is hydrogen, $C_1$-$C_7$ alkyl, $C_3$-$C_{12}$ cycloalkyl—$C_pH_{2p}$—, $C_3$-$C_{12}$ cycloalkenyl—$C_pH_{2p}$—, phenyl or benzyl and the other of $R_f$ and $R_g$ is $C_6$-$C_{28}$ polycycloalkyl—$C_pH_{2p}$— or $C_6$-$C_{28}$ polycycloalkenyl—$C_pH_{2p}$—, or $R_f$ and $R_g$ are combined such that —$NR_fR_g$ represents the residue of a saturated monocyclic secondary amine.

When the carboxyl protecting group is $C_3$-$C_{12}$ cycloalkyl—$C_pH_{2p}$— or otherwise contains a $C_3$-$C_{12}$ cycloalkyl group, the cycloalkyl groups contain 3 to 8 ring atoms and may optionally bear one or more, preferably one to four, alkyl substituents. Exemplary such cycloalkyl groups are cyclopropyl, 2-methylcyclopropyl, 3-ethylcyclopropyl, 2-butylcyclopropyl, 3-pentylcyclopropyl, 2-hexylcyclopropyl, cyclobutyl, 2-methylcyclobutyl, 2,3-dimethylcyclobutyl, 3-butylcyclobutyl, 4-hexylcyclobutyl, 2,3,3-trimethylcyclobutyl, 3,3,4,4-tetramethylcyclobutyl, cyclopentyl, 2-methylcyclopentyl, 3-ethylcyclopentyl, 4-butylcyclopentyl, 5-methylcyclopentyl, 3-pentylcyclopentyl, 4-hexylcyclopentyl, 2,3-dimethylcyclopentyl, 2,2,5,5-tetramethylcyclopentyl, 2,3,4-trimethylcyclopentyl, 2,4-dimethyl-3-ethylcyclopentyl, 2,2,3,4,4-pentamethylcyclopentyl, 2,3-dimethyl-3-propylcyclopentyl, cyclohexyl, 2,6-dimethylcyclohexyl, 3,3,5,5-tetramethylcyclohexyl, 2-methylcyclohexyl, 2-ethylcyclohexyl, 4-propylcyclohexyl, 5-butylcyclohexyl, 2,3-dimethylcyclohexyl, 2,4-dimethylcyclohexyl, 2,5-dimethylcyclohexyl, 2,3,4-trimethylcyclohexyl, 2,3-dimethyl-5-ethylcyclohexyl, 2,5-dimethyl-6-propylcyclohexyl, 2,4-dimethyl-3-butylcyclohexyl, 2,2,4,4-tetramethylcyclohexyl, 3,3,6,6-tetramethylcyclohexyl, 3,3,4,5,5-pentamethylcyclohexyl, 3,3,4,5,5,6-hexamethylcyclohexyl, 3,3,5-trimethyl-4-ethylcyclohexyl, 3,4,4-trimethyl-5-propylcyclohexyl, cycloheptyl, 3-methylcycloheptyl, 5-propylcycloheptyl, 6-butylcycloheptyl, 7-methylcycloheptyl, cyclooctyl, 2-methylcyclooctyl, 3-ethylcyclooctyl, 3,3,4-trimethylcyclooctyl, 3,3,5,5-tetramethylcyclooctyl and the like. Among the presently preferred cycloalkyl—$C_pH_{2p}$— carboxyl protecting groups are cyclohexyl, 2,6-dimethylcyclohexyl and 3,3,5,5-tetramethylcyclohexyl. Thus, when the carboxyl protective group is cycloalkyl—$C_pH_{2p}$—, p is preferably zero or one, most preferably zero.

When the carboxyl protecting group is $C_3$-$C_{12}$ cycloalkenyl—$C_pH_{2p}$— or otherwise contains a $C_3$-$C_{12}$ cycloalkenyl group, the corresponding unsaturated radicals such as cyclopentenyl and cyclohexenyl and the like are contemplated. Again, when the protective group is $C_3$-$C_{12}$ cycloalkenyl—$C_pH_{2p}$—, p is preferably zero or one, most preferably zero.

The polycycloalkyl—$C_pH_{2p}$— radicals which can serve as carboxyl protective groups, or as portions of carboxyl protective groups, are bridged or fused saturated alicyclic hydrocarbon systems consisting of two or more rings, optionally bearing one or more alkyl substituents and having a total of 6 to 28 carbon atoms in the ring portion. The corresponding bridged or fused unsaturated alicyclic hydrocarbon systems are intended by the term "$C_6$-$C_{28}$ polycycloalkenyl—$C_pH_{2p}$—". Such polycycloalkyl and polycycloalkenyl radicals are exemplified by adamantyl (especially 1- or 2-adamantyl), adamantylmethyl (especially 1-adamantylmethyl), adamantylethyl (especially 1-adamantylethyl), bornyl, norbonyl, (e.g. exo-norbornyl or endo-norbornyl), norbornenyl (e.g. 5-norbornen-2-yl), norbornylmethyl (e.g. 2-norbornylmethyl) and norbornylethyl (e.g. 2-norbornylethyl), and by radicals of the type

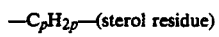

wherein p is defined as above and the sterol residue is the portion of a steroidal alcohol which remains after removal of a hydrogen atom from a hydroxy group therein. The sterol residue is preferably that of a pharmacologically inactive steroid, e.g. cholesterol, a bile acid (cholic acid or related compound) or the like. In the case of polycyclic radicals, p is preferably 0, 1 or 2.

When the carboxyl protective group is

wherein —NR$_f$R$_g$ represents the residue of a saturated monocyclic secondary amine, such monocycles preferably have 5 to 7 ring atoms optionally containing another hetero atom (—O—, —S— or —N—) in addition to the indicated nitrogen atom, and optionally bear one or more substituents such as phenyl, benzyl and methyl. Illustrative of residues of saturated monocyclic secondary amines which are encompassed by the —NR$_f$R$_g$ term are morpholino, 1-pyrrolidinyl, 4-benzyl-1-piperazinyl, perhydro-1,2,4-oxathiazin-4-yl, 1- or 4- piperazinyl, 4-methyl-1-piperazinyl, piperidino, hexamethyleneimino, 4-phenylpiperidino, 2-methyl-1-pyrazolidinyl, 1- or 2-pyrazolidinyl, 3-methyl-1-imidazolidinyl, 1- or 3-imidazolidinyl, 4-benzyl-piperidino and 4-phenyl-1-piperazinyl.

Carboxyl protecting groups of the type —CH$_2$COOR in which R is linear or branched C$_1$–C$_{12}$ alkyl or C$_5$–C$_{16}$ mono-alicyclic or polycyclic are described in Laruelle et al U.S. Pat. No. 4,568,754. Those groups are said to be useful in providing derivatives of 5-hydroxy-tryptophan (5-HTP) which are resistant to Peripheral decarboxylation and which regenerate 5-HTP at the cerebral level, in this way increasing passage through the blood-brain barrier. The Laruelle et al derivatives lack the instant dihydropyridine⇌pyridinium salt redox system and thus would not be capable of providing sustained brain delivery via a "locked-in" quaternary form.

As yet another alternative in accord with the present invention, the carboxyl group can be protected by converting it to an amide, i.e. the —COOH group is converted to a —CONR$_f$R$_g$ group wherein R$_f$ and R$_g$ are as defined and exemplified above. Such amide groups are also intended to be encompassed by the expression "carboxyl protecting group" as used with formulas (I) and (II) herein, or similar expressions used herein in conjunction with peptides of partial structures (A) and (B).

Selection of an appropriate carboxyl protecting group will depend upon the reason for protection and the ultimate use of the protected product. For example, if the protecting group is intended to be present in a pharmaceutically useful peptide end product, it will be selected from those protecting groups described hereinabove which offer low toxicity and the desired degree of lipophilicity and rate of in vivo cleavage. On the other hand, if the protecting group is used solely for protection during synthesis, then only the usual synthetic requirements will generally apply.

Carboxyl protecting groups for use in peptide synthesis are well-known to those skilled in the art. See, for example, M. Bodanszky, Principles of Peptide Synthesis, Springer-Verlag, New York 1984, Ives U.S. Pat. No. 4,619,915 and the various publications on peptide chemistry referred to in the Ives patent. See also Methoden der Organischen Chemie, Houben-Weyl, Volume 15/1 for protecting groups and Volume 15/2 for methods of peptide synthesis. Representative carboxyl protecting groups for synthetic purposes include various silyl esters (e.g. trialkylsilyl and trihalosilyl esters), alkyl esters (e.g. tert-butyl esters), benzyl esters and the other carboxyl protecting groups mentioned in the Ives patent. Simple alkyl esters are frequently satisfactory for synthetic purposes, while bulkier and more complex ester groupings (e.g. those of the polycycloalkyl and polycycloalkenyl, such as the sterol, residue types) or amides are generally preferred for use in vivo.

The expression "amino protective group" as used herein is intended to designate a group (T) which is inserted in place of a hydrogen atom of an amino group or groups in order to protect the amino group(s) during synthesis and/or to improve lipoidal characteristics and prevent premature metabolism of said amino group or groups prior to the compound's reaching the desired site in the body.

As with the carboxyl protecting groups, selection of a suitable amino protecting group will depend upon the reason for protection and the ultimate use of the protected product. When the protecting group is used solely for protection during synthesis, then a conventional amino protecting group may be employed. Appropriate amino protecting groups are known in the art and are described, for example, in the Bodanszky, Ives and Houben-Weyl references cited above. Representative amino protecting groups for synthetic use include acyl groups such as tert-butoxycarbonyl, benzyloxycarbonyl, benzoyl, acetyl and the like. Yet other conventional amino protecting groups for use in synthesis are described in the literature, e.g. in the Bodanszky publication and Ives patent referred to hereinabove.

As with the carboxyl protecting groups, when the amino protecting group is intended to be present in a pharmaceutically useful peptide end product, then it will be selected from among amino protecting groups which offer low toxicity and the desired degree of lipophilicity and rate of in vivo cleavage. Especially suitable for in vivo use as amino protecting groups T are activated carbamates, i.e. the protecting group T has the structure

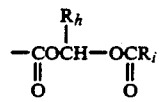

wherein R$_h$ is hydrogen, C$_1$–C$_7$ alkyl or phenyl and R$_i$ can be selected from the groups indicated as suitable carboxyl protecting groups W hereinabove. Again, the bulkier groups are preferred for use in vivo, and R$_i$ is preferably a polycycloalkyl or polycycloalkenyl-containing group, such as adamantyl or a sterol residue, especially a cholesterol or bile acid residue.

Alternatively, the amino protecting group T may simply be composed of one or two "throw away" natural amino acids, e.g. alanine or phenylalanine, which are not needed for activity but which are designed to be cleaved first from the rest of the molecule by a specific peptidase and in this way prevent premature degradation of the active portion of the molecule.

The various protecting groups for hydroxyl, carboxyl and amino functions discussed above can be substituted for the hydroxyl, carboxyl and amino functions in the instant amino acids/peptides (or their precursor molecules) by methods well-known in the art. Methods for chemical removal of the protecting groups (when such are not to be retained in the pharmaceutically useful end product) are likewise well-known to those skilled in the art. Typically, amine protecting groups are chemically removed by acidolysis (acid hydrolysis) or hydrogenation, depending on the particular protecting group employed. Hydroxyl and carboxyl protecting groups are typically removed chemically by acid or base hydrolysis. Protecting groups which are incorporated in the pharmaceutical end product must be amenable to hydrolytic or metabolic cleavage in vivo.

In general, the peptides provided by the present invention are prepared by sequential addition of one or more amino acids or protected amino acids, with the redox system being either first incorporated into an amino acid or protected amino acid which is then added to the growing peptide chain, or else inserted directly into a dipeptide or larger peptide fragement in the course of the peptide synthesis. Methods for sequential addition of amino acids to form peptides, utilizing protecting groups where appropriate, are well-known in the art. An excellent summary of such methods, including both solid phase synthesis and synthesis in solution, is contained in Nestor et al U.S. Pat. No. 4,530,920, which is incorporated by reference herein in its entirety and relied upon. See also SOLID PHASE PEPTIDE SYNTHESIS, second edition, John Morrow Stewart and Janis Dillaha Young, Pierce Chemical Company, Rockford, Ill., 1984.

Peptides provided by the present invention can also be prepared by segment condensation methods described in the literature, e.g. in the Bodanszky and Houben-Weyl references cited above.

The quaternary forms of the redox amino acids and peptides of this invention, i.e. the salts of formulas (II) and (B), respectively, can be prepared by a variety of methods suitably combined with the protection/deprotection and peptide linkage steps referred to above. Typical methods of combining the various steps are illustrated in the synthetic examples hereinafter. At the present time, three general methods have been found to be particularly convenient for preparation of the quaternary derivatives. Selection of an appropriate method depends upon the identities of Z and $R_1$ in the desired products of formulas (II) and (B).

The first of the three methods for preparing the quaternary salts is a halogen replacement reaction which is useful when Z in the desired product of formula (II) or (B) is to be attached to the heterocyclic ring via a ring nitrogen atom and $R_1$ is a direct bond. According to this method, a halogen-containing amino acid or peptide of the formula

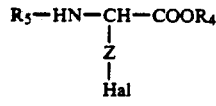

(III)

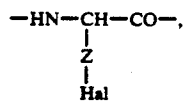

(C)

respectively, wherein Hal is chloro or bromo and $R_4$, $R_5$ and Z are defined as before, is reacted with a compound of the formula

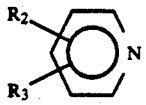

(IV)

wherein $R_2$ and $R_3$ are defined as before. Preferred starting materials of formula (IV) include nicotinamide, picolinamide, isonicotinamide, 3-quinolinecarboxamide and 4-isoquinolinecarboxamide. The reaction is typically carried out in an inert organic solvent, with heating. The products of formulas (II) and (B) are of the type in which Z is attached to the heterocyclic ring via a ring nitrogen atom, $R_1$ is a direct bond and $X^-$ is a chloride or bromide anion.

The second of the three methods found useful in preparing the quaternary salts of this invention is an alkylation reaction and can be used to prepare derivatives of formulas (II) and (B) wherein Z is attached to the heterocyclic ring via a ring carbon atom and $R_1$ is $C_1$-$C_7$ alkyl, $C_1$-$C_7$ haloalkyl or $C_7$-$C_{12}$ aralkyl. In accord with this method, an amino acid or peptide of the formula

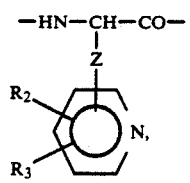

(V)

or

(D)

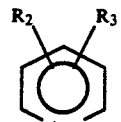

respectively, wherein $R_2$, $R_3$, $R_4$ and $R_5$ and Z are defined as before and Z is attached to the heterocyclic ring via a ring carbon atom, is reacted with an alkylating agent of the formula $R_1$-halide            (VI)

wherein $R_1$ is $C_1$-$C_7$ alkyl, $C_{1-C7}$ haloalkyl or $C_{7-C12}$ aralkyl and the halide is iodide, bromide or chloride. A preferred starting material of formula (VI) is methyl iodide. Typically, this quaternization reaction takes place in a suitable organic solvent. The products of formulas (II) and (B) are of the type in which Z is attached to the heterocyclic ring via a ring carbon atom, $R_1$ is $C_1$-$C_7$ alkyl, $C_1$-$C_7$ haloalkyl or $C_{7-C12}$ aralkyl and $X^-$ is an iodide, bromide or chloride ion.

The third method for preparing the quaternary salts is a Zincke exchange reaction useful when Z in the desired product of formula (II) or (B) is to be attached to the heterocyclic ring via a ring nitrogen atom and $R_1$ is a direct bond. Thus, a Zincke reagent of the formula

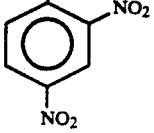

(VII)

wherein $R_2$ and $R_3$ are defined as before is reacted with an amino acid or peptide having a pendant primary amino group, i.e. an amino acid/peptide of the formula

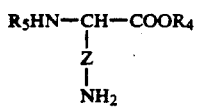  (VIII)

or

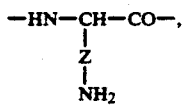  (E)

respectively, wherein R4, R5 and Z are defined as before. This reaction is generally conducted in the presence of a suitable base, e.g. triethylamine, in an appropriate organic solvent, e.g. methanol, and affords derivatives of formulas (II) and (B) wherein Z is attached to the heterocyclic ring via a ring nitrogen atom, R1 is a direct bond and X− is a chloride anion. The Zincke reagent employed in the process can be prepared by reacting 1-chloro-2,4-dinitrobenzene with a compound of formula (IV) above. Preferred Zincke reagents are those produced from nicotinamide, picolinamide, isonicotinamide, 3-quinolinecarboxamide and 4-isoquinolinecarboxamide. See also Zincke et al, Annalen, 1904, 333, 296; Lettré, Annalen, 1953, 579, 123; Keijzer et al, Heterocycles, Vol. 16, No. 10, 1981, 1687.

The various starting materials employed in the processes described above are commercially available or can be prepared by known methods.

When an anion is desired which is different from the one obtained by one of the processes described above, the anion in the quaternary salt of formula (II) or (B) may be subjected to anion exchange via an anion exchange resin or, more conveniently, by use of the method of Kaminski et al, Tetrahedron, Vol. 34, pp. 2857-2859 (1978). According to the Kaminski et al method, a methanolic solution of an HX acid will react with a quaternary ammonium halide to produce the methyl halide and the quaternary .X salt.

The quaternary salts of formulas (II) and (B) can be reduced to form the corresponding dihydro derivatives of formulas (I) and (A), respectively. Also, the quaternary salts of formulas (II) and (B) may be subjected to lengthening of the peptide chain, with reduction occurring at a later point in the synthetic scheme. Frequently, it may be desirable to postpone reduction until the peptide chain has reached the desired length, i.e. the length desired for the pharmaceutical end product.

Reduction of the quaternary salts of formulas (II) and (B) to the corresponding dihydro derivatives of formulas (I) and (A), respectively, is usually conducted at a temperature from about −10° C. to room temperature, for a period of time from about 10 minutes to 3 hours, conveniently at atmospheric pressure. The process is conducted in the presence of a suitable reducing agent, preferably an alkali metal dithionite such as sodium dithionite, an alkali metal borohydride such as sodium borohydride or lithium aluminum borohydride, or a more reactive dihydropyridine such as 1-benzyl-1,2-dihydroisonicotinamide.

Sodium dithionite reduction is conveniently carried out in an aqueous solution, e.g. aqueous methylene chloride, in the presence of base, e.g. sodium bicarbonate, and, in the case of pyridinium and quinolinium starting materials, generally affords a preponderance of 1,4-dihydro isomer. The dihydro product is usually insoluble in water and thus can be readily separated from the sodium dithionite reaction medium.

In the case of sodium borohydride reduction, an organic reaction medium is typically employed, e.g. a lower alkanol such as methanol, an aqueous alkanol or other protic solvent. For pyridinium and quinolinium starting materials, sodium borohydride reduction typically affords a preponderance of the 1,6-dihydropyridine and 1,2-dihydroquinoline isomers, respectively.

Other useful reducing agents include dihydropyridines which are more reactive than the quaternary salts which are to be reduced. A particularly suitable reagent of this type is the highly reactive 1-benzyl-1,2-dihydroisonicotinamide, which can be used for selective reduction of the quaternary salts by a direct hydride transfer reaction under neutral conditions [Nuvole et al, J. Chem. Research, 1984, (S), 356]. Thus, for example, pyridinium and quinolinium salts of the invention can be regioselectively reduced to the corresponding 1,4-dihydropyridines and 1,4-dihydroquinolines, respectively, utilizing 1-benzyl-1,2-dihydroisonicotinamide as the reducing agent, typically in a suitable organic reaction medium, e.g. anhydrous methanol. Other possible reducing agents of the reactive dihydropyridine type include ribosyl N-methyl dihydronicotinamide (derived from NADH).

Especially preferred compounds of the present invention are the amino acids of formula (I) in which the

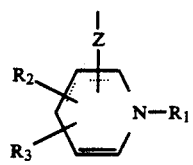

portion of the molecule has one of the following structures, as well as the corresponding peptides of formula (A) and the quaternary forms of these amino acids and dipeptides:

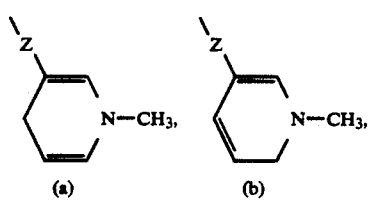

(a)     (b)

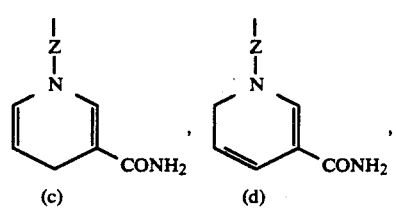

(c)     (d)

-continued
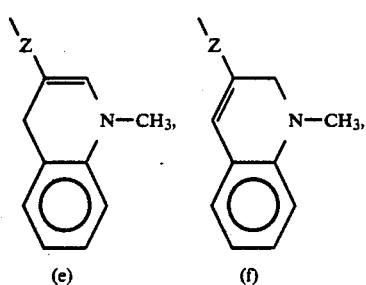
(e) (f)
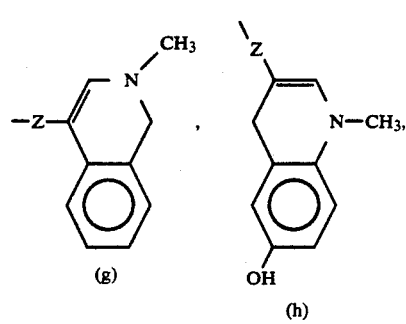
(g) (h)
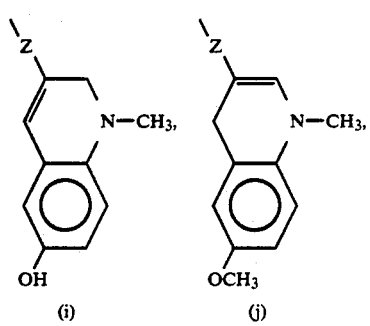
(i) (j)
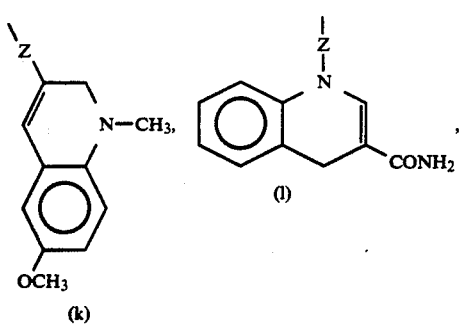
(k) (l)
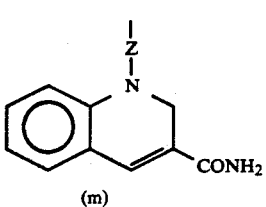
(m)
and
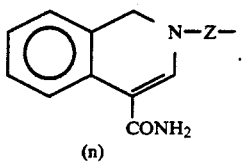
(n)
In the above structures, Z is preferable —CH$_2$— or —(CH$_2$)$_4$—. In structures (e), (f), (g), (h), (i), (j) and (k), Z is most preferably —(CH$_2$)—; in structures (c), (d), (l), (m) and (n), Z is most preferably —(CH$_2$)$_4$—. The corresponding quaternary salts of formula (II) have the partial structures:
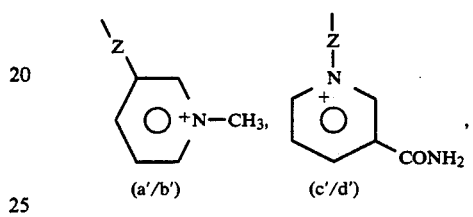
(a'/b') (c'/d')
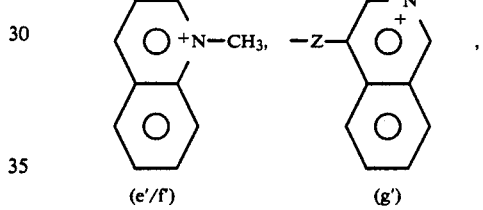
(e'/f') (g')
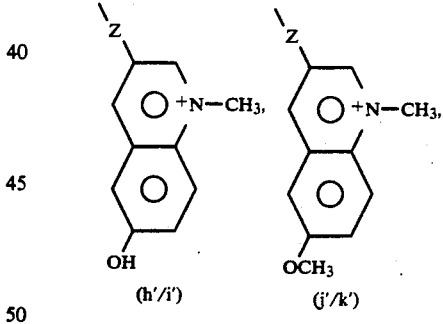
(h'/i') (j'/k')
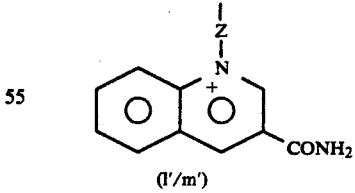
(l'/m')
and
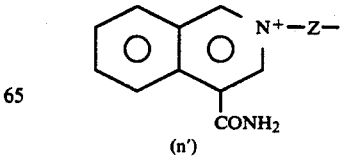
(n')

wherein Z is preferably as defined in the preceding two sentences.

As stated hereinabove, the novel amino acids of formulas (I) and (II) are useful in the preparation of novel bioactive peptides of the partial structural formulas (A) and (B). In particular, by incorporating an amino acid fragment of structure (A) or (B) into the peptide chain, there is provided herein a method for imparting improved brain specificity and substained in-brain activity to a pharmacologically active peptide. The peptide thus modified is susceptible to administration to a mammal in its reduced form comprising fragment (A) and is capable of in-brain conversion to its oxidized form comprising fragment (B). The oxidized form either is itself pharmacologically active or is convertible in vivo to a pharmacologically active form, e.g. by cleavage of one or more amino acid units. For most successful use in vivo, there are further incorporated into the final peptide (i.e. the peptide which is intended for administration) amino and carboxyl protective groups for the terminal amino and carboxyl functions of the peptide, the protective groups being capable of in-brain cleavage to free amino and carboxyl functions. Suitable such protective groups are discussed hereinabove. The amino acid fragment of structure (A) or (B) is preferably located in a non-terminal position of the peptide chain; nevertheless, terminal positions are contemplated as well. Moreover, more than one redox fragment may be incorporated into a given peptide; multiple such fragments may be particularly desirable in the case of larger peptides and/or when a peptide contains a plurality of suitable sites at which to introduce the redox fragment i.e. a plurality of locations at which the redox fragment can be placed without loss of the peptide's pharmacological activity.

The final redox peptide of the invention preferably contains a total of 2 to 20 amino acid units. Typically, except for the presence of at least one redox amino acid fragment of structure (A) or (B) and the possible protection of terminal amino and carboxyl functions, the structure of the instant redox peptide is identical to that of a known, naturally occurring bioactive peptide or of a known bioactive synthetic peptide (particularly one which is an analog of a naturally occurring bioactive peptide). Naturally, in order for the final redox peptide's brain specificity/sustained activity to be of value, the peptide must exert a useful central activity, i.e. it should exert a significant pharmacological action in the central nervous system such that it may be used as a drug, that is, for the diagnosis, cure, mitigation, treatment or prevention of disease or in the enhancement of desirable physical or mental development and conditions in man or animals, or it must be convertible in vivo to a peptide having a useful central activity.

Appropriate known peptides for incorporation of the instant redox system therein include naturally occurring peptides such as kyotorphin, met$^5$-enkephalin, leu$^5$-enkephalin, vasopressin, oxytocin, neurotensin, ACTH fragments, peptide T, Substance P, angiotensin, somatostatin and LH-RH, as well as their biologically active synthetic analogs.

Many of these peptides and their analogs have been previously studied in depth, so that it is possible to learn from the scientific literature which positions in the amino acid sequence are fairly critical to the requisite biological activity of a given peptide and which positions may be varied without loss of activity. Some of these teachings of the art and their application to the instant invention are discussed below, but this discussion is not intended to be exhaustive. In this discussion, the conventional peptide representation (amino terminus on left, carboxyl terminus on right) will be used, as will the conventional abbreviations for the individual amino acid units (Phe for phenylalanine, Gly for glycine, etc.). Insofar as concerns configuration, in this general discussion the configuration of optically active amino acids will be assumed to be L unless otherwise specified.

Kyotorphin is a dipeptide of the structure H-Tyr-Arg-OH which has analgesic properties. It has been found to stimulate the release of enkephalin. The corresponding dipeptides in which one or both amino acids has/have the D-configuration also have activity.

The enkephalins are two naturally occurring pentapeptides belonging to the endorphin class. Met$^5$-enkephalin has the structure

H-Tyr-Gly-Gly-Phe-Met-OH while Leu$^5$-enkephalin has the structure

H-Tyr-Gly-Gly-Phe-Leu-OH.

The most important property of the enkephalins is their morphine-like analgesic action. They also have a variety of effects on memory.

Some peptides slightly larger than the enkephalins with intrinsic opiate activity have also been identified. These include Met$^5$-enkephalin-Arg$^6$ and Met$^5$-enkephalin-Lys$^6$, which are believed to be potential precursors of Met$^5$-enkephalin; and Met$^5$-enkephalin-Arg$^6$-Phe$^7$, which has high affinity for K-opiate receptors.

Moreover, many enkephalin analogs have been synthesized (e.g. FK-33-824, LY 127623/metkephamid, Wy-42,896) and structure/activity relationships have been analyzed. See, in particular, J. S. Morley, Annu. Rev. Pharmacol. 20: 81-110 (1980), incorporated by reference herein in its entirety and relied upon. While virtually every position in the enkephalin chain allows some variation without loss of activity, some positions allow much more variation than others. Thus, in the case of N-terminal substitution, activity can be maintained in the same range by addition of an L-amino acid. The Gly$^2$ position appears to be particularly amenable to variation, and replacement with a D-amino acid often has been found to lead to a marked increase in potency and/or longer biological half-life. Also, structural/conformational changes at the Met$^5$/Leu$^5$ position, i.e. replacing Met$^5$ or Leu$^5$ with a different amino acid (L or D), have afforded analogs which are invariably active, although increases in potency as the result of such changes are modest. Replacement of the terminal acid function with an unsubstituted amide group has afforded a very potent analog, Met$^5$-enkephalin-NH$_2$. In addition, contraction or extension at the C-terminus has afforded active analogs.

Vasopressin and oxytocin are cyclic peptides which differ from each other in only two amino acids. All mammalian oxytocin (OXT) has the structure

Cys—Tyr—Ile—Gln—Asn—Cys—Pro—Leu—Gly—NH$_2$.

Most vasopressin is arginine-vasopressin (AVP), which has the structure

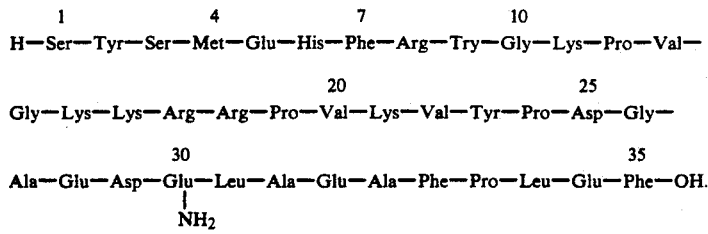

behavioral effects. Human ACTH$_{1-39}$ has the structure:

```
     1                 4              7             10
H—Ser—Tyr—Ser—Met—Glu—His—Phe—Arg—Try—Gly—Lys—Pro—Val—
                              20              25
Gly—Lys—Lys—Arg—Arg—Pro—Val—Lys—Val—Tyr—Pro—Asp—Gly—
             30                                    35
Ala—Glu—Asp—Glu—Leu—Ala—Glu—Ala—Phe—Pro—Leu—Glu—Phe—OH.
             |
             NH$_2$
``` swine vasopressin (SVP) is also known as lysine-vasopressin and has the structure

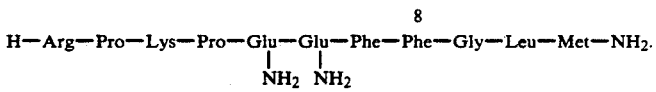

Vasopressin appears to enhance retention of learned responses and to enhance attention and memory. Both oxytocin and vasopressin may be involved in pain mechanisms. In vasopressin, residues 2, 3 and 5 seem to be fairly critical for activity, especially asparagine at 5. Most of the activity in vasopressin and oxytocin seems to be in the covalent ring structure. Removing the C-terminal glycinamide appears not to affect behavior. Behaviorally active fragments include H-Pro-Arg-Gly-NH$_2$, H-Lys-Gly-NH$_2$, AVP$_{1-7}$ (pressinamide), OXT$_{1-8}$, OXT$_{1-7}$, OXT$_{1-6}$, Pro-Leu-Gly-NH$_2$ and Leu-Gly-NH$_2$. While the amino acids at 8 and 9 can be removed, shortening to 6 or 7 amino acids appears to cause a change in activity, at least in the case of oxytocin, where OXT$_{1-7}$ and OXT$_{1-6}$ affect memory differently from OXT.

Neurotensin (NT) is a basic tridecapeptide of the formula p-Glu-Leu-Tyr-Glu-Asn-Lys-Pro-Arg-Arg-Pro-Tyr-Ile-Leu-OH which has a variety of hormone-like activities. It has been shown to induce hypotension. It also acts as a CNS neurotransmitter and appears to be a very potent analgesic. The carboxy terminal leucine moiety appears to be essential for binding and the arginine residues at 8 and 9 also are essential for binding and biological activity. Very little variation as positions 11, 12 and 13 seems to be possible. Xenopsin, an octapeptide which shares many properties with neurotensin, has the structure pGlu-Gly-Lys-Arg-Pro-Trp-Ile-Leu-OH.

Other potent neurotensin analogs include D-Tyr$^{11}$-NT and D-Phe$^{11}$-NT.

ACTH, or adrenocorticotropic hormone, has complex behavioral activities involving learning, memory, motivation, arousal and attention. It has 39 amino acids, but its essential structure is believed to be ACTH4-7, with phenylalanine in position 7 playing a key role in Active fragments include ACTH$_{4-10}$ and ACTH$_{4-7}$, with ACTH$_{4-7}$ being the shortest peptide found to give the typical behavioral effects of ACTH. A very active ACTH$_{4-9}$ analog, OGR 2766, has the structure H-Met(O)-Glu-His-Phe-D-Lys-Phe-OH, which has an oxidized methionine at 4, D-lysine at 8 in place of arginine, and phenylalanine at 9 in place of tryptophan. It shows 1000 fold potentiation, with dissociation of behavioral effects from endocrine, metabolic and opiate-like activities. Other active analogs include D-Phe$^7$-ACTH$_{1-10}$, D-Phe$^7$-ACTH$_{4-7}$ and D-Phe$^7$-ACTH$_{4-10}$, although in some ways these analogs behave oppositely from the natural L-forms.

Peptide T is an octapeptide with anti-AIDS activity. Substance P is an undecapeptide which acts as a vasodilator and a depressant, and can produce analgesia and hyperalgesia. It plays an important role in nervous system function. Substance P has the structure

```
                              8
H—Arg—Pro—Lys—Pro—Glu—Glu—Phe—Phe—Gly—Leu—Met—NH$_2$.
                  |   |
                  NH$_2$ NH$_2$
```

It appears that most structural variation can occur at positions 1 to 6, with some variation also possible at 8. Active analogs include physalaemin, which has the structure pGlu-Ala-Asp-Pro-Asn-Lys-Phe-Tyr-Gly-Leu-Met-NH$_2$;

eledoisin, which has the structure pGlu-Pro-Ser-Lys-Asp-Ala-Phe-Ile-Gly-Leu-Met-NH$_2$;

and kossinin, which has the structure

Asp-Val-Pro-Lys-Ser-Asp-Gln-Phe-Val-Gly-Leu-Met-NH$_2$.

Moreover, a series of retro-inverso C-terminal hexapeptide analogs of Substance P has been recently described by Verdini et al, U.S. Pat. No. 4,638,046, dated Jan. 20, 1987, incorporated by reference herein and relied upon. Verdini et al describe compounds of the formula

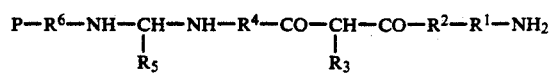

in which P is a hydrogen atom, a linear or branched aliphatic alkyl group with 1-6 carbon atoms, or a saturated or unsaturated linear or branched chain aliphatic acyl group such as formyl, acetyl, propionyl, n-butyryl, isobutyryl, n-valeryl, isovaleryl, hexanoyl, isohexanoyl, heptanoyl, octanoyl, crotonoyl, methacryloyl, acryloyl; or a substituted acyl group such as hydroxyacetyl, 2-hydroxypropionyl, 3-hydroxypropionyl, aminoacetyl, 4-hydroxyphenylacetyl, 4-hydroxyphenylpropionyl, 2-aminopropionyl, 3-aminopropionyl, 0-ethylmalonyl, ethoxyformyl, methoxyacetyl, 3-methoxypropionyl, 3-ethoxypropionyl, chloroacetyl, dichloroacetyl, 2-chloropropionyl, 3-chloropropionyl, 2,3-dichloropropionyl, bromoacetyl, 4-hydroxy-3,5-diiodophenylacetyl, 3-oxobutyryl, 3-oxovaleryl, 4-oxovaleryl, methylthioacetyl, 3-methylthiopropionyl, ethylthioacetyl, 3-ethylthiopropionyl, nicotinoyl, 4-aminobutyryl, $N^\alpha$-[(1-(9-adenyl)$\beta$-D-ribofuranuronosyl)], $N^\alpha$-[(1-(9-hypoxanthyl)-$\beta$-D-ribofuranuronosyl]; or a group such as benzyloxycarbonyl, tert-butyloxycarbonyl, tert-amyloxycarbonyl, isobornyloxycarbonyl, adamantyloxycarbonyl, or chloro or nitro-substituted benzyloxycarbonyl;

$R^1$ is a residue of methionine, methionine sulphoxide, methionine sulphone, selenomethionine, leucine, norleucine, valine or norvaline;

$R^2$ is a residue of leucine, norleucine, valine, norvaline, alanine or isoleucine;

$R^3$ is a hydrogen atom or methyl;

$R^4$ is an amino acid residue of D configuration such as phenylalanine, tryptophan, tyrosine, valine, norvaline, leucine, norleucine, isoleucine, serine or derivatives, threonine or derivatives, histidine or derivatives, methionine, methionine-S-methyl, methionine sulphone, arginine or derivatives, lysine or derivatives, ornithine or derivatives, 2,4-diaminobutyric acid or derivatives, 2,3-diaminopropionic acid or derivatives, glutamic acid or aspartic acid or their suitable derivatives;

$R^5$ is a hydrogen atom or the side-chain of amino acids such as phenylalanine, tyrosine, 4-chlorophenylalanine, 0-benzyltyrosine (or their acetyl, cyclopentyl, tert-butyloxycarbonyl or 4-hydroxyphenylacetyl derivatives);

$R^6$ is an amino acid residue such as glutamine or derivatives, pyroglutamic acid, alanine, tyrosine, lysine or derivatives, proline, N-formyl-proline, $\beta$-alanine, N-acetyl-$\beta$-alanine, glycine, desaminophenylalanine, desaminoaspartic acid, methyldesaminoaspartic acid, or glutamic acid esters represented by the general formula

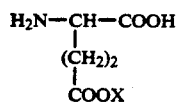

in which X is methyl, ethyl, methoxyethyl or methoxy(ethoxy)nethyl wherein n=1, 2 or 3.

The Verdini et al analogs show variations possible in the amino acids corresponding to positions 6, 7 and 9-11 of Substance P, substantial variations at position 8 of Substance P ($R^4$ of Verdini et al) using a wide variety of D amino acid residues, and the ability to delete the first five amino acids in Substance P without loss of activity.

A group of biologically active heptapeptides has been recently described by deCastiglione et al, U.S. Pat. No. 4,567,162, dated Jan. 28, 1986, incorporated by reference herein and relied upon. These peptides are said to display activity on the central nervous system and to be useful in promoting growth activity and improving feed efficiency in animals. The compounds have the general formula

wherein:

X represents a hydrogen atom or a terminal nitrogen protecting group of acyl, aliphatic urethane, aromatic urethane, alkyl or aralkyl type;

A represents a neutral L-$\alpha$-amino acid residue; and

Y represents a hydroxy group, an amino group or a group of the formula OR, NHR, $NR_2$ or NH—N—H—R' wherein R represents a straight chain, branched chain or cyclic (including fused or bridged rings) alkyl group having up to 11 carbon atoms which may be unsubstituted or independently substituted by a hydroxy or amino group or a halogen atom, an aralkyl group having from 7 to 14 carbon atoms or a phenyl group; and R' represents a hydrogen atom, any of the groups which R may represent, a straight chain, branched chain or cyclic aliphatic acyl group having from 1 to 11 carbon atoms which may be unsubstituted or independently substituted by a hydroxy or an amino group or a halogen atom, an aromatic acyl group which may be unsubstituted or independently substituted by a hydroxy or amino group or a halogen atom, a straight chain, branched chain or cyclic aliphatic urethane type group having from 3 to 11 carbon atoms, or an aromatic urethane type group. Thus, a significant amount of variation is possible in the structure of the seventh, or terminal amino acid, A.

Angiotensin is a pressor substance. Angiotensin I, a decapeptide, is converted to the active pressor agent, angiotensin II, by splitting off the C-terminal His-Leu residues. The octapeptide II differs among species at position 5 (Val or Ile). The active angiotensin II as well as angiotensin amide are hypotensive and may increase the effectiveness of endogenous norepinephrine. These peptides have the following structures:

Angiotensin I:
Asp—Arg—Val—Tyr—Ile—His—Pro—Phe—His—Leu

Angiotensin II:
Asp—Arg—Val—Tyr—Ile—His—Pro—Phe

Angiotensin Amide:
Asp—Arg—Val—Tyr—Ile—His—Pro—Phe.
|
$NH_2$

Thus, it would appear that at least the C-terminal dipeptide portion of Angiotensin I could be modified without loss of activity.

Somatostatin (SRIF) is a cyclic tetradecapeptide that with GRF mediates the neuroregulation of pituitary growth hormone release. It is also a potent inhibitor of central and peripheral neural systems. It has been used as an experimental hypoglycemic and growth hormone inhibitor. Somatostatin has the formula

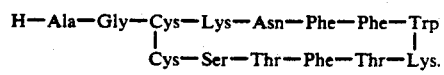

Potent peptides having an N-terminal extension of SRIF-14 have also been isolated. It is believed that modification of the non-cyclic portion of somatostatin, by replacing part or all of the N-terminal dipeptide or by adding to the N-terminus, can be undertaken without loss of activity.

LH-RH, or GnRH, is the luteinizing hormone-releasing factor. It is the neurohumoral hormone produced in the hypothalamus which stimulates secretion of LH and FSH, which in turn regulate functioning of the gonads (by stimulating production of steroid hormones) and regulate gamete production and maturation. LH-RH is a decapeptide having the structural formula

p-Glu-His-Trp-Ser-Tyr-Gly-Leu-Arg-Pro-Gly-NH$_2$.

Agonist analogs of LH-RH may be used to control fertility in two different ways. Thus, low doses of LH-RH analogs can be used to stimulate ovulation in the female as well as spermatogenesis and androgen production in the male. Larger doses of LH-RH analogs, especially long-acting, highly potent analogs, paradoxically block ovulation and suppress spermatogenesis. In domestic animals, the latter effect promotes weight gain and generally acts as a sterilant. Antagonist analogs of LH-RH, i.e. analogs which are antagonistic to the normal function of LH-RH, may be used as male or female contraceptives, in the treatment of endometriosis and precocious puberty in females and in the treatment of prostatic hypertrophy in males. Basically, the antagonist analogs are used to inhibit the production of gonadotropins and sex hormones, which is essentially the same as the high dose, paradoxical effect of the agonist analogs.

It is now well-known that the glycine residue in the 6-position of LH-RH can be replaced by a variety of D-amino acids to give LH-RH agonists and antagonists of much greater potency than the natural hormone itself. Other changes which have resulted in substantial increase or retention of activity include eliminating Gly-NH$_2$ at the 10-position to give a nonapeptide as an alkyl-, cycloalkyl- or fluoroalkylamide; replacing Gly-NH$_2$ at the 10-position with an α-azaglycine amide; replacing Leu at the 7-position with N-methyl-leucine; replacing Trp at the 3-position with 3-(1-naphthyl)-L-alanyl or with 3-(2-naphthyl)-L-alanyl; and replacing Tyr at the 5-position with phenylalanyl or with 3-(1-pentafluorophenyl)-L-alanyl.

Numerous LH-RH analogs, most frequently nonapeptides and decapeptides, have been developed to date. For example, Nestor et al, U.S. Pat. No. 4,530,920, dated July 23, 1985, incorporated by reference herein in its entirety and relied upon, provides nonapeptide and decapeptide agonist analogs of LH-RH which have the formula

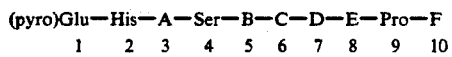

(pyro)Glu—His—A—Ser—B—C—D—E—Pro—F
   1     2   3   4   5  6  7  8  9  10 and the pharmaceutically acceptable salts thereof, wherein:

A is tryptophyl, phenylalanyl, 3-(1-naphthyl)-L-alanyl or 3-(2-naphthyl)-L-alanyl;

B is tyrosyl, phenylalanyl or 3-(1-pentafluorophenyl)-L-alanyl;

C is an amino acyl residue selected from the group consisting of the radicals represented by the following structural formulas:

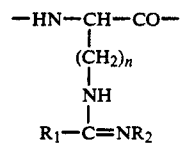
(a)

wherein n is 1 to 5;

R$_1$ is alkyl of 1 to 12 carbon atoms, —NRR$_3$ wherein R is hydrogen or alkyl of 1 to 4 carbon atoms, R$_3$ is hydrogen, alkyl of 1 to 12 carbon atoms, cycloalkyl, fluoroalkyl, phenyl, benzyl, —(CH$_2$)$_n$—morpholino or —(CH$_2$)$_n$N(R$_4$)$_2$ wherein n is 1 to 5 and R$_4$ is lower alkyl;

R$_2$ is hydrogen or R$_3$; or R$_1$ and R$_2$ comprise a ring represented by the following structural formulas:

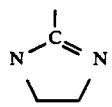

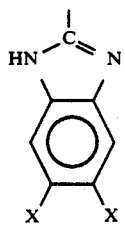

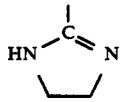

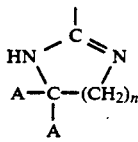

wherein n is 1 to 7; A is hydrogen, alkyl of 1 to 6 carbon atoms or cycloalkyl; and X is halo or A; or

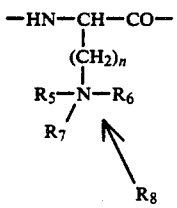
(b)

wherein R$_5$ is alkyl of 1 to 6 carbon atoms, benzyl, phenylethyl, cyclohexyl or cyclopentyl; R$_6$, R$_7$ and R$_8$ are hydrogen or alkyl of 1 to 4 carbon atoms; and n is the integer 2–5; or a substituent of the formula -continued

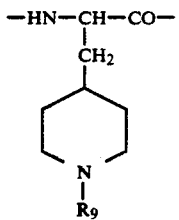

(c)

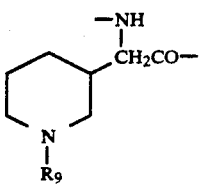

wherein $R_9$ is hydrogen, alkyl of 1 to 12 carbon atoms, phenyl or phenylloweralkyl:

D is leucyl, isoleucyl, nor-leucyl, N-methylleucyl or tryptophanyl;

E is arginyl or leucyl; and

F is glycinamide or —NH—$R^1$, wherein $R^1$ is lower alkyl, cycloalkyl, fluoro lower alkyl or —NH—CO—NH—$R^2$ wherein $R^2$ is hydrogen or lower alkyl.

Exemplary antagonist analogs of LH-RH are provided by Rivier et al U.S. Pat. No. 4,565,804, dated Jan. 21, 1986 and Rivier et al U.S. Pat. No. 4,569,927, dated Feb. 11, 1986, both incorporated by reference herein in their entirety and relied upon. The '804 peptides have the structure X-$R_1$-(W)D-Phe-$R_3$-$R_4$-$R_5$-$R_6$(V)-$R_7$-Arg-Pro-$R_{10}$ wherein X is hydrogen or an acyl group having 7 or less carbon atoms; $R_1$ is dehydro-Pro, Pro, D-pGlu, D-Phe, D-Trp or β-D-NAL; W is F, Cl, Cl$_2$Br, NO$_2$ or C$^\alpha$-MeCl; $R_3$ is D-Trp, (N$^{in}$For)D-Trp or D-Trp which is substituted in the 5- or 6-position with NO$_2$, NH$_2$, OCH$_3$, F, Cl, Br or CH$_3$; $R_4$ is Ser, Orn, AAL or aBu; $R_5$ is Tyr, (3F)Phe, (2F)Phe, (3I)Tyr, (3CH$_3$)Phe, (2CH$_3$)Phe, (3Cl)Phe or (2Cl)Phe; $R_6$ is D-Lys, D-Orn or D-Dap; V is arg-R', R")$_n$(X), with n being 1 to 5 and R' and R" being H, methyl, ethyl, propyl or butyl; $R_7$ is Leu, NML, Nle or Nva; and $R_{10}$ is Gly-NH$_2$, D-Ala-NH$_2$ or NH-Y, with Y being lower alkyl, cycloalkyl, fluoro lower alkyl or

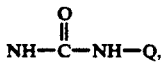

where Q is H or lower alkyl.

In the '804 peptides, the expression "β-D-NAL" means the D-isomer of alanine, substituted by naphthyl on the β-carbon, or 3-D-NAL. Preferably, the β-carbon is attached at the 2-position of naphthalene (β-D-2NAL), but β-D-INAL may also be used. "(C$^\alpha$Me-4Cl)Phe" means phenylalanine substituted at the para position with chloro, the α-carbon being methylated. "Dap" means α,β-diaminopropionic acid, or β-aminoalanine. "NML" means N$^\alpha$CH$_3$-L-Leu. "AAL" means β-amino-Ala or Dap, and "aBu" means β,γ-diaminobutyric acid, either of which or Orn may be present in the 4-position. DehydroPro is preferably at position 1 when Ser is not present at position 4. "$R_6$(arg-R',R")$_n$(X)" means the D-amino acid in the main chain, which through its side chain amino function also forms part of the arginine-containing peptide side chain.

The '927 peptides have the structure

X-$R_1$-(W)D-Phe-$R_3$-$R_4$-$R_5$-$R_6$-$R_7$-Arg-Pro-$R_{10}$ wherein X is hydrogen or an acyl group having 7 or less carbon atoms; $R_1$ is dehydro-Pro, D-pGlu, D-Phe, D-Trp or β-D-NAL; W is F, Cl, Cl$_2$Br, NO$_2$ or C$^\alpha$-MeCl; $R_3$ is (NinFor)D-Trp or D-Trp which is substituted in the 5-or 6-position with NO$_2$, NH$_2$, OCH$_3$, F, Cl, Br or CH$_3$; $R_4$ is Ser, Orn, AAL or aBu; $R_5$ is Tyr, Arg, (3F)Phe, (2F)Phe, (3I)Tyr, (3CH$_3$)Phe, (2CH$_3$)Phe, (3Cl)Phe or (2Cl)Phe; $R_6$ is A(4NH2)D-Phe, D-Lys, D-Orn, D-Har, D-His, (4gua)D-Phe, D-Tyr, a D-isomer of a lipophilic amino or D-Arg; $R_7$ is Leu, NML, Nle or Nva; and $R_{10}$ is Gly-NH$_2$, D-Ala-NH2 or NH-Y, with Y being lower alkyl, cycloalkyl, fluoro lower alkyl or

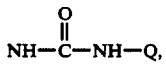

where Q is H or lower alkyl, provided however that when $R_5$ is Arg, $R_6$ is D-Tyr. The various terms are as defined with the '804 peptides.

It is clear from the Nestor et al and Rivier et al patents that the amino acid in the 6-position of the LH-RH peptide chain is very amenable to replacement by numerous D-amino acids, including unnatural amino acids which have sizeable side chains. These patents also confirm the extent of other permissible structural changes discussed hereinabove for LH-RH analogs, e.g. at the 3-, 5- and 7-positions.

It will be apparent from the foregoing that many peptides offer a multiplicity of locations at which a redox amino acid fragment of the present invention might be inserted without loss of the peptide's characteristic activity. Nevertheless, it is preferred that the redox system be located in a position which allows a great deal of structural variation without loss of activity and/or that the specific redox fragment selected be isosteric (or approximately so) with the amino acid unit which it is intended to replace. At the present time, the following redox amino acid fragments are preferred specific embodiments of this invention:

| REDOX AMINO ACID FRAGMENT | | ABBREVIATION |
|---|---|---|
|  | | Pyrala |

| REDOX AMINO ACID FRAGMENT | ABBREVIATION |
|---|---|
| 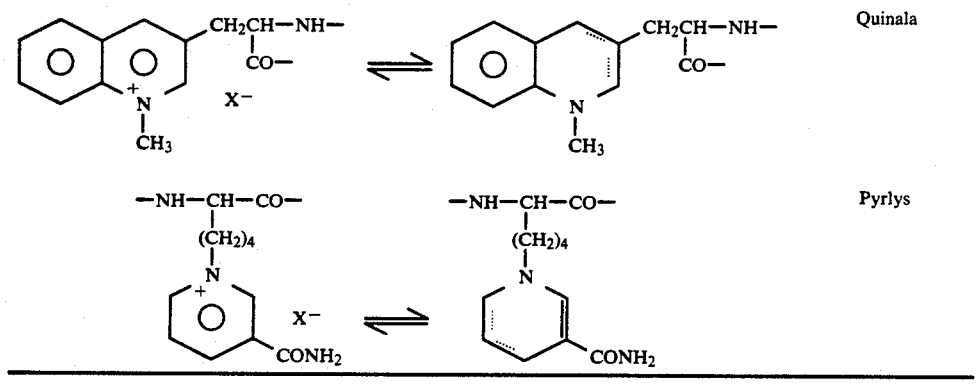 | Quinala |
| | Pyrlys |

However, it is to be understood that these particular redox fragments are intended to be illustrative, not limitative, of the instant fragments which may be incorporated into known centrally active peptides.

Some especially preferred embodiments of the present invention are the following:

(a) Enkephalin analogs of the structures

H-Tyr-(A/B)-Gly-Phe-Met-OH and

H-Tyr-(A/B)-Gly-Phe-Leu-OH and the corresponding terminal amino protected and terminal carboxyl protected compounds (including the corresponding C-terminal amides) in which the protecting groups are as defined hereinabove and (A/B) represents a redox amino acid fragment of structure (A) or (B) hereinabove, especially when (A/B) is Pyrala, Quinala or Pyrlys, having the L- or D-configuration;

(b) Enkephalin analogs of the structure

H-Tyr-Gly-Gly-Phe-(A/B)-OH and the protected counterparts as in (a) above, especially when (A/B) is Pyrala, Ouinala or Pyrlys, having the L- or D-configuration;

(c) Vasopressin and oxytocin analogs in which the amino acids at the 8- and/or 9-positions are replaced with L- or D-(A/B) as defined above, especially when (A/B) is Pyrala, Quinala or Pyrlys;

(d) Neurotensin analogs in which $Lys^6$ or $Tyr^{11}$ is replaced with L- or D-(A/B) above, and their C-terminal protected counterparts, especially those in which Pyrlys is in the 6-position or Pyrala is in the 11-position;

(e) $ACTH_{1-10}$, $ACTH_{4-7}$ and $ACTH_{4-10}$ analogs in which $Phe^7$ is replaced with D-(A/B), and their protected counterparts, especially when (A/B) is Pyrala;

(f) $ACTH_{4-9}$ analogs of the structures

H-Met(O)-Glu-His-Phe-D-(A/B)-Phe-OH and

H-Met(O)-Glu-His-Phe-D-Lys-(A/B)-OH and their protected counterparts, especially those of the first structure where D-(A/B) is D-Pyrlys and those of the second where (A/B) is Pyrala or Quinala;

(g) $ACTH_{1-10}$ wherein $Trp^9$ is replaced with (A/B) and its protected counterparts, especially when (A/B) is Pyrala or Quinala;

(h) $ACTH_{4-10}$ wherein $Arg^8$ is replaced with D-(A/B) and its protected counterparts, especially when (A/B) is Pyrala or Quinala;

(i) Substance P analogs in which $Phe^8$ is replaced with (A/B) and their N-terminal protected counterparts, especially when (A/B) is Pyrala;

(j) Substance P analogs in which any one of the amino acids at positions 1 to 6 is replaced with (A/B), and their N-terminal protected counterparts, especially when (A/B) is Pyrala, Ouinala or Pyrlys;

(k) Hexapeptide analogs of Substance P having the structure defined in Verdini et al U.S. Pat. No. 4,638,046 and set forth hereinabove, except that Verdini et al's $R^4$ amino acid residue is replaced with an amino acid fragment of the present invention D-(A/B), especially D-Pyrala, D-Quinala or D-Pyrlys;

(l) Heptapeptide analogs of the growth promoting peptides defined in deCastiglione et al U.S. Pat. No. 4,567,162 and set forth hereinabove, except that deCastiglione et al's amino acid unit A is replaced with an amino acid fragment of the present invention L-(A/B), especially L-Pyrala, L-Quinala or L-Pyrlys;

(m) Angiotensin I analogs in which one or both of the amino acids in the C-terminal dipeptide portion is replaced with (A/B), and the protected counterparts (especially the N-terminal amide), particularly when (A/B) is Pyrala, Quinala or Pyrlys;

(n) Somatostatin analogs in which (A/B) replaces part or all of the N-terminal dipeptide portion or in which (A/B) is added to the N-terminus, and the corresponding terminal amino protected derivatives, especially when (A/B) is Pyrala, Quinala or Pyrlys;

(o) LH-RH analogs having the structure defined in Nestor et al U.S. Pat. No. 4,530,920 and set forth hereinabove, except that Nestor et al's amino acid residue C in the 6-position is replaced with an amino acid fragment of the present invention (A/B), especially D-(A/B), where (A/B) is preferably Pyrala, Quinala or Pyrlys; and (p) LH-RH analogs of the structures depicted in the Rivier et al '804 and '927 patents and set forth hereinabove, except that Rivier et al's amino acid residue in the 6-position is replaced with an amino acid fragment of the present invention D-(A/B), especially when (A/B) is Pyrala, Quinala or Pyrlys.

In instances in which isosteric considerations are important, typically a fragment of the instant invention such as Pyrala will be used to replace phenylalanine or tyrosine, a fragment such as Quinala will be used to replace tryptophan and a fragment such as Pyrlys will be used to replace lysine, arginine or histidine in a peptide chain.

The methods for synthesizing the amino acids and peptides of the present invention have already been discussed hereinabove. In some cases, the methods of peptide synthesis can be simplified by utilizing commercially available bioactive peptides and their fragments. SIGMA ® CHEMICAL COMPANY, Post Office Box 14508, St. Louis, Mo. 63178 US has a large number of such products available; some of those which may be useful in preparing the instant redox peptides include, for example, angiotensin II, neurotensin fragment 1-6, neurotensin fragment 1-8, neurotensin fragment 8-13, somatostatin, Substance P fragment 1-4, Substance P fragment 4-11, Substance P fragment 5-11 and Substance P fragment 7-11.

In order to further illustrate the amino acids and peptides of the present invention, the following synthetic examples are given, it being understood that same are intended only as illustrative, as many modifications in materials and methods will be apparent to those skilled in the art.

In the examples to follow, all melting points were taken on a Mel-Temp apparatus and are not corrected. Elemental analyses were performed at Atlantic Microlabs, Inc., Atlanta, Ga.

EXAMPLE 1

Preparation of
N-(tert-Butoxycarbonyl)-3-chloro-L-alanine

To a solution of 1.0 g (6.25 mmol) of 3-chloro-L-alanine and 1.3 mL of triethylamine in 50% aqueous 1,4-dioxane were added 1.69 g (6.90 mmol) of 2-(tert-butoxycarbonyloxyimino)-2-phenylacetonitrile with stirring at room temperature. After 2 hours, the reaction mixture was poured into 20 mL of water and extracted twice with ethyl acetate. The organic layer was washed twice with water and then with saturated brine, dried over anhydrous magnesium sulfate and evaporated to give 0.66 g (40.5%) of white solid. Recrystallization from a mixture of ethyl acetate and n-hexane afforded 0.58 g of the pure product (35.6%) melting at 123°-124° C., with decomposition, and having the structural formula:

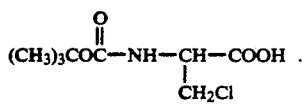

The identity of the product was confirmed by IR and NMR analyses.

EXAMPLE 2

Preparation of
N-(tert-Butoxycarbonyl)-3-chloro-L-ala-nylglycine ethyl ester

To a solution of 0.28 g (2 mmol) of glycine ethyl ester hydrochloride and 0.28 mL (2 mmol) of triethylamine in 10 mL of chloroform, 0.52 g (2 mmol) of N-(tert-butoxycarbonyl)-3-chloro-L-alanine in 6 mL of chloroform and 0.42 g (2 mmol) of dicyclohexylcarbodiimide were added at 0° C. The reaction mixture was stirred for 16 hours at room temperature. The resultant precipitate was removed by filtration and the filtrate was washed successively with 0.5N hydrochloric acid, water and 3% aqueous sodium bicarbonate, then was dried over anhydrous sodium sulfate. Removal of the solvent left a crystalline residue which was recrystallized from a mixture of ethyl acetate and n-hexane to give 0.415 g (60%) of the pure product melting at 71.5°-72.0° C. The identity of the product, which has the structural formula

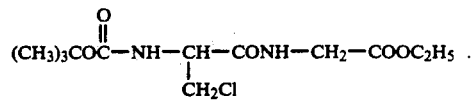

was confirmed by IR and NMR analyses.

EXAMPLE 3

Preparation of
L-1-[2-(tert-Butoxycarbonyl)amino-2-(N-ethoxycarbonylmethyl)carbamoyl]ethyl-3-carbamoylpyridinium chloride A solution of 0.11 g (0.32 mmol) of N-(tert-butoxycarbonyl)-3-chloro-L-alanylglycine ethyl ester and 47 mg (0.39 mmol) of nicotinamide in 2 mL of dry acetone was gently refluxed overnight. During reflux, acetone was removed by evaporation to leave a pale brown solid. This procedure was repeated three times. Then the well-dried solid was washed five times with 1 mL portions of dry acetone to give 50 mg (27.5%) of pale brown solid. Recrystallization from a mixture of methanol and acetonitrile gave 16 mg of pale brown crystals, melting at 223°-235° C. The identity of the product, which has the structural formula

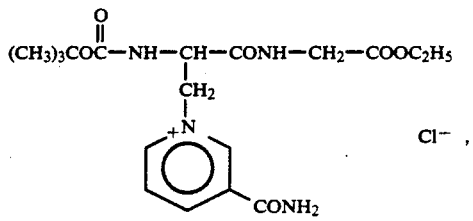

was further confirmed by IR analysis.

EXAMPLE 4

Preparation of
N-(tert-butoxycarbonyl)-3-chloro-L-alanyl-L-phenylalanyl-L-leucine ethyl ester To a solution of 0.42 g (1 mmol) of L-phenylalanyl-L-leucine ethyl ester trifluoroacetate, 0.14 mL (1 mmol) of triethylamine and 0.26 g (1 mmol) of N-(tert-butoxycarbonyl)-3-chloro-L-alanine in 8 mL of chloroform, 0.21 g (1 mmol) of dicyclohexylcarbodiimide was added at 0° C. The resultant reaction mixture was stirred overnight at room temperature. The precipitate which formed was removed by filtration and the filtrate was washed successively with 0.5N hydrochloric acid, water, 3% aqueous sodium bicarbonate and water, then dried over anhydrous sodium sulfate. Removal of the solvent afforded a white solid, which was mixed with 4 mL of a 1:1 mixture of ethyl acetate and n-hexane. Insoluble materials were removed by filtration and the filtrate was evaporated. The residue was recrystallized from a mixture of ethyl acetate and n-hexane to give 0.367 g (66.5%) of the desired product. The product, which has the structural formula

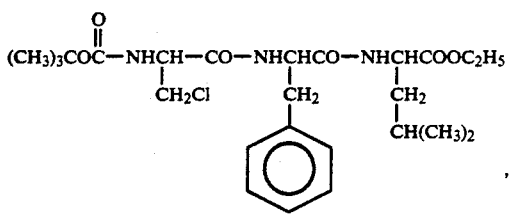

melted at about 110° C. Its identity was further confirmed by IR and NMR analyses and by thin layer chromatography ($R_f=0.34$ in 5:1 chloroform/ethyl acetate).

EXAMPLE 5

Preparation of N-Benzoyl-3-(3-quinolyl)alanine methyl ester

A mixture of 1.46 g (9.3 mmol) of 3-quinolinecarboxaldehyde, 1.8 g (10 mmol) of hippuric acid, 0.6 g (7.0 mmol) of anhydrous sodium acetate and 8 mL of acetic anhydride was heated gradually and stirred for 30 minutes at 90°-100° C. To the hot reaction mixture were added 10 mL of hot water. The reaction mixture was then allowed to cool to room temperature. The yellow solid which formed was removed by filtration, washed once with 50% aqueous acetic acid and twice with ethanol, then dried in vacuo to give 2.39 g of yellow solid melting at 200°-202° C. Recrystallization from a mixture of chloroform and ethyl acetate afforded 2.05 g (73.4%) of the pure azolactone melting at 209.5°-210° C. and having the structural formula:

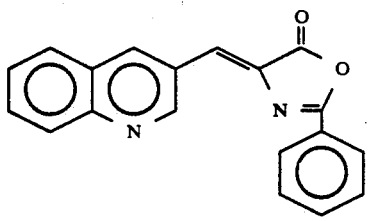

IR and NMR analyses confirmed the identity of the azolactone.

A mixture of 2.0 g (67 mmol) of the azolactone and 0.3 g of 10% palladium on carbon catalyst in 60 mL of acetic acid was vigorously stirred under hydrogen overnight. The catalyst was removed by filtration and washed thoroughly with dimethylformamide. The filtrate and washings were combined and concentrated. The residue was hydrogenated overnight using 0.3 g of 10% palladium on carbon as the catalyst. The catalyst was removed by filtration and the filtrate was evaporated to give a reddish brown solid. The solid was suspended in dry methanol; then, hydrogen chloride gas was passed through the suspension, with cooling in ice water, until saturation was reached. The reaction mixture was allowed to stand overnight, then was evaporated. The resultant residue was neutralized with a sufficient amount of aqueous sodium bicarbonate and extracted twice with chloroform. The combined organic layers were washed with water, dried over anhydrous sodium sulfate and concentrated under reduced pressure. The residue was chromatographed on silicon (IV) oxide, using 2% methanol in chloroform as eluent, to give 0.41 g of an oil which solidified on standing. Recrystallization from a mixture of ethyl acetate and isopropyl ether gave 0.25 g of pale brown crystals melting at 124°-125° C. The identity of the product, which has the structural formula

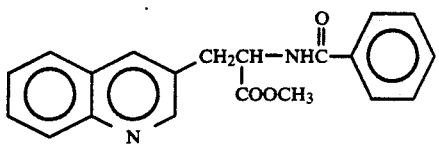

was confirmed by IR analysis.

EXAMPLE 6

Preparation of 3-(2-Benzoylamino-2-methoxycarbonyl)-ethyl-1-methylquinolinium iodide A solution of 0.21 g (0.63 mmol) of N-benzoyl-3-(3-quinolyl)alanine methyl ester and 1.0 mL of iodomethane in 5.0 mL of anhydrous acetone was refluxed overnight. The resulting precipitate was removed by filtration and recrystallized twice from a mixture of acetonitrile and acetone to give yellow crystals, which were dried in vacuo at 80° C. to afford 0.21 g (40%) of orange crystals melting at 110°-114° C. The product, which was further characterized by IR and NMR analyses, has the structural formula:

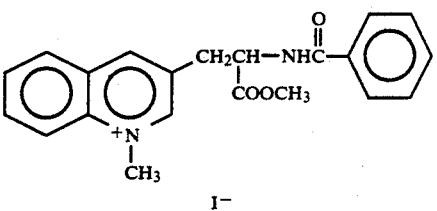

EXAMPLE 7

Preparation of N$^\epsilon$-Benzyloxycarbonyl-N$^\alpha$-(tert-butoxycarbonyl)-L-lysine methyl ester An ethyl ether solution of 1.48 g (3.9 mmol) of N$^\epsilon$-benzyloxycarbonyl-N$^\alpha$-(tert-butoxycarbonyl)-L-lysine was combined with an ethyl ether solution of diazomethane at 0° C. The reaction mixture was evaporated to give a colorless oil in nearly quantitative yield (1.54 g). TLC $R_f=0.38$ (chloroform/ethyl acetate, 5:1). IR (neat) $\nu$ 3340, 1710, 1530 cm$^{-1}$. NMR (CDCl$_3$) $\delta$ 7.3 (5H, s), 7.25 (1H, m), 5.05 (2H, s), 5.0 (1H, m), 4.1 (1H, m), 3.8 (3H, s), 3.1 (2H, m), 2.0-1.1 (6H, m), 1.4 (9H, s). The product has the structural formula:

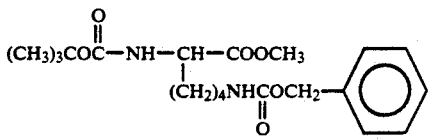

EXAMPLE 8

Preparation of
3-Carbamoyl-1-(2,4-dinitrophenyl)pyridinium chloride

A mixture of 20 g (98.7 mmol) of 1-chloro-2,4-dinitrobenzene and 8 g (65.5 mmol) of nicotinamide was gradually heated to 100° C., then stirred at that temperature for one hour. The mixture was cooled to ambient temperature and 100 mL of anhydrous methanol were added. The resultant solution was poured into 400 mL of anhydrous ethyl ether, with vigorous stirring. The solvent was removed by decantation and the residual precipitate was dissolved in 100 mL of methanol. The resultant solution was poured into 400 mL of anhydrous ethyl ether, the solvent was again removed by decantation and the solid residue was dissolved in 200 mL of water. The aqueous solution was refluxed with active charcoal for 30 minutes, then filtered. The filtrate was evaporated and dried in vacuo over phosphorus pentoxide to give 14.7 g (69.2%) of the title compound of the formula

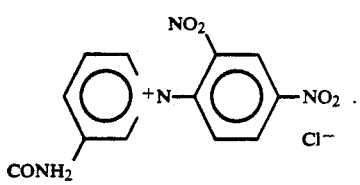

EXAMPLE 9

Preparation of
L-1-[5-(tert-butoxycarbonyl)amino-5-methoxycarbonyl]pentyl-3-carbamoylpyridinium chloride A mixture of 0.69 g (1.75 mmol) of $N^\epsilon$-benzyloxycarbonyl-$N^\alpha$-(tert-butoxycarbonyl)-L-lysine methyl ester and 0.17 g of 10% palladium on carbon catalyst in 10 mL of methanol was stirred under a hydrogen atmosphere for 3 hours. The catalyst was then removed by filtration. To the filtrate was added a solution of 0.568 g (1.75 mmol) of 3-carbamoyl-1-(2,4-dinitrophenyl)-pyridinium chloride in 1.5 mL of methanol. The resultant reaction mixture was refluxed overnight, then the precipitate was removed by filtration and the filtrate was evaporated. The residual oil was triturated with a mixture of acetone and ethyl acetate, affording a yellow solid. The solvent was removed and the residue was washed with a mixture of acetone and ethyl acetate and dried in vacuo to give 0.308 g (45.6%) of the title compound as a pale yellow solid. The product, which has the structure

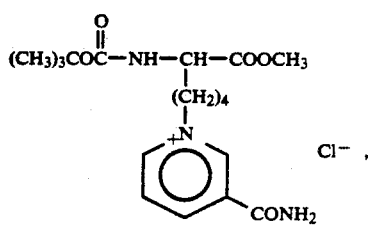

was characterized as follows: IR (KBr tablet) $\nu$ 3380, 1730, 1695, 1685, 1510, 1390, 1165 cm$^{-1}$; NMR (DMSO-d6) $\delta$ 9.83 (1H, s), 9.33 (1H, d, J=6 Hz), 9.1 (2H, m), 8.25 (1H, dd, J=6, 8 Hz), 8.12 (1H, bs), 7.2 (1H, bd, J=7.5 Hz), 4.7 (2H, bt, 7 Hz), 3.9 (1H, m), 3.6 (3H, s), 2.0 (2H, m), 1.35 (9H, s).

EXAMPLE 10

Preparation of 3-Quinolinemethanol

To a solution of 3.14 g (20 mmol) of 3-quinolinecarboxaldehyde in 60 mL of methanol was added portionwise 0.95 g (25 mmol) of sodium borohydride at 0° C. The reaction mixture was then stirred at room temperature for 2 hours. Excess sodium borohydride was quenched with acetic acid and the reaction mixture was evaporated in vacuo. The residue was dissolved in dilute aqueous sodium bicarbonate and extracted three times with ethyl acetate. The organic layer was washed with saturated brine, dried over anhydrous magnesium sulfate and evaporated in vacuo to give an oil. The oil was chromatographed on silica gel, using first 3:2 chloroform/ethyl acetate and then ethyl acetate as eluents, to afford 2.35 g (79.5%) of the title compound of the structural formula

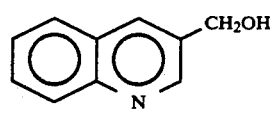

The product was characterized as follows: TLC $R_f$=0.30 (ethyl acetate); IR (neat) $\nu$ 3120, 1580, 1500, 1060 cm$^{-1}$; NMR (CDCl$_3$) $\delta$ 8.73 (1H, d, J=2 Hz), 8.07 (1H, s), 8.02 (1H, d, J=7 Hz), 7.8-7.3 (3H, m), 4.82 (2H, s).

EXAMPLE 11

Preparation of 3-Chloromethylquinoline hydrochloride

To a solution of 2.53 g (15.9 mmol) of 3-quinolinemethanol in 25 mL of toluene was added dropwise at room temperature 5 mL of thionyl chloride. The reaction mixture was stirred at that temperature for 4 hours, then dried in vacuo to give a solid which was suspended in 20 mL of toluene and treated with 4 mL of thionyl chloride at room temperature overnight. The reaction mixture was concentrated under reduced pressure to give 2.05 g (60%) of a solid. The product, having the structural formula

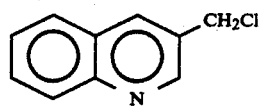

was not further purified. NMR (DMSO-d6) $\delta$ 9.36 (1H, d), 9.1 (1H, bs), 8.6-7.8 (4H, m), 5.2 (2H, s).

EXAMPLE 12

Preparation of Diethyl
(3-quinolylmethyl)acetamidomalonate

To a solution of sodium ethoxide [prepared from 0.25 g (11 mg-atoms) of sodium metal] in 24 mL of ethanol was added, in one portion, 2.39 g (11 mmol) of diethyl acetamidomalonate at room temperature. The reaction mixture was stirred for an additional 30 minute period. To that reaction mixture was then added a solution of 3-chloromethylquinoline [prepared from 2.05 g (9.25 mmol) of its hydrochloride salt by treatment with aqueous sodium bicarbonate and extraction with methylene chloride] in 5 mL of ethanol. The resultant reaction mixture was refluxed overnight, then was evaporated in vacuo, dissolved in 1N hydrochloric acid and extracted with ethyl acetate. The aqueous layer was neutralized with solid sodium bicarbonate and extracted twice with ethyl ether. The ether layer was washed with saturated brine, dried over anhydrous magnesium sulfate and evaporated in vacuo. The oil thus obtained was chromatographed on silica gel, using 2:1 chloroform/ethyl acetate as eluent, to afford a white crystalline product. Recrystallization from a mixture of ethyl acetate and isopropyl ether gave 1.28 g (38.8%) of the pure compound of the formula

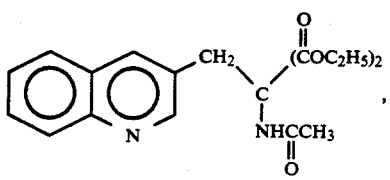

melting at 124°-125° C.; thin layer chromatography ($R_f$=0.28; chloroform/ethyl acetate, 2:1) and IR and NMR spectra confirmed the identity of the title compound.

EXAMPLE 13

Preparation of 3-(3-Quinolyl)alanine

A suspension of 1.19 g (3.34 mmol) of diethyl (3-quinolylmethyl)acetamidomalonate in 30 mL of 10% aqueous hydrochloric acid was refluxed overnight. The reaction mixture was then cooled to room temperature and neutralized with 10% aqueous sodium hydroxide solution. The precipitate was removed by filtration, washed with water and dried in vacuo to yield 0.48 g (66.4%) of the desired product as a white solid melting at 241°-243° C. Elemental analysis and IR confirmed the identity of the product, which has the formula

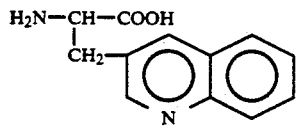

EXAMPLE 14

Preparation of 1-3-(Benzyloxycarbonylamino)alanine

A solution of 5 g (35.5 mmol) of 2,3-diaminopropionic acid in 88.6 mL of 0.05M phosphate buffer solution was cooled in ice. The pH of the solution was adjusted to 6.7 with 10% aqueous sodium hydroxide solution. A solution of 7.6 mL (53.7 mmol) of benzyl chloroformate in 7.1 mL of toluene was added dropwise, with vigorous stirring, over a one hour period. The pH was monitored and adjusted to between 6.5 and 7.0 by the addition of 10% aqueous sodium hydroxide solution. The reaction mixture was stirred with cooling at a pH of about 6.5 for an additional 5 hours, then was refrigerated overnight. The resulting precipitate was collected by filtration and the solid was washed with water and ethyl ether. Crystallization from water gave 1.12 g (12.4%) of white crystals melting at 233°-235° C. (with decomposition). The product has the structural formula:

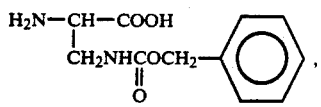

and was subsequently prepared in 55.7% yield using the same general procedure.

EXAMPLE 15

Preparation of 1-3-Benzyloxycarbonylamino-N-(tert-butoxycarbonyl)alanine

To a solution of 0.7 g (2.96 mmol) of 1-3-(benzyloxycarbonylamino)alanine and 0.62 mL (4.4 mmol) of triethylamine in 14 mL of 50% aqueous dioxane was added, in one portion, 0.79 g (3.26 mmol) of 2-(tert-butoxycarbonyloxyimino)-2-phenylacetonitrile. Stirring was continued overnight at room temperature. The reaction mixture was diluted with 14 mL of water and extracted twice with ethyl acetate. The aqueous layer was acidified with 1N hydrochloric acid and extracted three times with ethyl acetate. That organic layer was washed twice with water, then once with saturated brine, dried over anhydrous magnesium sulfate and evaporated in vacuo. The residue was chromatographed on silica gel (15 g), using first chloroform and then ethyl acetate as eluents, to give 0.88 g (92.8%) of a colorless oil. NMR (CDCl$_3$) δ 8.0 (1H, bs), 7.3 (5H, s), 6.2 (1H, m), 5.7 (1H, m), 5.1 (2H, bs), 4.3 (1H, m), 3.55 (2H, m), 1.4 (9H, s). The product has the structural formula:

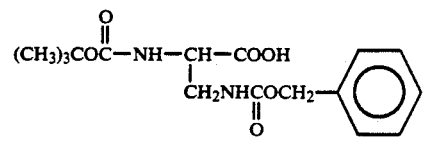

EXAMPLE 16

Preparation of 1-3-Benzyloxycarbonylamino-N-(tert-butoxycarbonyl)alanylglycine ethyl ester To a solution of 0.14 g (1 mmol) of glycine ethyl ester hydrochloride and 0.14 mL (1 mmol) of triethylamine in 5 mL of chloroform was added a solution of 0.32 g (1 mmol) of 1-3-benzyloxycarbonylamino-N-(tert-butoxycarbonyl)alanine in 3 mL of chloroform. Then, 0.21 g (1 mmol) of dicyclohexylcarbodiimide was added at room temperature and the reaction mixture was stirred at that temperature overnight. The reaction mixture was diluted with chloroform, washed successively with 0.5N hydrochloric acid, water, 3% aqueous sodium bicarbonate solution and water, dried over anhydrous sodium sulfate and concentrated under reduced pressure. The residue was chromatographed on silica gel (10 g), using first 5:1 chloroform/ethyl acetate and then 1:1 chloroform/ethyl acetate as eluents, to give a white solid. Crystallization from a mixture of ethyl acetate and isopropyl ether afforded 0.25 g (60.8%) of the title compound, melting at 131°-132° C. and having the structural formula:

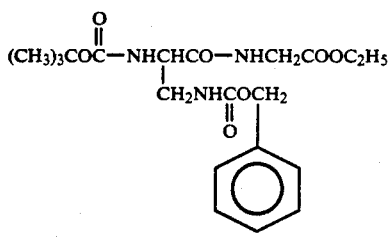

The structure was confirmed by NMR analysis.

EXAMPLE 17

Preparation of 1-1-[2-tert-Butoxycarbonylamino-2-(N-ethoxycarbonylmethyl)carbamoyl]ethyl-3-carbamoylpyridinium chloride A mixture of 0.192 g (0.467 mmol) of 1-3-benzyloxycarbonylamino-N-(tert-butoxycarbonyl)alanylglycine ethyl ester, 60 mg of 10% palladium on carbon catalyst and 6 mL of methanol was vigorously stirred for 3 hours at room temperature under a hydrogen atmosphere. The catalyst was removed by filtration and the filtrate was mixed with 0.15 g (0.467 mmol) of 3-carbamoyl-1-(2,4-dinitrophenyl)pyridinium chloride. The resultant reaction mixture was refluxed overnight. The precipitate was then removed by filtration and the filtrate was evaporated in vacuo. The residue was chromatographed on silica gel using first acetonitrile and then 10% aqueous acetonitrile as eluents, to give 20 mg of a brown oil. NMR (DMSO-d$_6$) δ 9.9 (1H, bs), 9.6 (1H, m), 9.3 (2H, m), 9.0 (1H, m), 8.35 (1H, q), 8.2 (1H, bs), 7.3 (1H, bd), 6.0 and 5.3 (1H, m), 4.8 (2H, m), 4.13 (2H, q), 3.95 (2H, m), 1.2 (12H, m). The product has the structural formula:

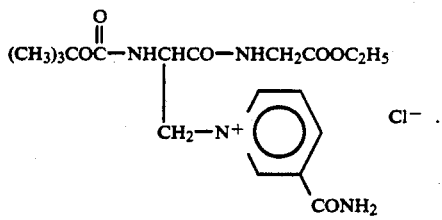

EXAMPLE 18

Preparation of 3-(3-Quinolyl)alanine ethyl ester dihydrochloride

A mixture of 0.45 g (2.08 mmol) of 3-(3-quinolyl)alanine, 1 mL of thionyl chloride and 20 mL of ethanol was gently refluxed overnight. The reaction mixture was concentrated under reduced pressure. The residue was dissolved in water and treated with active charcoal Removal of the active charcoal by filtration afforded a filtrate which was evaporated to give a white solid. Crystallization from a mixture of ethanol and ethyl ether gave 0.598 g (90.6%) of the title compound, melting at 204°–205° C. with decomposition. NMR spectrum was consistent with the assigned structure:

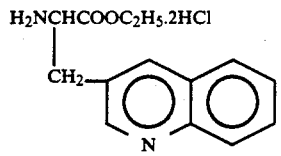

EXAMPLE 19

Preparation of N-(tert-Butoxycarbonyl)-3-(3-quinolyl)alanine ethyl ester

A mixture of 0.58 g (1.84 mmol) of 3-(3-quinolyl)alanine ethyl ester dihydrochloride, 0.78 mL (5.4 mmol) of triethylamine, 0.49 g (2.03 mmol) of 2-(tert-butoxycarbonyloxyimino)-2-phenylacetonitrile and 12 mL of 50% aqueous dioxane was stirred overnight at room temperature. The reaction mixture was then diluted with 15 mL of water and extracted three times with ethyl acetate. The organic layer was washed, first with water and then with saturated brine, then was dried over anhydrous magnesium sulfate and evaporated in vacuo. The residue was chromatographed on silica gel, using first 5:1 chloroform/ethyl acetate and then 2:1 chloroform/ethyl acetate as eluents, to give 0.486 g (76.7%) of a colorless oil. TLC R$_f$=0.4 (chloroform/ethyl acetate, 2:1); NMR (CDCl$_3$) δ 8.7 (1H, d), 8.1 (1H, bd), 7.93 (1H, d), 7.9–7.4 (3H, m), 5.15 (1H, m), 4.63 (1H, m), 4.2 (2H, m), 3.3 (2H, m), 1.4 (9H, s), 1.3 (3H, t). The product has the structural formula:

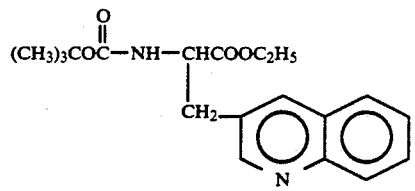

EXAMPLE 20

Preparation of 3-[2-(tert-Butoxycarbonyl)amino-2-ethoxycarbonyl]ethyl-1-methylquinolinium iodide A mixture of 0.486 g (1.41 mmol) of (N-tert-butoxycarbonyl)-3-(3-quinolyl)alanine ethyl ester, 2 mL of methyl iodide and 3 mL of acetone was refluxed overnight. The reaction mixture was evaporated in vacuo and the residue was chromatographed on silica gel, using first acetonitrile and then 2% aqueous acetonitrile as eluents, to give a yellow solid. Crystallization from a mixture of acetone and ethyl acetate yielded 0.497 g (72.5%) of a crystalline product melting at 98°–102° C. NMR spectrum and elemental analysis were consistent with the assigned structure:

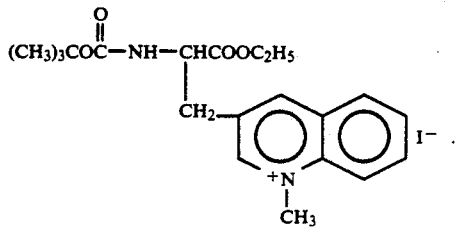

EXAMPLE 21

Preparation of
N-(tert-Butoxycarbonyl)-3-(1,2-dihydro-1-methyl-quinolin-3-yl)alanine ethyl ester To a solution of 0.2 g (0.41 mmol) of 3-[2-(tert-butoxycarbonyl)amino-2-ethoxycarbonyl]ethyl-1-methylquinolinium iodide in 10 mL of ethanol was added dropwise a solution of 20 mg (0.5 mmol) of sodium borohydride in 1 mL of ethanol at 0° C. After 5 minutes, the solution became colorless. The reaction mixture was diluted with 40 mL of deaerated water and extracted twice with deaerated ethyl ether. The combined organic layers were washed, first with deaerated water and then with saturated brine, then were dried over anhydrous magnesium sulfate and evaporated in vacuo to give 0.146 g (99.1%) of a yellow oil. TLC $R_f=0.8$ (4% methanol in chloroform); NMR (CDCl$_3$) δ 7.2–6.4 (4H, m), 6.15 (1H, bs), 5.05 (1H, bd), 4.4 (1H, m), 4.2 (2H, q), 3.9 (2H, bs),2.75 (3H, s), 2.55 (2H, m), 1.4 (9H, s), 1.25 (3H, t). The major product has been assigned the structural formula:

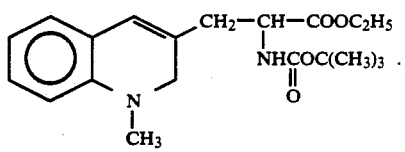

An alternative to the title nomenclature for this product is 3-[2-tert-butoxycarbonyl)amino-2-ethoxycarbonyl]ethyl-1,2-dihydro-1-methylquinoline.

EXAMPLE 22

Preparation of
N-(tert-Butoxycarbonyl)-3-(1,4-dihydro-1-methylquinolin-3-yl)alanine ethyl ester To a solution of 0.2 g (0.41 mmol) of 3-[2-(tert-butoxycarbonyl)amino-2-ethoxycarbonyl]ethyl-1-methylquinolinium iodide in 20 mL of deaerated water were added 0.2 g (2.4 mmol) of sodium bicarbonate and 20 mL of deaerated ethyl ether. The reaction mixture was stirred in an ice water bath and 0.29 g (1.64 mmol) of sodium dithionite was added in one portion. The reaction mixture was stirred for an additional 2 hour period at 0° C. The organic layer was separated, washed first with deaerated water and then with saturated brine, dried over anhydrous magnesium sulfate and evaporated in vacuo to give 76.6 mg (51.8%) of a yellow oil. TLC $R_f=0.77$ (4% methanol in chloroform); NMR ( (CDCl$_3$) δ 7.2–6.5 (4H, m), 5.8 (1H, m), 5.0 (1H, m), 4.35 (1H, m), 4.2 (2H, q), 3.5 (2H, bs), 3.0 (3H, s), 2.4 (2H, m), 1.49 (9H, s), 1.25 (3H, t). The major product has been assigned the structure:

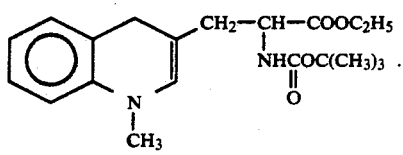

An alternative to the title nomenclature for this product is 3-[2-(tert-butoxycarbonyl)amino-2-ethoxycarbonyl]ethyl-1,4-dihydro-1-methylquinoline.

EXAMPLE 23

Preparation of Diethyl
β-(p-methoxyanilino)methylenemalonate

A mixture of 24.6 g (0.2 mol) of p-anisidine and 43.2 g (0.2 mol) of diethyl ethoxymethylenemalonate was heated at 130° C. until no more bubbles of alcohol could be detected. The reaction mixture was cooled in a dry ice/methanol bath, affording a solid mass. To that residue were added 40 mL of ethyl ether and the dark brown solid was crushed well with the ether to form white crystals. The solid was collected on a previously cooled Buchner funnel to give 42.48 g (72.4%) of a gray solid melting at 38°–39° C. IR (KBr) ν 1680, 1640, 1620, 1595, 1525, 1230 cm$^{-1}$; NMR (acetone-d$_6$) δ 8.4 (1H, d), 7.3 (2H, d), 6.95 (2H, d), 4.2 (4H, m), 3.8 (3H, s), 1.3 (6H, dt). The product has the structural formula:

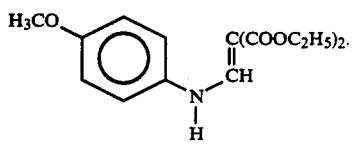

EXAMPLE 24

Preparation of
1,4-Dihydro-3-ethoxycarbonyl-6-methoxy-4-oxoquinoline

To 200 mL of boiling diphenyl ether were added rapidly 42 g (0.14 mol) of diethyl β-(p-methoxyanilino)-methylenemalonate. The dark solution was heated under reflux for 30 minutes, then was cooled to room temperature and diluted with 200 mL of n-hexane. The brown solid which formed was collected, washed twice with n-hexane and then twice with ethyl ether and then dried in vacuo. The resultant solid was suspended in 60 mL of ethanol and the suspension was boiled for 30 minutes, then cooled to room temperature. The product was collected as a pale brown solid (19.34 g, 52.1%), melting at 274°–277° C. IR (KBr) ν 3600–2600, 1685, 1620, 1575, 1560, 1520, 1480, 1290, 1170 cm$^{-1}$; NMR (CDCl$_3$) δ 8.45 (1H, s), 7.6 (2H, two d), 7.3 (1H, dd), 4.2 (2H, q), 3.8 (3H, s), 1.3 (3H, t). The compound is further characterized by the structural formula

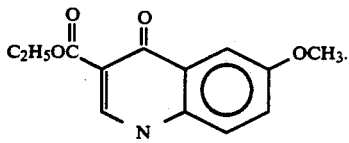

EXAMPLE 25

Preparation of
L-1-[5-(tert-Butoxycarbonyl)amino-5-methoxycarbonyl]pentyl-3-carbamoyl-1,4-dihydropyridine To a solution of 0.2 g (0.5 mmol) of L-1-[5-(tert-butoxycarbonyl)amino-5-methoxycarbonyl]pentyl-3-carbamoylpyridinium chloride in 20 mL of deaerated water were added 0.25 g (3 mmol) of sodium bicarbonate and 20 mL of deaerated ethyl ether. The reaction mixture was cooled, with stirring, in an ice bath and 0.35 g of sodium dithionite was added in one portion. The reaction mixture was stirred for an additional one hour at 0° C. The Organic layer was separated, washed with deaerated water and saturated brine, dried over anhydrous magnesium sulfate and evaporated in vacuo to give 41 mg (23.3%) of a yellow oil. TLC R$_f$=0.57 (chloroform/methanol), 5:1); NMR (CDCl$_3$) δ 7.0 (1H, d); 5.7 (1H, m), 5.5 (1H, m), 5.2 (1H, bd), 4.7 (1H, dt), 4.3 (1H, m), 3.75 (3H, s), 3.15 (2H, m), 1.49 (9H, s). The product has the structural formula:

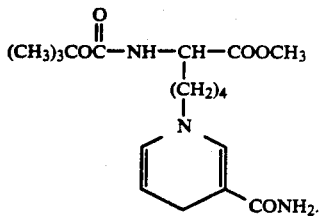

EXAMPLE 26

Preparation of
L-1-[5-(tert-Butoxycarbonyl)amino-5-methoxycarbonyl]pentyl-3-carbamoyl-1,4-dihydropyridine To a solution of 0.2 g (0.5 mmol) of L-1-[5-(tert-butoxycarbonyl)amino-5-methoxycarbonyl]pentyl-3-carbamoylpyridinium chloride in 20 mL of deaerated methanol was added 20 mg of sodium borohydride at 0° C. The reaction mixture was stirred for an additional 30 minutes at that temperature, then was evaporated in vacuo and diluted with deaerated water. Extraction with deaerated ethyl ether afforded an organic layer, which was washed with deaerated water and saturated brine, dried over anhydrous magnesium sulfate and evaporated in vacuo. Obtained in this manner was a complex mixture which was shown by NMR spectral analysis to contain the 1,4-dihydro derivative and the 1,6-dihydro derivative. The residue was chromatographed on silica gel (packed by 5% triethylamine in methylene chloride and eluted with 1:9 ethyl acetate/chloroform containing 0.5% triethylamine) to give 21 mg (12%) of the title 1,4-dihydro derivative as a yellow oil, identical to the product of EXAMPLE 25.

EXAMPLE 27

Preparation of
4-Chloro-3-ethoxycarbonyl-6-methoxyquinoline

A mixture of 19 g (76.8 mmol) of 1,4-dihydro-3-ethoxycarbonyl-6-methoxy-4-oxoquinoline and 60 mL of phosphorus oxychloride (POCl3) was refluxed for 4 hours. Excess phosphorus oxychloride was evaporated and the residue was poured onto 100 g of ice, made alkaline with 28% ammonium hydroxide, and allowed to remain at room temperature. The precipitate which formed was collected, washed twice with water and dried in vacuo to give 20 g of the product as a pale brown solid, in quantitative yield. TLC R$_f$=0.41 (2% methanol in chloroform); NMR (CDCl3) δ 8.95 (1H, s), 8.05 (1H, bd), 7.6 (2H, m), 4.45 (2H, q), 4.0 (3H, s), 1.4 (3H, t); IR (KBr) ν 1740, 1620, 1580, 1500, 1295, 1230, 1020, 830 cm$^{-1}$. The product has the formula:

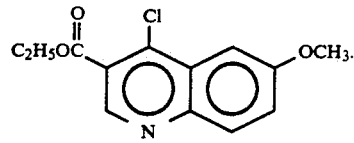

EXAMPLE 28

Preparation of 3-Ethoxycarbonyl-6-methoxyquinoline

A mixture of 20 g (75.8 mmol) of 3-ethoxycarbonyl-4-chloro-6-methoxyquinoline, 1.5 g of 10% palladium on carbon catalyst, 20 mL of triethylamine and 300 mL of ethanol was shaken under a hydrogen atmosphere (30 psi) at room temperature overnight. The catalyst was removed by filtration and the filtrate was evaporated. The residue was dissolved in methylene chloride, washed with aqueous sodium bicarbonate solution and water, dried over anhydrous sodium sulfate and evaporated in vacuo. That residue was suspended in 500 mL of cyclohexane and the resultant suspension was refluxed, then filtered to remove insoluble materials. The filtrate was allowed to stand at room temperature and the crystalline material which formed was collected to give 9.18 g (51.5%) of a pale brown solid having the structural formula:

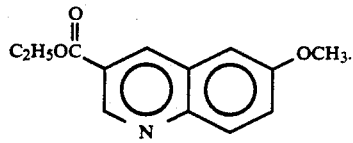

NMR (CDCl3) δ 9.25 (1H, d), 8.7 (1H, d), 8.05 (1H, d, J=9 Hz), 7.5 (1H, dd, J=9 Hz, 3 Hz), 7.2 (1H, d, J=3 Hz), 4.45 (2H, q), 3.9 (3H, s), 1.45 (3H, t). IR (KBr) ν 1713, 1620, 1600, 1500, 1240, 1100, 1025 cm$^{-1}$.

EXAMPLE 29

Preparation of 3-Hydroxymethyl-6-methoxyquinoline

To a suspension of 5.9 g (25 mol) of 3-ethoxycarbonyl-6-methoxyquinoline in 120 mL of 1:1 toluene/methylene chloride were added dropwise at −50° C., 36.7 mL (55 mmol) of diisobutylaluminium hydride as a 1.5M solution in toluene. The reaction mixture was gradually warmed to room temperature. To this mixture were added about 4 mL of methanol to quench excess reducing agent, and then water was added with vigorous stirring. After 30 minutes, 150 mL of ethyl acetate and anhydrous magnesium sulfate were added and the mixture was stirred for an additional 30 minutes. The solid was removed by filtration and washed thoroughly with ethyl acetate. The filtrate and washings were combined and evaporated in vacuo. The residue was chromatographed on silica gel, using first ethyl acetate and then 2% ethanol in ethyl acetate as eluents, to give 1.72 g (36.4%) of the title compound as a solid which melts at 92°-93° C. after crystallization from a mixture of benzene and isopropyl ether. TLC R$_f$=0.17 (ethyl acetate); NMR (CDCl3) δ 8.6 (1H, d), 7.9 (2H, m), 7.3 (1H, q), 6.95 (1H, d) 4.8 (2H, s), 3.85 (3H, s); IR (KBr) ν 3070, 1625, 1500, 1215 cm$^{-1}$.

A subsequent preparation using the same general procedure afforded the title compound in 71.5% yield.

EXAMPLE 30

Preparation of 3-Chloromethyl-6-methoxyquinoline hydrochloride

A mixture of 1.6 g (8.45 mmol) of 3-hydroxymethyl-6-methoxyquinoline, 3 mL of thionyl chloride and 16 mL of toluene was refluxed overnight. The reaction mixture was diluted with 16 mL of toluene. The solid was separated by filtration, washed thoroughly with toluene and dried in vacuo to give 1.52 g (73.7%) of a pale brown solid: NMR (DMSO-d$_6$) δ 9.15 (1H, d), 8.9 (1H, bs), 8.3 (1H, d), 7.7 (2H, m), 5.1 (2H, s), 3.95 (3H, s); IR (KBr) ν 2540, 2340, 2020, 1620, 1573, 1495, 1250 cm$^{-1}$. The product has the structural formula:

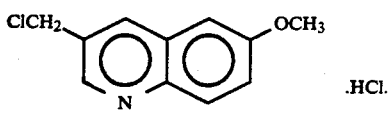

A subsequent preparation using the same general procedure afforded the desired compound in 87.0% yield.

EXAMPLE 31

Preparation ion of Diethyl (6-methoxy-3-quinolyl)methylacetamidomalonate

To a solution of sodium ethoxide prepared from 0.3 g (13.1 mmol) of sodium and 30 mL of ethanol were added, in one portion, 2.85 g (13.1 mmol) of diethyl acetamidomalonate. After 30 minutes, 1.52 g (6.24 mmol) of 3-chloromethyl-6-methoxyquinoline hydrochloride were added and the resultant mixture was refluxed overnight. The reaction mixture was evaporated and the residue was dissolved in 25 mL of 1N hydrochloric acid and extracted twice with ethyl ether. The aqueous layer was neutralized with solid sodium bicarbonate and extracted twice with chloroform. The chloroform layer was washed with water, dried over anhydrous magnesium sulfate and evaporated in vacuo. The residue was chromatographed on silica gel, using first 4:1 methylene chloride/ethyl acetate and then 1:1 methylene chloride/ethyl acetate as eluents, to give 1.82 g (75.2%) of the desired product as a white solid, which melted at 151°-152° C. after crystallization from a mixture of ethyl acetate and isopropyl ether. TLC R$_f$=0.34 (ethyl acetate); NMR (CDCl$_3$) δ 8.4 (1H, d), 7.9 (1H, d), 7.7 (1H, bs), 7.35 (1H, d), 7.0 (1H, d), 6.6 (1H, bs), 4.3 (4H, q), 3.9 (3H, s), 3.85 (2H, s), 2.05 (3H, s), 1.3 (6H, t); IR (KBr) ν 3400, 3230, 1740, 1640, 1300 cm$^{-1}$. The product has the formula:

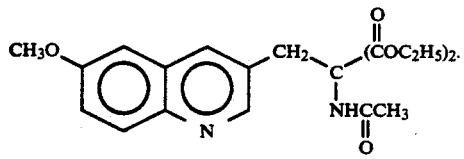

An improved yield of 89.3% was obtained when the above procedure was repeated subsequently.

EXAMPLE 32

Preparation of N$^ε$-Benzyloxycarbonyl-N$^α$-(tert-butoxycarbonyl)-L-lysylglycine ethyl ester To a solution of 0.73 g (5.26 mmol) of glycine ethyl ester hydrochloride and 0.74 mL (5.26 mmol) of triethylamine in 42 mL of chloroform were added successively, at 0° C., 2.0 g (5.26 mmol) of N$^ε$-benzyloxycarbonyl-N$^α$-(tert-butoxycarbonyl)-L-lysine and 1.09 g (5.26 mmol) of dicyclohexylcarbodiimide. The reaction mixture was stirred overnight at room temperature. The resulting precipitate was removed by filtration and the filtrate was washed successively with 0.5N hydrochloric acid, water, 3% aqueous sodium bicarbonate solution and water, then dried over anhydrous sodium sulfate. Evaporation of the solvent afforded a residue which was triturated with ethyl acetate. Insoluble materials were removed by filtration and the filtrate was evaporated in vacuo. The residue was recrystallized from a mixture of ethyl acetate and isopropyl ether to give 1.15 g (48%) of the title compound as colorless crystals. The mother liquor was concentrated under reduced pressure and the residue was crystallized as before to give a second crop of crystals (0.77 g, 32.1%). Total yield 80.1%, melting point 69°-70° C. NMR and IR spectral analyses confirmed the identity of the product, which has the formula:

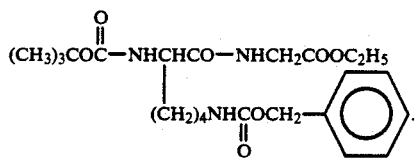

EXAMPLE 33

Preparation of (S)-1-[5-(tert-Butoxycarbonyl)amino-5-ethoxycarbonylmethylcarbamoyl]pentyl-3-carbamoylpyridinium chloride A mixture of 0.911 g (2 mmol) of N$^ε$-benzyloxycarbonyl-N$^α$-(tert-butoxycarbonyl)-L-lysylglycine ethyl ester and 0.25 g of 10% palladium on carbon catalyst in 5 mL of ethanol was vigorously stirred for 3 hours at room temperature under a hydrogen atmosphere. The reaction mixture was then filtered through Celite ® (a diatomaceous earth filter aid) and to the filtrate was added, in one portion, 0.65 g (2 mmol) of 3-carbamoyl-1-(2,4-dinitrophenyl)pyridinium chloride. The reaction mixture was stirred at room temperature overnight, during which time the color changed from dark red to reddish brown. The greenish brown precipitate which formed was removed by filtration and the filtrate was evaporated in vacuo. That residue was chromatographed on silica gel (using acetonitrile, 2% acetonitrile and 10% acetonitrile successively as the eluents) to give a brown oil. The product was taken up in anhydrous acetonitrile, filtered through Celite ®, evaporated and dried in vacuo to afford 0.603 g (65.1%) of the desired compound as a yellow solid. NMR (DMSO-d$_6$) δ 9.8 (1H, bs), 9.3 (1H, bd), 9.05 (1H, bd), 9.0 (1H, m), 8.45 (1H, t), 8.25 (1H, dd), 8.15 (1H, d), 6.8 (1H, m), 4.7 (2H,m), 4.05 (2H, q), 4.0 (1H, m), 3.8 (2H, m), 1.35 (9H, s), 1.15 (3H, t). Elemental analysis was consistent with the assigned structure:

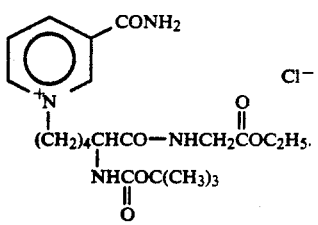

EXAMPLE 34

Preparation of
(S)-1-[5-(tert-Butoxycarbonyl)amino-5-ethoxycarbonylmethylcarbamoyl]pentyl-3-carbamoyl-1,4-dihydropyridine To a mixture of 0.236 g (0.5 mmol) of (S)-1-[5-(tert-butoxycarbonyl)amino-5-ethoxycarbonylmethylcarbamoyl]pentyl-3-carbamoylpyridinium chloride, 0.25 g (3 mmol) of sodium bicarbonate, 11 mL of methylene chloride and 11 mL of water was added, in one portion at room temperature, 0.31 g (2.0 mmol) of sodium dithionite. The reaction mixture was stirred for an additional one hour period. The organic layer was separated, dried over anhydrous sodium sulfate and evaporated in vacuo to afford 0.19 g (87.1%) of a yellow oil. The product has the structural formula

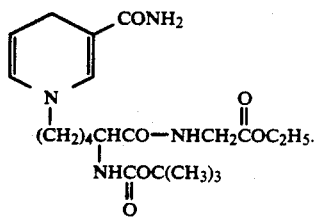

NMR (acetone-d6) δ (1H, m), 7.0 (1H, bs), 6.3 (2H, bs), 6.2 (1H, d), 5.85 (1H, d), 4.65 (1H, dt), 4.15 (3H, q+m), 4.0 (2H, m), 3.15 (4H, m), 1.4 (9H, s), 1.13 (3H, t). Elemental analysis was in agreement with the assigned structure.

EXAMPLE 35

Preparation of Diethyl (6-hydroxy-3-quinolyl)methylacetamidomalonate

To a solution of 0.39 g (1 mmol) of diethyl (6-methoxy-3-quinolyl)methylacetamidomalonate in 10 mL of dry methylene chloride was added dropwise at −70° C. a 1M solution of boron tribromide in methylene chloride. The reaction temperature was gradually raised to room temperature while stirring overnight. Then, the reaction mixture was poured into ice water and extracted with methylene chloride. The organic layer was washed with water, dried over anhydrous magnesium sulfate and evaporated in vacuo. The residue was chromatographed on silica gel, using 1:1 ethyl acetate/methylene chloride and then ethyl acetate as eluents, to give 43 mg (11.5%) of the desired product as a solid. TLC R$_f$=0.46 (ethyl acetate); NMR (CDCl$_3$) δ 8.4 (1H, bs), 7.95 (1H, d), 7.7 (1H, bs), 7.35 (1H, dd), 7.1 (1H, d), 6.8 (1H, bs), 4.25 (4H, m), 3.8 (2H, bs), 2.0 (3H, s), 1.3 (6H, m); IR (KBr) ν 3700–2800, 1740, 1660, 1645, 1620, 1500 cm$^{-1}$. The product has the structural formula:

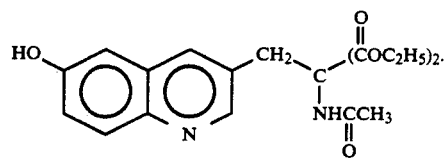

EXAMPLE 36

Preparation of 3-(6-Methoxy-3-quinolyl)alanine

A mixture of 0.602 g (1.55 mmol) of diethyl (6-methoxy-3-quinolyl)methylacetamidomalonate and 8.2 mL of 10% hydrochloric acid was refluxed overnight. The reaction mixture was cooled to room temperature and neutralized with 1 N sodium hydroxide solution to pH 6.7. The white solid which formed was separated by filtration, washed successively with water and ethyl ether and dried in vacuo to give 0.282 g (73.9%) of the title compound melting at 246°–247° C. and having the structural formula

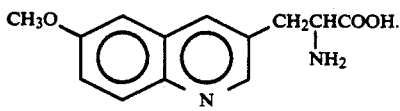

NMR and IR spectral analyses and elemental analysis confirmed the identity of the product.

EXAMPLE 37

Preparation of 3-(6-Hydroxy-3-quinolyl)alanine

A mixture of 0.18 g (0.74 mmol) of 3-(6-methoxy-3-quinolyl)alanine and 5.4 mL of 48% hydrobromic acid was stirred at 85°–90° C. overnight. The reaction mixture was cooled to room temperature and neutralized to pH 7.0 with 1N sodium hydroxide solution, then was concentrated under reduced pressure to give a brown solid. After filtration, the solid product was washed with a small amount of cold water and ethyl ether and then was dried in vacuo to give 57.4 mg (33.4%) of the title compound of the formula:

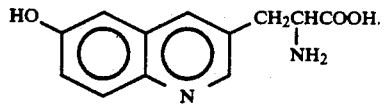

NMR (DMSO-d$_6$, CF$_3$COOH) δ 9.05 (1H, bs), 8.9 (1H, bs), 8.2 (1H, d), 7.7 (1H, dd), 7.5 (1H, d) 4.5 (1H, m), 3.5 (2H, m); IR (KBr) ν 3400, 1630, 1500 cm$^{-1}$.

EXAMPLE 38

Preparation of N-(tert-Butoxycarbonyl)-3-(6-hydroxy-3-quinolyl)alanine ethyl ester A mixture of 0.388 g (1 mmol) of diethyl (6-methoxy-3-quinolyl)methylacetamidomalonate and 7.4 mL of 48% hydrobromic acid was stirred at 85° C. for 24 hours. The solvent was evaporated and the residue was dissolved in 7 mL of ethanol. Then, 0.3 mL of thionyl chloride was added at 0° C. and the mixture was refluxed overnight. The reaction mixture was evaporated in vacuo, taken up in benzene and then evaporated to dryness in vacuo to give a crude, highly hygroscopic residue. To a mixture of this crude product together with 0.39 mL (2.7 mmol) of triethylamine and 6 mL of 50% aqueous 1,4-dioxane there was added, in one portion, 0.24 g (1 mmol) of 2-(tert-butoxycarbonyloxyimino)-2-phenylacetonitrile. The reaction mixture was stirred overnight at room temperature, then was diluted with 6 mL of water and extracted twice with chloroform. The organic layer was washed with water, dried over anhydrous magnesium sulfate and evaporated in vacuo. The residue was chromatographed on silica gel. Elution with 5:1 methylene chloride/ethyl acetate gave 94 mg (27.6%) of the methoxy derivative, i.e. N-(tert-butoxycarbonyl)-3-(6-methoxy-3-quinolyl)alanine ethyl ester, having the formula:

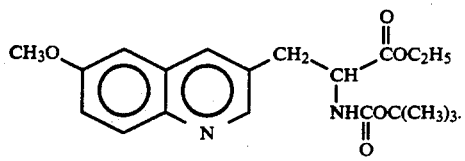

TLC R$_f$=0.57 (1:1 methylene chloride/ethyl acetate); NMR (CDCl$_3$) δ 8.55 (1H, d), 8.0 (1H, d), 7.85 (1H, bs), 7.35 (1H, dd), 7.0 (1H, d), 5.1 (1H, m), 4.65 (1H, m), 4.2 (2H, q), 3.9 (3H, s), 3.3 (2H, m), 1.4 (9H, s), 1.2 (3H, t).

The title compound was eluted with 1:1 methylene chloride/ethyl acetate to give 0.14 g or 42.7% yield; TLC R$_f$=0.31 (1:1 methylene chloride/ethyl acetate); melting point 176°-177° C. after crystallization from a mixture of ethyl acetate and isopropyl ether. The title compound has the formula

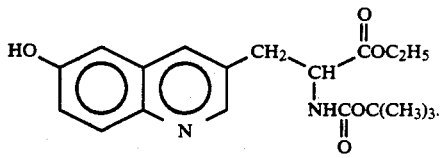

NMR (CDCl$_3$) δ 8.55 (1H, d), 7.95 (1H, d), 7.8 (1H, d), 7.35 (1H, dd), 7.15 (1H, d), 5.3 (1H, m), 4.6 (1H, m), 4.15 (2H, q), 3.25 (2H, m), 1.35 (9H, s), 1.2 (3H, t); IR (KBr) ν 3350, 1740, 1710, 1685, 1630, 1500, 1160 cm$^{-1}$.

EXAMPLE 39

Preparation of L-1-[2-(N-tert-Butoxycarbonyl)amino-2-(N-ethoxycarbonylmethyl)carbamoyl]ethyl-3-carbamoylpyridinium chloride A mixture of 0.81 g (1.92 mmol) of 3-benzyloxycarbonylamino-N-(tert-butoxycarbonyl)-L-alanylglycine ethyl ester, 0.2 g of 10% palladium on carbon catalyst and 30 mL of ethanol was stirred vigorously at room temperature for 4 hours under a hydrogen atmosphere. The reaction mixture was filtered and the solid residue was washed with 10 mL of ethanol. The filtrate and washing were combined and 0.623 g (1.92 mmol) of 3-carbamoyl-1-(2,4-dinitrophenyl)pyridinium chloride was added in one portion. Stirring was continued at room temperature overnight, then the reaction mixture was filtered and the filtrate was evaporated in vacuo. The residue was chromatographed on silica gel, using first 2% aqueous acetonitrile and then 5% aqueous acetonitrile as eluents. The eluate was concentrated to approximately 100 mL under reduced pressure and then was diluted with 300 mL with water. The resulting solution was concentrated to approximately 100 mL and treated with active charcoal. Removal of the solid by filtration gave a filtrate which was lyophilized to give 0.202 g (24.4%) of the title compound as a white solid. That compound, which can alternatively be prepared by the process of EXAMPLE 3, can also be named as N-(tert-butoxycarbonyl)-3-(3-carbamoyl-1-pyridinium)-L-alanylglycine ethyl ester. It has the structure depicted in EXAMPLE 3.

EXAMPLE 40 Preparation of
N$^\epsilon$-Benzyloxycarbonyl-N$^\alpha$-(tert-butoxycarbonyl)-L-lysyl-L-phenylalanyl-L-leucine ethyl ester.

To a mixture of 1.68 g (4 mmol) of L-phenylalanyl-L-leucine ethyl ester trifluoroacetate, 0.56 mL (4 mmol) of triethylamine and 32 mL of chloroform were added at 0° C., first 1.52 g (4 mmol) of N$^\epsilon$-benzyloxycarbonyl-N$^\alpha$-(tert-butoxycarbonyl)-L-lysine, and then 0.83 g (4 mmol) of dicyclohexylcarbodiimide, each being added in a single portion. The reaction mixture was warmed gradually to room temperature and then stirred overnight at that temperature. The precipitate which formed was removed by filtration. The filtrate was evaporated in vacuo and the residue was chromatographed on silica gel using 3:1 methylene chloride/ethyl acetate as eluent to give 2.48 g (92.7%) of the title compound as a white solid melting at 135°-136° C. after crystallization from a mixture of ethyl acetate and isopropyl ether. The product has the structural formula:

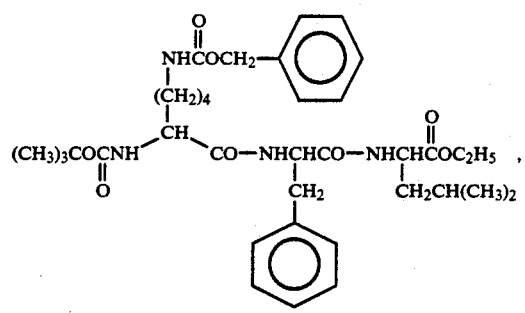

as further confirmed by NMR, IR and elemental analyses.

EXAMPLE 41

Preparation of L-[2-(tert-Butoxycarbonyl)amino-6-(3-carbamoyl-1-pyridinium)]hexanoyl-L-phenylalanyl-L-leucine ethyl ester chloride A mixture of 1.0 g (1.5 mmol) of N$^\epsilon$-benzyloxycarbonyl-N$^\alpha$-(tert-butoxycarbonyl)-L-lysyl-L-phenylalanyl-L-leucine ethyl ester, 0.25 g of 10% palladium on carbon catalyst and 10 mL of ethanol was stirred vigorously for 3 hours at room temperature under a hydrogen atmosphere. The reaction mixture was filtered and the residue was washed with 5 mL of ethanol. The filtrate and washing were combined and 0.49 g (1.5 mmol) of 3-carbamoyl-1-(2,4-dinitrophenyl)pyridinium chloride was added in one portion at room temperature. The reaction mixture was stirred overnight at room temperature and then filtered. The filtrate was evaporated in vacuo and the residue was chromatographed on silica gel using 2% aqueous acetonitrile and then 8% aqueous acetonitrile as eluents. The eluate was concentrated to approximately 100 mL under reduced pressure, then was diluted with 300 mL of water and again evaporated to approximately 100 mL in vacuo. The resulting solution was treated with active charcoal and filtered. The filtrate was lyophilized to give 0.501 g (49.4%) of a very hygroscopic solid. NMR (DMSO-d$_6$) δ 9.65 (1H, bs), 9.2 (1H, bd), 9.0 (1H, bd), 8.8 (1H, bs), 8.5–8.1 (3H, m), 7.9 (1H, bd), 7.2 (5H, s), 6.85 (1H, m), 4.6 (4H, m), 4.1 (2H, q), 1.35 (9H, s), 0.9 (6H, m). The title compound prepared in this manner has the structural formula:

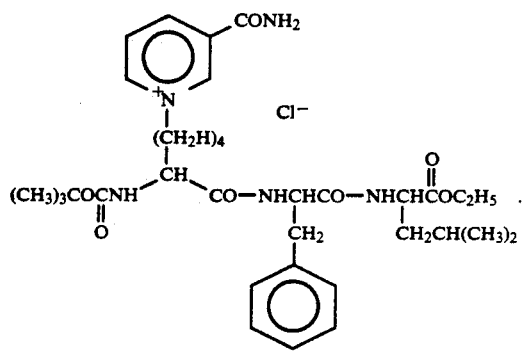

EXAMPLE 42

Preparation of 3-[2-(N-tert-Butoxycarbonyl)amino-2-ethoxycarbonyl-]ethyl-6-hydroxy-1-methylquinolinium iodide.

A mixture of 0.34 g (0.94 mmol) of N-(tert-butoxycarbonyl)-3-(6-hydroxy-3-quinolyl)alanine ethyl ester, 1.3 mL of methyl iodide and 2 mL of acetone was gently refluxed overnight. Evaporation in vacuo afforded a residue which was recrystallized from a mixture of acetone and ethyl acetate to give 0.39 g (82.6%) of the title compound as a yellow solid melting at 174°–175° C. NMR, IR and elemental analyses were consistent with the assigned structure:

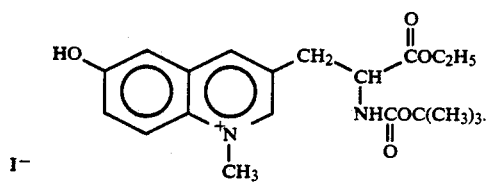

EXAMPLE 43

Preparation of N-(tert-Butoxycarbonyl)-3-(6-methoxy-3-quinolyl)alanine ethyl ester To a suspension of 0.54 g (2.19 mmol) of 3-(6-methoxy-3-quinolyl)alanine in 13.5 mL of ethanol was added dropwise 0.68 mL of thionyl chloride at 0° C. The reaction mixture was refluxed overnight, then was evaporated in vacuo, triturated with benzene and evaporated to dryness in vacuo. The crude product, 3-(6-methoxy-3-quinolyl)alanine ethyl ester dihydrochloride, was combined with 0.93 mL (6.4 mmol) of triethylamine and 14.2 mL of 50% aqueous 1,4-dioxane; to that mixture was added, in one portion, 0.58 g (2.4 mmol) of 2-(tert-butoxycarbonyloxyimino)-2-phenylacetonitrile. The resultant mixture was stirred overnight at room temperature, then was diluted with 15 mL of water and extracted twice with chloroform. The organic layer was washed with water, dried over anhydrous magnesium sulfate and evaporated in vacuo. The residue was chromatographed on silica gel, using 5:1 methylene chloride/ethyl acetate as eluent, to give a white solid which was recrystallized from isopropyl ether to afford 0.6 g (73.3%) of the title compound, melting at about 127° C. and having the structural formula:

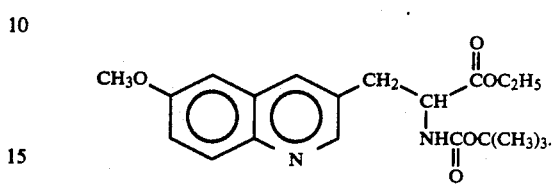

The identity of the product was confirmed by NMR and IR spectral analyses as well as by elemental analysis.

EXAMPLE 44

Preparation of 3-[2-N-(tert-Butoxycarbonyl)amino-2-ethoxycarbonyl-]ethyl-6-methoxy-1-methyl-3-quinolinium iodide A mixture of 0.415 g (1.11 mmol) of N-(tert-butoxycarbonyl)-3-(6-methoxy-3-quinolyl)alanine ethyl ester, 2 mL of methyl iodide and 3 mL of acetone was gently refluxed overnight. Evaporation in vacuo afforded a residue which was chromatographed on silica gel, using first 3:1 ethyl acetate/acetonitrile and then 1:2 ethyl acetate/acetonitrile as eluents, to give 0.53 g (93.1%) of a yellow amorphous solid. The title compound was further characterized as follows: NMR (DMSO-d$_6$) δ 9.37 (1H, bs), 8.9 (1H, bs), 8.4 (1H, d), 7.85 (1H, dd), 7.8 (1H, s), 7.4 (1H, m), 4.6 (3H, s), 4.5 (1H, m), 4.12 (2H, q), 4.0 (3H, s), 3.3 (2H, m), 1.27 (9H, s), 1.17 (3H, t). Elemental analysis further confirmed that the product was of the structural formula

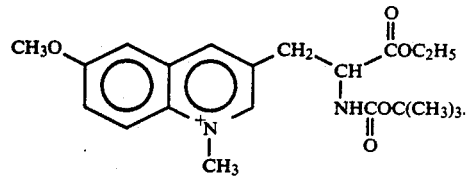

EXAMPLE 45

Preparation of N-(tert-Butoxycarbonyl)glycyl-3-(3-quinolyl)alanine ethyl ester

To a mixture of 0.637 g (2 mmol) of 3-(3-quinolyl)alanine ethyl ester dihydrochloride, 0.35 g (2 mmol) of N-(tert-butoxycarbonyl)glycine, 0.56 mL (4 mmol) of triethylamine and 16 mL of chloroform was added at 0° C., in one portion, 0.42 g (2 mmol) of dicyclohexylcarbodiimide. The reaction mixture was stirred overnight and the precipitate which formed was removed by filtration. The filtrate was washed twice with water, dried over anhydrous magnesium sulfate and evaporated in vacuo. The residue was chromatographed on silica gel, using first 1:1 methylene chloride/ethyl acetate and then 1:3 methylene chloride/ethyl acetate as eluents, to give 0.73 g (9.9%) of the title compound as a colorless oil. TLC R$_f$=0.52 (ethyl acetate); NMR (CDCl$_3$) δ 8.64 (1H, d), 7.9–8.1 (2H, m), 7.9–7.4 (4H, m), 7.1 (1H, bd), 5.46 (1H, bt), 4.9 (1H, m), 4.15 (2H, q), 3.8 (2H, bd), 3.3 (2H, m), 1.37 (9H, s), 1.2 (3H, t). The product has the formula:

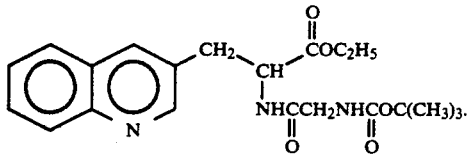

EXAMPLE 46

Preparation of 3-{2-[N-(tert-Butoxycarbonyl)glycyl]-amino-2-ethoxycarbonyl}ethyl-1-methylquinolinium A mixture of 0.55 g (1.37 mmol) of N-(tert-butoxycarbonyl)glycyl-3-(3-quinolyl)alanine ethyl ester, 1.9 mL of methyl iodide and 2.9 mL of acetone was gently refluxed overnight. The solvent was removed by evaporation and the residue was chromatographed on silica using first 2:1 ethyl acetate/acetonitrile and then 1:3 ethyl acetate/acetonitrile as eluents, to give 0.67 g (90.1%) of the title compound as a yellow amorphous solid. NMR (DMSO-d$_6$) δ 9.5 (1H, s), 9.1 (1H, s), 8.6–7.9 (5H, m), 6.9 (1H, m), 4.8 (1H, m), 4.63 (3H, s), 4.15 (2H, q), 3.45 (4H, m), 1.27 (9H, s), 1.2 (2H, t). The product has the formula:

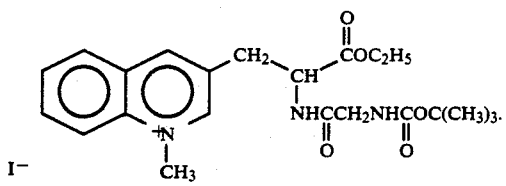

EXAMPLE 47

Preparation of L-L2-(tert-Butoxycarbonyl)amino-6-(3-carbamoyl-1,4-dihydropyridin-1-yl)]hexanoyl-L-phenylalanyl-L-leucine ethyl ester To a mixture of 0.1 g (0.15 mmol) of L-[2-(tert-butoxycarbonyl)amino-6-(3-carbamoyl-1-pyridinium)]-hexanoyl-L-phenylalanyl-L-leucine ethyl ester, 74 mg (0.89 mmol) of sodium bicarbonate, 5 mL of deaerated methylene chloride and 5 mL of deaerated water, there were added 92 mg (0.59 mmol) of sodium dithionite in one portion. The reaction mixture was stirred at room temperature for 2 hours, then the organic layer was separated and washed with deaerated water. Drying over anhydrous sodium sulfate and evaporation in vacuo afforded a brown amorphous product: NMR (CDCl$_3$) δ 7.25 (5H, s), 7.05 (1H, bs), 6.85 (1H, bd), 5.7 (3H, m), 5.3 (1H, bd), 4.7 (2H, m), 4.5 (1H, m), 4.15 (2H, q), 4.1 (1H, m), 3.1 (4H, m), 2.5 (2H, m), 1.4 (9H, s), 1.25 (3H, t), 0.9 (6H, m). The identity of the title compound was confirmed by elemental analysis. It has the structural formula:

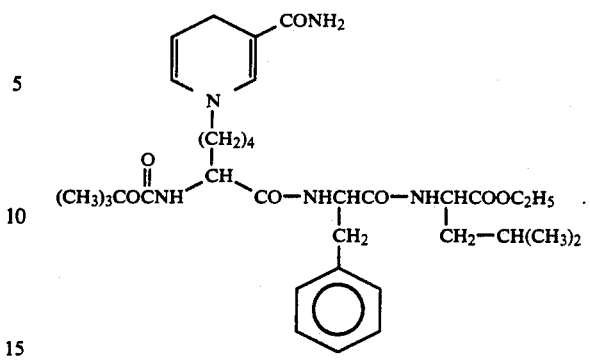

EXAMPLE 48

Preparation of O-Benzyl-N-(tert-butoxycarbonyl)-L-tyrosyl-N$^ε$-benzyloxycarbonyl-L-lysine methyl ester A solution of 1.04 g (2.64 mmol) of N$^{68}$-benzyloxycarbonyl-N$^α$-(tert-butoxycarbonyl)-L-lysine methyl ester in 5.3 mL of trifluoroacetic acid was stirred for 2 hours at room temperature. The reaction mixture was evaporated in vacuo to give a colorless oil, which was mixed with 0.966 g (2.6 mmol) of O-benzyl-N-(tert-butoxycarbonyl)-L-tyrosine, 0.37 mL (2.6 mmol) of triethylamine and 20.8 mL of chloroform. To that mixture was added, in one portion, 0.54 g (2.6 mL) of dicyclohexylcarbodiimide at 0° C. The reaction mixture was stirred for one hour at 0° C. and then overnight at room temperature. The solvent was removed by evaporation and the residue was chromatographed on silica gel, using first methylene chloride and then 1:1 methylene chloride/ethyl acetate as eluents, to give 0.49 g (29.1%) of a colorless solid. NMR (CDCl$_3$) δ 7.3 (10H, m), 7.1 (2H, d), 6.85 (2H, d), 6.5 (1H, m), 5.1 (2H, s), 5.0 (1H, m), 4.7–4.1 (2H, m), 3.65 (3H, s), 3.3–2.9 (4H, m), 1.4 (9H, s). A portion of the product was recrystallized from a mixture of ethyl acetate and isopropyl ether to give crystals melting at 167°–168° C. The product has the formula

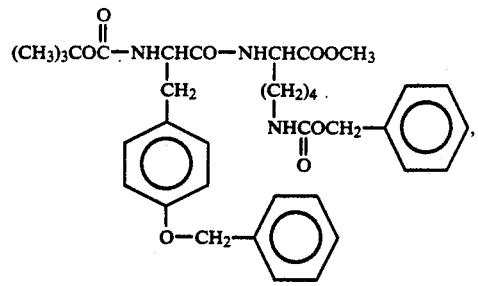

as confirmed by elemental analysis.

EXAMPLE 49

Preparation of 1-{5-[N-(tert-Butoxycarbonyl)-L-tyrosyl]amino-5-methoxycarbonyl}pentyl-3-carbamoylpyridinium chloride A mixture of 0.44 g (0.68 mmol) of O-benzyl-N-(tert-butoxycarbonyl)-L-tyrosyl-N$^ε$-benzyloxycarbonyl-L-lysine methyl ester, 90 mg of 10% palladium on carbon catalyst, 5 mL of methanol and 5 mL of dioxane was vigorously stirred for 1 hour under a hydrogen atmosphere. The reaction mixture was filtered and to the filtrate was added 0.22 g (0.68 mmol) of 3-carbamoyl-1-(2,4-dinitrophenyl)pyridinium chloride. That mixture was stirred overnight at room temperature and then evaporated. The residue was chromatographed on silica gel, using first acetonitrile and then 4% aqueous acetonitrile as eluents, to give a reddish brown oil, which was dissolved in distilled water, treated with active charcoal and lyophilized to afford 0.106 g (27.7%) of a colorless powder; NMR (D$_2$O, DSS) δ 9.65 (1H, bs), 9.3 (3H, m), 8.95 (2H, m), 8.5 (1H, dd), 8.25 (1H, d), 7.1 (2H, d), 6.8 (2H, d), 4.3 (2H, m), 3.7 (5H, m), 1.4 (9H, s). The product has the formula:

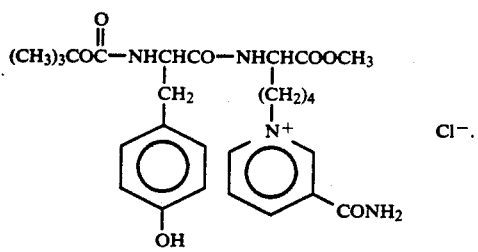

EXAMPLE 50

Preparation of O-Benzyl-N-(tert-butoxycarbonyl)-L-tyrosyl-N$^\epsilon$-benzyloxycarbonyl-L-lysylglycine ethyl ester A mixture of 0.94 g (2 mmol) of N$^\epsilon$-benzyloxycarbonyl-N$^\alpha$-(tert-butoxycarbonyl)-L-lysylglycine ethyl ester and 4 mL of trifluoroacetic acid was stirred for 40 minutes at room temperature. The reaction mixture was diluted with 30 mL of toluene and evaporated to approximately 3 mL. To this residue were added 40 mL of dry ethyl ether. Decantation of the solvent left a viscous oil which was mixed with 0.74 g (2 mmol) of O-benzyl-N-(tert-butoxycarbonyl)-L-tyrosine, 0.28 mL (2 mmol) of triethylamine and 16 mL of chloroform. Then, 0.42 g (2 mmol) of dicyclohexylcarbodiimide was added in one portion and the reaction mixture was stirred overnight at room temperature. The precipitate which formed was removed by filtration and the filtrate was washed successively with 0.5% aqueous hydrochloric acid, water, 3% aqueous sodium bicarbonate solution and water, then dried over anhydrous sodium sulfate. Evaporation of the solvent afforded a residue which was chromatographed on silica gel, using first 2:1 methylene chloride/ethyl acetate, and then 1:1 methylene chloride/ethyl acetate as eluents, to give 1.17 g (81.4%) of a colorless solid. NMR (CDCl$_3$) δ 7.3 (10H, m), 7.1 (2H, d), 6.85 (2H, d), 5.2 (1H, m), 5.1 (2H, s), 5.0 (2H, s), 4.4 (2H, m), 4.15 (2H, q), 3.9 (2H, d), 3.1 (4H, m), 1.4 (9H, s), 1.2 (3H, t); IR (KBr) ν 3300, 1690, 1640, 1510, 1240, 1175, 1025 cm$^{-1}$. A portion of the product was recrystallized from a mixture of isopropyl ether and ethyl acetate to afford a sample melting at 122°–124° C. Elemental analysis gave values in accord with the following assigned structure:

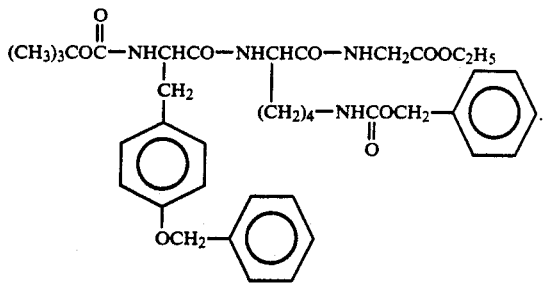

EXAMPLE 51

Preparation of 1-{5-[N-(tert Butoxycarbonyl)-L-tyrosyl]amino-5-ethoxycarbonyl-methylcarbamoyl}pentyl-3-carbamoylpyridinium chloride A mixture of 0.72 g (1 mmol) of O-benzyl-N-(tert-butoxycarbonyl)-L-tyrosyl-N$^\epsilon$-benzyloxycarbonyl-L-lysylglycine ethyl ester, 0.15 g of 10% palladium on carbon catalyst and 15 mL of ethanol was vigorously stirred for 2 hours under a hydrogen atmosphere. The catalyst was removed by filtration and 0.325 g (1 mmol) of 3-carbamoyl-1-(2,4-dinitrophenyl)pyridinium chloride was added to the filtrate. The reaction mixture was stirred overnight at room temperature. The solvent was removed by evaporation and the residue was chromatographed on silica gel, twice using acetonitrile, 3% aqueous acetonitrile and 6% aqueous acetonitrile successively as eluents, to give a reddish brown oil. The product was dissolved in distilled water, treated with active charcoal and lyophilized to give 0.109 g (17.1%) of a colorless solid; NMR (CD$_3$OD) δ 9.8 (1H, m), 9 4 (2H, m), 9 3 (JH, d), 8.95 (1H, dd), 8.5 (1H, dd), 8.4 (1H, d), 8.0 (1H, m), 7.1 (2H, d), 6.7 (2H, d), 4.15 (2H, q), 3.9 (2H, m), 3.7 (2H, m), 3.0 (4H, m), 1.4 (9H, s), 1.25 (3H, t). The product has the structural formula:

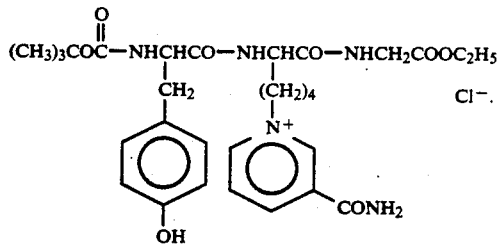

EXAMPLE 52

Preparation of O-Benzyl-N-(tert-butoxycarbonyl)-L-tyrosyl-N$^\epsilon$-benzyloxycarbonyl-L-lysylglycine A suspension of 0.608 g (0.85 mmol) of O-benzyl-N-(tert-butoxycarbonyl)-L-tyrosyl-N$^\epsilon$-benzyloxycarbonyl-L-lysylglycine ethyl ester in 60 mL of 50% aqueous methanol was adjusted to pH 12.5 with 1N aqueous sodium hydroxide solution and the reaction mixture was stirred overnight at room temperature. The reaction mixture was then diluted with 50 mL of water and concentrated to about half of the original volume. The concentrated reaction mixture was adjusted to pH 3 with 1N aqueous hydrochloric acid, then was extracted twice with ethyl acetate. The organic layer was washed with water and saturated brine, dried over anhydrous magnesium sulfate and evaporated to give 0.56 g (93.5%) of a white solid. NMR (CD₃OD) δ 7.4 (10H, m), 7.2 (2H, d), 6.9 (2H, d), 5.05 (4H, s), 4.3 (2H, m), 1.4 (9H, s); IR (KBr) ν 3500, 1670, 1640, 1510, 1240, 1160 cm⁻¹. The product has the structural formula:

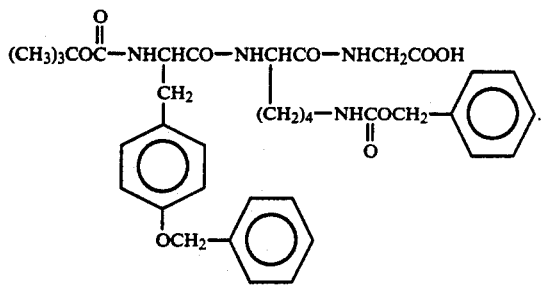

EXAMPLE 53

Preparation of O-Benzyl-N-(tert-butoxycarbonyl)-L-tyrosyl-N^ε-benzyloxycarbonyl-L-lysylglycyl-L-phenylalanyl-L-leucine ethyl ester To a mixture of 0.56 g (0.79 mmol) of O-benzyl-N-(tert-butoxycarbonyl)-L-tyrosyl-N^ε-benzyloxycarbonyl-L-lysylglycine, 0.40 g (0.95 mmol) of L-phenylalanyl-L-leucine ethyl ester trifluoroacetate, 0.112 g (0.83 mmol) of 1-hydroxybenztriazole hydrate, 0.13 mL (0.95 mmol) of triethylamine and 8 mL of dimethylformamide was added, in one portion at 0° C., 0.17 g (0.83 mmol) of dicyclohexylcarbodiimide. The reaction mixture was stirred overnight at room temperature, then was diluted with 200 mL of ethyl ether and washed three times with water and once with saturated brine. Drying over anhydrous magnesium sulfate and evaporation in vacuo afforded a residue which was chromatographed on silica gel, using first methylene chloride and then 1:1 methylene chloride/ethyl acetate as eluents, to give 0.61 g (78.9%) of a colorless solid. NMR (DMSO-d₆) δ 8.35 (1H, m), 8.0 (3H, m), 7.4 (15H, m), 7.2 (2H, d), 6.9 (2H, d), 5.05 (2H, s), 5.0 (2H, s), 4.6 (1H, m), 4.4–3.9 (6H, m), 3.7 (2H, m), 3.1–2.6 (6H, m), 1.3 (9H, s), 1.2 (3H, t), 0.9 (6H, m); IR (KBr) ν 3300, 1690, 1640, 1510, 1240 cm⁻¹. Elemental analysis values were consistent with the assigned structure:

EXAMPLE 54

Preparation of 3-[2-(N-tert-Butoxycarbonyl)amino-2-ethoxycarbonyl-]ethyl-1,4-dihydro-6 hydroxy-1-methylquinoline To a mixture of 0.1 g of 3-[2-(N-tert-butoxycarbonyl)amino-2-ethoxycarbonyl]ethyl-6-hydroxy-1-methyl-quinolinium iodide, 0.1 g of sodium bicarbonate, 15 mL of deaerated ethyl acetate and 10 mL of deaerated water was added, in one portion at room temperature under a nitrogen atmosphere, 0.15 g of sodium dithionite. The reaction mixture was stirred at that temperature for an additional 2 hours. The organic layer was separated, washed with deaerated water and saturated brine, dried over anhydrous sodium sulfate and evaporated in vacuo to give 60 mg of a brown solid melting at 123°–125° C. NMR (CDCl₃) δ 6.8–6.4 (3H, m), 5.8 (1H, bs), 5.0 (1H, m), 4.1–4.0 (3H, m), 3.45 (2H, bs), 3.0 (3H, s), 2.4 (2H, m), 1.4 (9H, s), 1.25 (3H, t); IR (KBr) ν 3400, 2970, 1730, 1685, 1510, 1370, 1230, 1155 cm⁻¹. Elemental analysis values were consistent with the assigned structure:

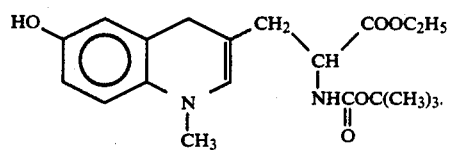

EXAMPLE 55

Preparation of N-Benzoyl-3-(1,2-dihydro-1-methylquinolin-3-yl)alanine methyl ester Repetition of the general procedure of EXAMPLE 21, substituting an equivalent quantity of 3-(2-benzoylamino-2-methoxycarbonyl)ethyl-1-methyl-quinolinium iodide for the 3-[2-(tert-butoxycarbonyl)amino-2-ethoxycarbonyl]ethyl-1-methylquinolinium iodide employed therein, affords a mixture of 1,2 and 1,4 dihydro derivatives. The title compound, which is the major product, has the structural formula

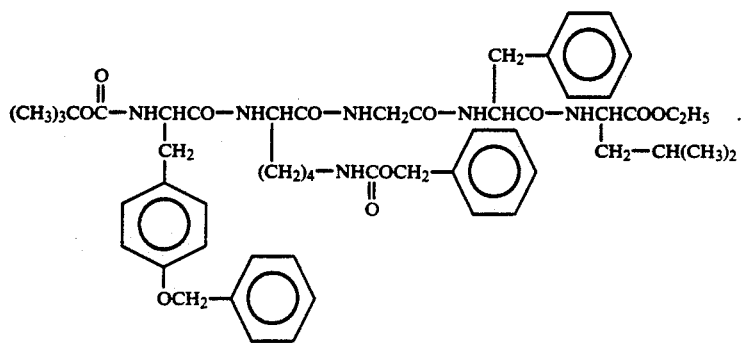

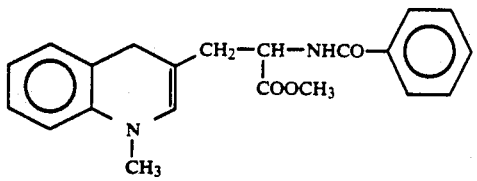

EXAMPLE 56

Preparation of
N-Benzoyl-3-(1,4-dihydro-1-methylquinolin-3-yl)alanine methyl ester When the general procedure of EXAMPLE 22 is repeated, substituting an equivalent quantity of 3-(2-benzoylamino-2-methoxycarbonyl)ethyl-1-methylquinolinium iodide for the 3-[2-(tert-butoxycarbonyl)amino-2-ethoxycarbonyl]ethyl-1-methylquinolinium iodide there employed, there is obtained, as the major product, the title compound of the formula

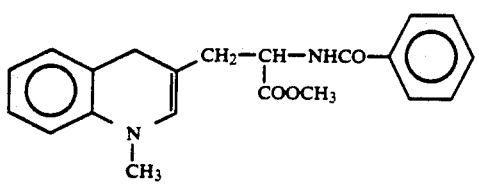

EXAMPLE 57

Preparation of
N-(tert-Butoxycarbonyl)-3-(3-carbamoyl-1,4-dihydropyridin-1-yl)-L-alanylglycine ethyl ester The procedure of EXAMPLE 25 is repeated, substituting an equivalent quantity of L-1-[2-(tert-butoxycarbonyl)amino-2-(N-ethoxycarbonylmethyl)carbamoyl]-ethyl-3-carbamoylpyridinium chloride for the L-1-[5-(tert-butoxycarbonyl)amino-5-methoxycarbonyl]pentyl-3-carbamoylpyridinium chloride used therein. Obtained in this manner is the title compound of the formula

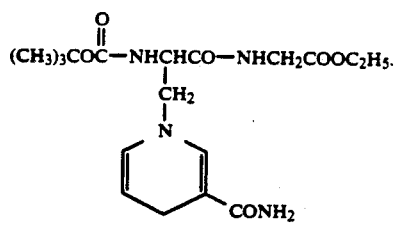

The title compound can alternatively be named as 1-[2-tert-butoxycarbonyl)amino-2-(N-ethoxycarbonylmethyl)carbamoyl]ethyl-3-carbamoyl-1,4-dihydropyridine.

EXAMPLE 58

Preparation of
N-(tert-Butoxycarbonyl)-3-(1,4-dihydro-6-methoxy-1-methylquinolin-3-yl)alanine ethyl ester The procedure of EXAMPLE 22 is followed, utilizing 0.1 g of 3-[2-N-(tert-butoxycarbonyl)amino-2-ethoxycarbonyl]ethyl-6-methoxy-1-methyl-3-quinolinium iodide, 10 mL of water, 0.1 g of sodium bicarbonate, 15 mL of ethyl acetate and 0.15 g of sodium dithionite. Prepared in this manner is the title compound of the formula:

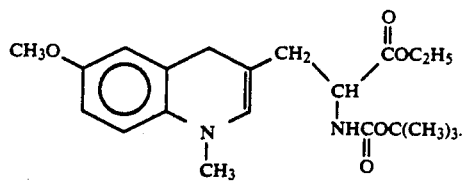

EXAMPLE 59

Preparation of
N-(tert-Butoxycarbonyl)glycyl-3-(1,4-dihydro-1-methylquinolin-3-yl)alanine ethyl ester The procedure of EXAMPLE 22 was followed, utilizing 0.12 g (0.22 mmol) of 3-{2-[N-(tert-butoxycarbonyl)glycyl]amino-2-ethoxycarbonyl}ethyl-1-methylquinolinium iodide, 12 mL of water, 0.11 g (1.3 mmol) of sodium bicarbonate, 12 mL of methylene chloride and 0.16 g of sodium dithionite. There were thus obtained 72 mg of the title compound. NMR values were consistent with the assigned structure:

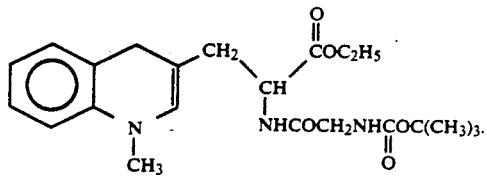

EXAMPLE 60

Preparation of
1-{5-[N-(tert-Butoxycarbonyl)-L-tyrosyl]amino-5-methoxycarbonyl}pentyl-3-carbamoyl-1,4-dihydropyridine When the general procedure of EXAMPLE 25 is repeated, using 1-{5-[N-(tert-butoxycarbonyl)-L-tyrosyl]amino-5-methoxycarbonyl}pentyl-3-carbamoylpyridinium chloride in place of the L-1-[5-(tert-butoxycarbonyl)amino-5-methoxycarbonyl]pentyl-3-carbamoylpyridinium chloride, there is obtained the title compound of the formula:

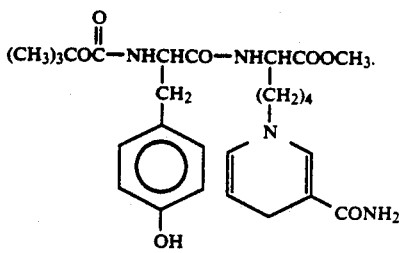

EXAMPLE 61

Preparation of
1-{5-[N-(tert-Butoxycarbonyl)-L-tyrosyl]amino-5-ethoxycarbonylmethylcarbamoyl}pentyl-3-carbamoyl-1,4-dihydropyridine The general procedure of EXAMPLE 22 is repeated, using 1-{5-[N-(tert-butoxycarbonyl)-L-tyrosyl]amino-5-ethoxycarbonylmethylcarbamoyl}pentyl-3-carbamoylpyridinium chloride in place of the 3-[2-(tert-butoxycarbonyl)amino-2-ethoxycarbonyl]ethyl-1-methylquinolinium iodide employed in that Example. Obtained in this manner is the title compound of the formula:

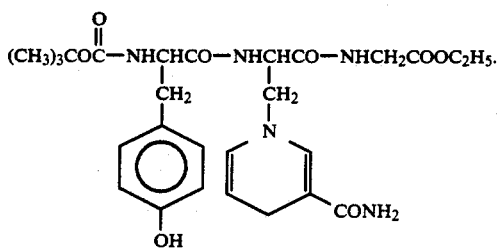

EXAMPLE 62

Preparation of
L-[2-(tert-Butoxycarbonyl)amino-3-(3-carbamoyl-1-pyridinium)]propionyl-L-phenylalanyl-L-leucine ethyl ester chloride Following the general procedure of EXAMPLE 3, but substituting N-(tert-butoxycarbonyl)-3-chloro-L-alanyl-L-phenylalanyl-L-leucine ethyl ester for the N-(tert-butoxycarbonyl)-3-chloro-L-alanylglycine ethyl ester there employed, affords the title compound of the formula:

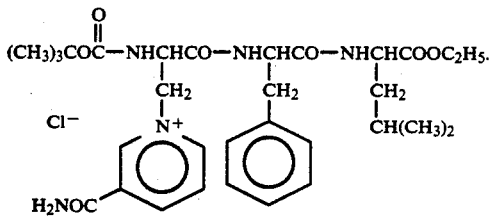

EXAMPLE 63

Preparation of
L-[2-(tert-Butoxycarbonyl)amino-3-(3-carbamoyl-1,4-dihydropyridin-1-yl)]propionyl-L-phenylalanyl-L-leucine ethyl ester The procedure of EXAMPLE 22 is repeated, using L-[2-tert-butoxycarbonyl)amino-3-(3-carbamoyl-1-pyridinium)]propionyl-L-phenylalanyl-L-leucine ethyl ester chloride in place of the 3-[2-(tert-butoxycarbonyl)amino-2-ethoxycarbonyl]ethyl-1-methylquinolinium iodide there employed. There is thus obtained the title compound of the formula:

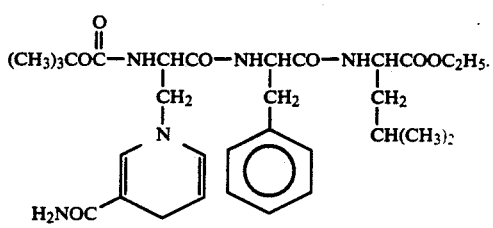

EXAMPLE 64

Preparation of
(S)-2-[N-(tert-Butoxycarbonyl)-L-tyrosyl]amino-6-(3-carbamoyl-1-pyridinium)hexanoylglycyl-L-phenylalanyl-L-leucine ethyl ester chloride A mixture of 1.0 g (1.02 mmol) of O-benzyl-N-(tert-butoxycarbonyl)-L-tyrosyl-N$^\epsilon$-benzyloxycarbonyl-L-lysylglycyl-L-phenylalanyl-L-leucine ethyl ester, 0.2 g of 10% palladium on carbon catalyst and 10 mL of dimethylformamide was stirred vigorously under a hydrogen atmosphere for 2 hours. The catalyst was removed by filtration and to the filtrate was added 0.33 g (1.02 mmol) of 3-carbamoyl-1-(2,4-dinitrophenyl)-pyridinium chloride. The reaction mixture was stirred overnight at room temperature, then evaporated. The residue was chromatographed on silica gel using acetonitrile, 3% aqueous acetonitrile and 6% aqueous acetonitrile successively as eluents, to give a brown oil. The oil was dissolved in distilled water, treated with active charcoal and lyophilized to give 0.34 g (37.9%) of the title compound as a colorless solid. NMR (CD$_3$OD) δ 9.45 (1H, bs), 9.1 (1H, d), 9.0 (1H, d), 8.2 (1H, dd), 7.3 (5H, bs), 7.1 (2H, d), 6.7 (2H, d), 4.15 (2H, ql), 3.8 (2H, bs), 3.2-2.8 (4H, m), 1.4 (9H, s), 1.25 (3H, t), 0.9 (6H, m). Elemental analysis was consistent with the assigned structure:

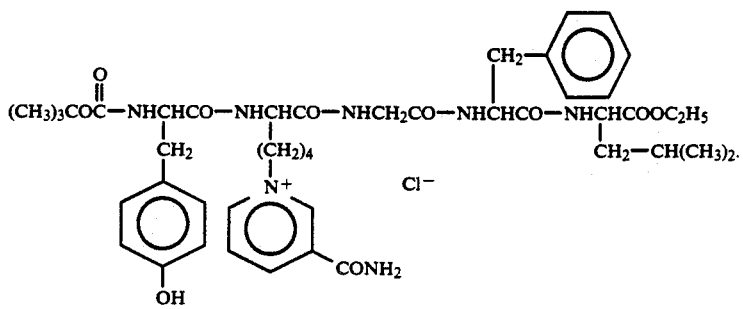

EXAMPLE 65

Preparation of (S)-2-[N-(tert-Butoxycarbonyl)-L-tyrosyl]amino-6-(3-carbamoyl-1,4-dihydropyridin-1-yl)hexanoylglycyl-L-phenylalanyl-L-leucine ethyl ester Repetition of the procedure of EXAMPLE 22, utilizing (S)-2-[N-(tert-butoxycarbonyl)-L-tyrosyl]amino-6-(3-carbamoyl-1-pyridinium)hexanoylglycyl-L-phenylalanyl-L-leucine ethyl ester chloride in place of the 3-[2-(tert-butoxycarbonyl)amino-2-ethoxycarbonyl]ethyl-1-methylquinolinium iodide there employed, affords the title compound of the structural formula:

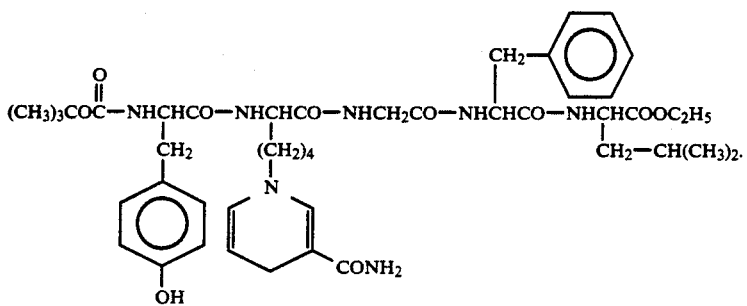

EXAMPLE 66

Preparation of (S)-1-[5-Amino-5-ethoxycarbonylmethylcarbamoyl]-pentyl-3-carbamoylpyridinium chloride hydrochloride A mixture of 0.1 mmol of (S)-1-[5-(tert-Butoxycarbonyl)amino-5-ethoxycarbonylmethylcarbamoyl]pentyl-3-carbamoylpyridinium chloride and 2 mL of ethanol saturated with HCl was stirred at 0° C. for 20 minutes. The reaction mixture was diluted with 20 mL of dry ethyl ether, decanted and washed with ethyl ether. The resultant precipitate was suspended in tert-butanol, evaporated and dried in vacuo to give the title compound as a white solid in 78.6% yield. NMR (DMSO-$d_6$) δ 9.85 (1H, bs), 9.4 (2H, m), 9.0 (2H, dd), 8.5 (2H, m), 8.4–8.1 (3H, m), 4.8 (2H, m), 4.2–3.8 (6H, m), 1.2 (3H, t). Elemental analysis was consistent with the assigned structure:

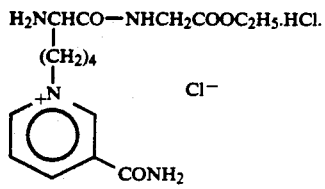

The product can also be named (S)-2-amino-6-(3-carbamoyl-1-pyridinium)hexanoylglycine ethyl ester chloride hydrochloride.

EXAMPLE 67

Preparation of (S)-[2-Amino-6-(3-carbamoyl-1-pyridinium)]hexanoyl-L-phenylalanyl-L-leucine ethyl ester chloride hydrochloride The procedure of EXAMPLE 66 was repeated, using (S)-[2-(tert-butoxycarbonyl)amino-6-(3-carbamoyl-1-pyridinium)]hexanoyl-L-phenylalanyl-L-leucine ethyl ester chloride as the starting material. The title compound was obtained in 89.1% yield. NMR (DMSO-$d_6$) δ 9.8 (1H, bs), 9.35 (1H, bd), 9.1–8.8 (2H, m), 8.7–8.1 (6H, m), 7.3 (5H, m), 4.7 (3H, m), 4.05 (2H, q), 3.8 (1H, m), 3.0 (2H, m), 1.2 (3H, t), 0.9 (6H, m). Elemental analysis was consistent with the assigned structure:

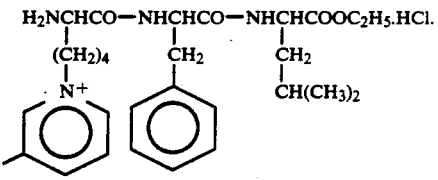

EXAMPLE 68

Preparation of (S)-2-(L-Tyrosyl)amino-6-(3-carbamoyl-1-pyridinium)-hexanoylglycyl-L-phenylalanyl-L-leucine ethyl ester chloride hydrochloride The procedure of EXAMPLE 66 was repeated, using (S)-2-[N-(tert-butoxycarbonyl-L-tyrosyl]amino-6-(3-carbamoyl-1-pyridinium)hexanoylglycyl-L-phenylalanyl-L-leucine ethyl ester chloride as the starting material. The title compound was obtained in 78.6% yield. NMR (DMSO-$d_6$) δ 9.75 (1H, bs), 9.3 (1H, d), 9.0 (1H, d), 8.85 (1H, m), 8.6–8.0 (m), 7.25 (5H, m), 7.1 (2H, d), 6.7 (2H, d), 4.7 (2H, m), 1.15 (2H, t), 0.9 (6H, m). Elemental analysis was consistent with the assigned structure:

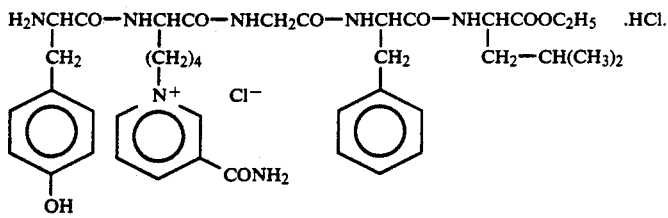

EXAMPLE 69

Preparation of
(S)-1-[5-(L-Tyrosyl)amino-5-ethoxycarbonylmethyl-carbamoyl]pentyl-3-carbamoylpyridinium chloride hydrochloride Repetition of the procedure of EXAMPLE 66, but using (S)-1-{5-[N-(tert-butoxycarbonyl)-L-tyrosyl]-amino-5-ethoxycarbonylmethylcarbamoyl}pentyl-3-carbamoylpyridinium chloride as the starting material, affords the title compound of the formula:

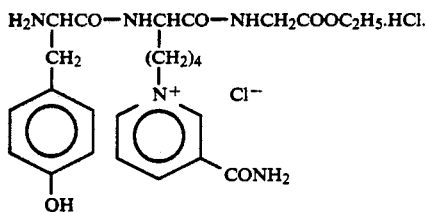

The product can also be named (S)-2-(L-tyrosyl)amino-6-(3-carbamoyl-1-pyridinium)hexanoylglycine ethyl ester chloride hydrochloride.

EXAMPLE 70

Preparation of 1,4-Dihydro Derivatives from the Corresponding Quaternary Salts

The quaternary salts of the invention, e.g. the products of EXAMPLES 3, 6, 9, 17, 20, 33, 39, 41, 42, 44, 46, 49, 51, 62, 64, 66, 67, 68 and 69 may be selectively converted to the corresponding 1,4-dihydro derivatives using the following procedure:

A solution of 4 mmol of the selected quaternary salt and 4.6 mmol of N-benzyl-1,2-dihydroisonicotinamide in anhydrous methanol is stirred under nitrogen at 0° C. for 2 hours. The reaction mixture is evaporated in vacuo at 30° C. and the residue is suspended in 1,2-dichloroethane, filtered and washed with the same solvent. The filtrate is evaporated in vacuo to a small volume and then flash chromatographed over a column of 150 mesh activated neutral aluminum oxide, eluting first with 1,2-dichloroethane and then with 1:4 acetonitrile/1,2-dichloroethane. The solution is evaporated in vacuo at 30° C. and crystallized.

The peptides of structure (A) which are provided by this invention are typically administered to mammals by incorporating the selected peptide in a pharmaceutical composition comprising the peptide or a non-toxic pharmaceutically acceptable salt thereof and a non-toxic pharmaceutically acceptable carrier therefor. The peptide or its salt is employed in an effective amount, i.e. an amount sufficient to evoke the desired pharmacological response. Thus, for example, the enkephalin analogs of the invention may be employed in an analgesically effective amount; the LHRH agonist analogs of the invention may be used in an amount sufficient to control LH or FSH or to have the desired effect on the reproductive system (e.g. one or more of the physiological and paradoxical utilities disclosed in Nestor et al U.S. Pat. No. 4,530,920); and so forth.

Suitable non-toxic pharmaceutically acceptable carriers for use with the selected peptide of structure (A) will be apparent to those skilled in the art of pharmaceutical formulation. See, for example, Remington's Pharmaceutical Sciences, seventeenth edition, ed. Alfonso R. Gennaro, Mack Publishing Company, Easton, Penn. (1985). Obviously, the choice of suitable carriers will depend upon the exact nature of the particular dosage form selected, as well as upon the identity of the peptide to be administered. The therapeutic dosage range can be estimated on the basis of animal tests, e.g. in the case of the LHRH agonist analogs, on the basis of tests described in the Nestor et al patent referred to hereinabove. Naturally, such therapeutic dosage ranges will vary with the particular peptide of structure (A) used, the size, species and condition of the subject, the severity of the subject's condition, the particular dosage form employed, the route of administration and the like. And the quantity of given dosage form needed to deliver the desired dose will of course depend upon the concentration of the peptide of structure (A) in any given pharmaceutical composition/dosage form thereof. In addition, the active ingredient may be formulated into a sustained release carrier system and/or a route of administration may be selected to slowly release the chemical, e.g. subcutaneous implantation or transdermal delivery.

Routes of administration contemplated for the peptides of structure (A) and pharmaceutical compositions containing them are any of the routes generally used for treatment of the types of conditions for which the peptides are administered. These include parenteral (intravenous, intramuscular, subcutaneous), vaginal, rectal, nasal, oral and buccal routes. Appropriate dosage forms for these routes of administration will be apparent to those skilled in the art; see, for example, Nestor et al U.S. Pat. No. 4,530,920. While any of these routes of administration/dosage forms are contemplated for peptides of structure (A) whose terminal amino and carboxyl functions are appropriately protected by the protecting groups described herein for use in vivo, unprotected peptides having structure (A) may be administered in parental dosage forms suitable for direct injection into the brain.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What is claimed is:

1. A quaternary salt having the formula

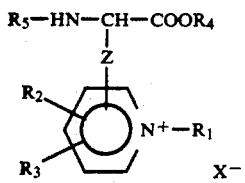

wherein X⁻ is the anion of a non-toxic pharmaceutically acceptable acid; Z is either a direct bond or $C_1-C_6$ alkylene and can be attached to the heterocyclic ring via a ring carbon atom or via the ring nitrogen atom; $R_1$ is $C_1-C_7$ alkyl, $C_1-C_7$ haloalkyl or $C_7-C_{12}$ aralkyl when Z is attached to a ring carbon atom; $R_1$ is a direct bond when Z is attached to the ring nitrogen atom; $R_2$ and $R_3$, which can be the same or different, are selected from the group consisting of hydrogen, halo, cyano, $C_1-C_7$ alkyl, $C_1-C_7$ alkoxy, $C_2-C_8$ alkoxycarbonyl, $C_2-C_8$ alkanoyloxy, $C_1-C_7$ haloalkyl, $C_1-C_7$ alkylthio, $C_1-C_7$ alkylsulfinyl, $C_1-C_7$ alkylsulfonyl, —CH=NOR''' wherein R''' is hydrogen or $C_1-C_7$ alkyl, and —CONR'R" wherein R' and R", which can be the same or different, are each hydrogen or $C_1-C_7$ alkyl; or one of $R_2$ and $R_3$ together with the adjacent ring carbon atom forms a benzene ring fused to the heterocyclic ring, which benzene ring may optionally bear one or two substituents, which can be the same or different, selected from the group consisting of hydroxy, protected hydroxy, halo, cyano, $C_1-C_7$ alkyl, $C_1-C_7$ alkoxy, $C_2-C_8$ alkoxycarbonyl, $C_2-C_8$ alkanoyloxy, $C_1-C_7$ haloalkyl, $C_1-C_7$ alkylthio, $C_1-C_7$ alkylsulfinyl, $C_1-C_7$ alkylsulfonyl, —CH=NOR''' wherein R''' is hydrogen or $C_1-C_7$ alkyl, and —CONR'R" wherein R' and R", which can be the same or different, are each hydrogen or $C_1-C_7$ alkyl; $R_4$ is hydrogen or a carboxyl protective group; and $R_5$ is hydrogen or an amino protective group, said carboxyl protective group and said amino protective group being designed to protect the carboxyl and amino functions during synthesis or to improve lipoidal characteristics and prevent premature metabolism of said functions in vivo.

2. A quaternary salt having the formula

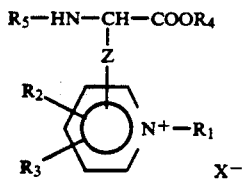

wherein X⁻ is the anion of a non-toxic pharmaceutically acceptable acid; Z is either a direct bond or $C_1-C_6$ alkylene and can be attached to the heterocyclic ring via a ring carbon atom or via the ring nitrogen atom; $R_1$ is $C_1-C_7$ alkyl, $C_1-C_7$ haloalkyl or $C_7-C_{12}$ aralkyl when Z is attached to a ring carbon atom; $R_1$ is a direct bond when Z is attached to the ring nitrogen atom; $R_2$ and $R_3$, which can be the same or different, are selected from the group consisting of hydrogen, halo, cyano, $C_1-C_7$ alkyl, $C_1-C_7$ alkoxy, $C_2-C_8$ alkoxycarbonyl, $C_2-C_8$ alkanoyloxy, $C_1-C_7$ haloalkyl, $C_1-C_7$ alkylthio, $C_1-C_7$ alkylsulfinyl, $C_1-C_7$ alkylsulfonyl, —CH=NOR''' wherein R''' is hydrogen or $C_1-C_7$ alkyl, and —CONR'R" wherein R' and R", which can be the same or different, are each hydrogen or $C_1-C_7$ alkyl; $R_4$ is hydrogen or a carboxyl protective group and $R_5$ is hydrogen or an amino protective group, said carboxyl protective group and said amino protective group being designed to protect the carboxyl and amino functions during synthesis or to improve lipoidal characteristics and prevent premature metabolism of said functions in vivo.

3. A quaternary salt according to claim 2 wherein Z is —$CH_2$—.

4. A quaternary salt according to claim 2 wherein Z is —$(CH_2)_4$—.

5. A quaternary salt according to claim 2 wherein $R_1$ is a direct bond and Z is attached to the ring nitrogen atom.

6. A quaternary salt according to claim 5 wherein one of $R_2$ and $R_3$ is hydrogen.

7. A quaternary salt according to claim 6 wherein the other of $R_2$ and $R_3$ is —$CONH_2$—.

8. A quaternary salt according to claim 1 wherein $R_1$ is a direct bond, Z is attached to the ring nitrogen atom, one of $R_2$ and $R_3$ is —$CONH_2$ and the other of $R_2$ and $R_3$ together with the adjacent ring carbon atom forms a benzene ring fused to the heterocyclic ring.

9. A quaternary salt according to claim 2 wherein $R_1$ is methyl.

10. A quaternary salt according to claim 2 wherein Z is attached to a ring carbom atom.

11. A quaternary salt according to claim 10 wherein $R_1$ is methyl.

12. A quaternary salt according to claim 10 wherein at least one of $R_2$ and $R_3$ is hydrogen.

13. A quaternary salt according to claim 12 wherein both $R_2$ and $R_3$ are hydrogen.

14. A quaternary salt according to claim 1 wherein Z is attached to a ring carbon atom, one of $R_2$ and $R_3$ is hydrogen and the other of $R_2$ and $R_3$ together with the adjacent ring carbon atom forms an unsubstituted benzene ring fused to the heterocyclic ring.

15. A quaternary salt according to claim 1 wherein Z is attached to a ring carbon atom, one of $R_2$ and $R_3$ is hydrogen and the other of $R_2$ and $R_3$ together with the adjacent ring carbon atom forms a benzene ring fused to the heterocyclic ring, said benzene ring bearing one substituent selected from the group consisting of hydroxy, protected hydroxy and methoxy.

16. A quaternary salt according to claim 2 wherein $R_4$ is a carboxyl protective group.

17. A quaternary salt according to claim 2 wherein $R_5$ is an amino protective group.

18. A quaternary salt according to claim 2 wherein

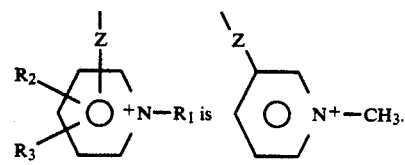

19. A quaternary salt according to claim 2 wherein

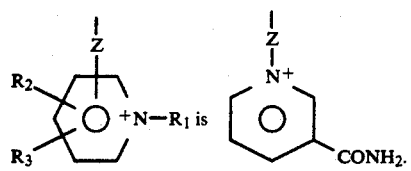

20. A quaternary salt according to claim 1 wherein

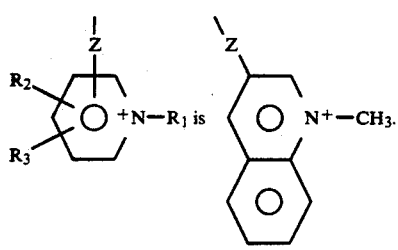

21. A quaternary salt according to claim 1 wherein

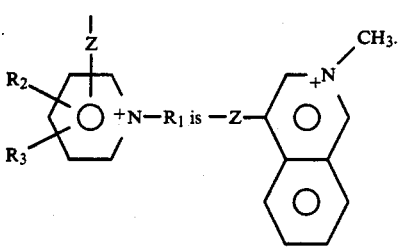

22. A quaternary salt according to claim 1 wherein

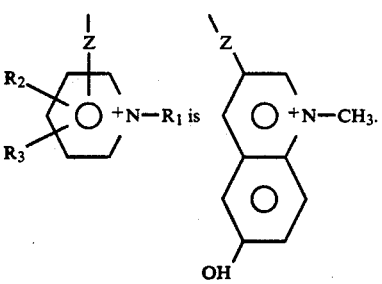

23. A quaternary salt according to claim 1 wherein

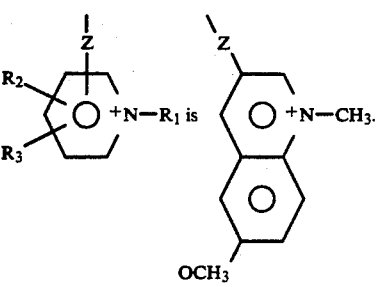

24. A quaternary salt according to claim 1 wherein

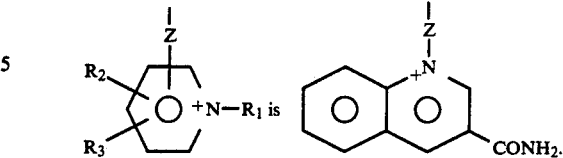

25. A quaternary salt according to claim 1 wherein

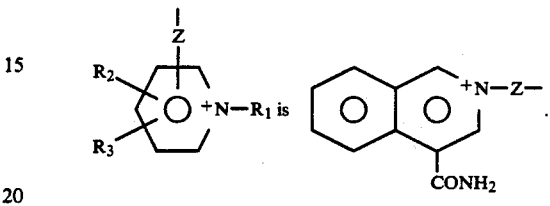

26. A quaternary salt according to claim 1 having the formula

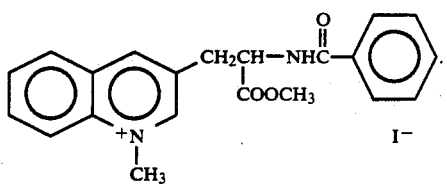

27. A quaternary salt according to claim 2 having the formula

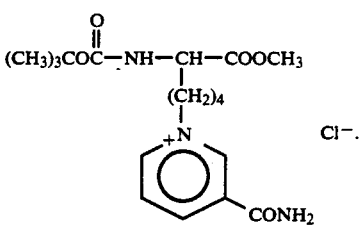

28. A quaternary salt according to claim 1 having the formula

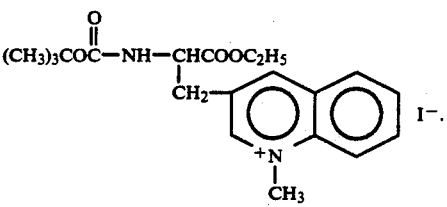

29. A quaternary salt according to claim 1 having the formula

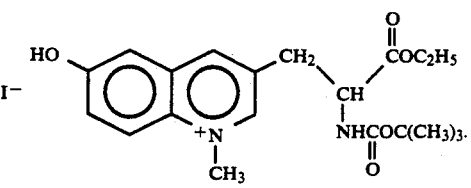

30. A quaternary salt according to claim 1 having the formula
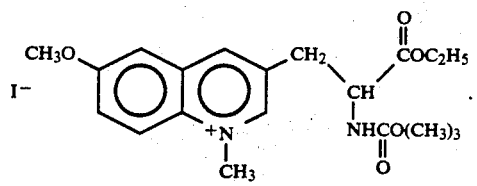
* * * * *